US009428725B2

(12) United States Patent
Brown et al.

(10) Patent No.: US 9,428,725 B2
(45) Date of Patent: *Aug. 30, 2016

(54) COMPOSITIONS AND METHODS FOR CAPTURE AND ELUTION OF BIOLOGICAL MATERIALS VIA PARTICULATES

(71) Applicant: Claremont BioSolutions, LLC, Upland, CA (US)

(72) Inventors: Mark Brown, Pasadena, CA (US); Robert Doebler, Upland, CA (US); Bruce Irvine, Glendora, CA (US); Tanya Ferguson, South Pasadena, CA (US); Gary Blackburn, Glendora, CA (US)

(73) Assignee: Claremont Biosolutions LLC, Upland, CA (US)

( * ) Notice: Subject to any disclaimer, the term of this patent is extended or adjusted under 35 U.S.C. 154(b) by 89 days.

This patent is subject to a terminal disclaimer.

(21) Appl. No.: 14/155,123

(22) Filed: Jan. 14, 2014

(65) Prior Publication Data

US 2014/0127773 A1    May 8, 2014

Related U.S. Application Data

(63) Continuation of application No. 13/336,932, filed on Dec. 23, 2011, now Pat. No. 8,663,974.

(60) Provisional application No. 61/444,607, filed on Feb. 18, 2011, provisional application No. 61/427,045, filed on Dec. 23, 2010.

(51) Int. Cl.

| C12M 1/00 | (2006.01) |
|---|---|
| C12Q 1/00 | (2006.01) |
| C12Q 1/68 | (2006.01) |
| C12Q 1/02 | (2006.01) |
| G01N 33/48 | (2006.01) |
| B01L 3/00 | (2006.01) |
| C12N 1/06 | (2006.01) |
| G01N 33/543 | (2006.01) |
| G01N 1/28 | (2006.01) |
| G01N 1/40 | (2006.01) |

(52) U.S. Cl.
CPC ............... *C12N 1/06* (2013.01); *C12M 47/06* (2013.01); *G01N 33/54313* (2013.01); *B01L 3/563* (2013.01); *B01L 3/567* (2013.01); *G01N 2001/2866* (2013.01); *G01N 2001/4088* (2013.01)

(58) Field of Classification Search
CPC ........... C12Q 1/68; C12M 1/00; C12M 1/34; G01N 33/483; G01N 27/447
USPC ...... 435/4, 6.1, 29, 283.1; 422/50, 68.1, 500
See application file for complete search history.

(56) References Cited

U.S. PATENT DOCUMENTS

| 5,211,850 A | 5/1993 | Shettigar et al. |
| 5,464,773 A | 11/1995 | Melendez et al. |
| 6,455,287 B1 | 9/2002 | Jem |
| 6,881,541 B2 | 4/2005 | Petersen et al. |
| 8,268,603 B2 | 9/2012 | Taylor et al. |
| 8,663,974 B2 | 3/2014 | Brown et al. |
| 2007/0248958 A1 | 10/2007 | Jovanovich et al. |
| 2007/0292941 A1 | 12/2007 | Handique et al. |
| 2010/0178697 A1 | 7/2010 | Doebler et al. |

FOREIGN PATENT DOCUMENTS

| EP | 1 767 630 A1 | 3/2007 |
| KR | 10-0700093 B1 | 3/2007 |
| WO | 2004/040001 A2 | 5/2004 |
| WO | 2009/089466 A2 | 7/2009 |

OTHER PUBLICATIONS

Belgrader et al., "A Minisonicator to Rapidly Disrupt Bacterial Spores for DNA Analysis" *Anal. Chem.* 71:4232-4236, 1999.
Boom et al., "Rapid and Simple Method for Purification of Nucleic Acids," *Journal of Clinical Microbiology* 28:495-503, 1990.
DeAngelis et al., "Solid-phase reversible immobilization for the isolation of PCR products" *Nucleic Acids Research* 23(22):4742-4743, 1995.
Doebler et al., "Continuous-Flow, Rapid Lysis Devices for Biodefense Nucleic Acid Diagnostic Systems" *JALA* 14:119-125, 2009.
Doebler et al., "System, Apparatus and Method for Lysing," U.S. Appl. No. 61/020,072, filed Jan. 9, 2008, 62 pages.
Extended European Search Report, dated Sep. 5, 2014, for Application No. 10792687.5, 8 pages.
Lichty et al., "Comparison of affinity tags for protein purification," *Protein Expression and Purification* 41:98-105, 2005.
Porter et al., "Rapid and Efficient Recovery of Histidine-tagged Proteins Directly from Bacterial Cultures," *The FASEB Journal* 20(4):A530-A531, 2006.
Irvine et al., "Capture and Elution of Bio-Analytes Via Beads That Are Used to Disrupt Specimens," U.S. Appl. No. 61/220,984, filed Jun. 26, 2009, 67 pages.
Irvine et al., "Capture and Elution of Bio-Analytes Via Beads That Are Used to Disrupt Specimens," U.S. Appl. No. 61/317,604, filed Mar. 25, 2010, 91 pages.
Kim et al., "Cell lysis on a microfluidic CD (compact disc)" *Lab Chip* 4:516-522, 2004.

*Primary Examiner* — Narayan Bhat
(74) *Attorney, Agent, or Firm* — Seed IP Law Group PLLC

(57) ABSTRACT

A flow-through device for capturing a biological material from a fluid specimen and lysing the fluid specimen. The flow through device may include a first chamber containing a portion of the fluid specimen and a solid phase material retained in the first chamber. The solid phase material may have an affinity for the biological material in the fluid specimen. The first chamber may include an inlet opening which allows flow of the fluid specimen into the first chamber. The first chamber may also include an outlet opening which allows flow of the fluid specimen out of the first chamber. The flow through device may include a second chamber fluidly connected to the first chamber. The second chamber may include a portion of the fluid specimen and an impeller. The impeller may in use impart rotational motion to the fluid specimen to mechanically lyse the fluid specimen.

22 Claims, 40 Drawing Sheets

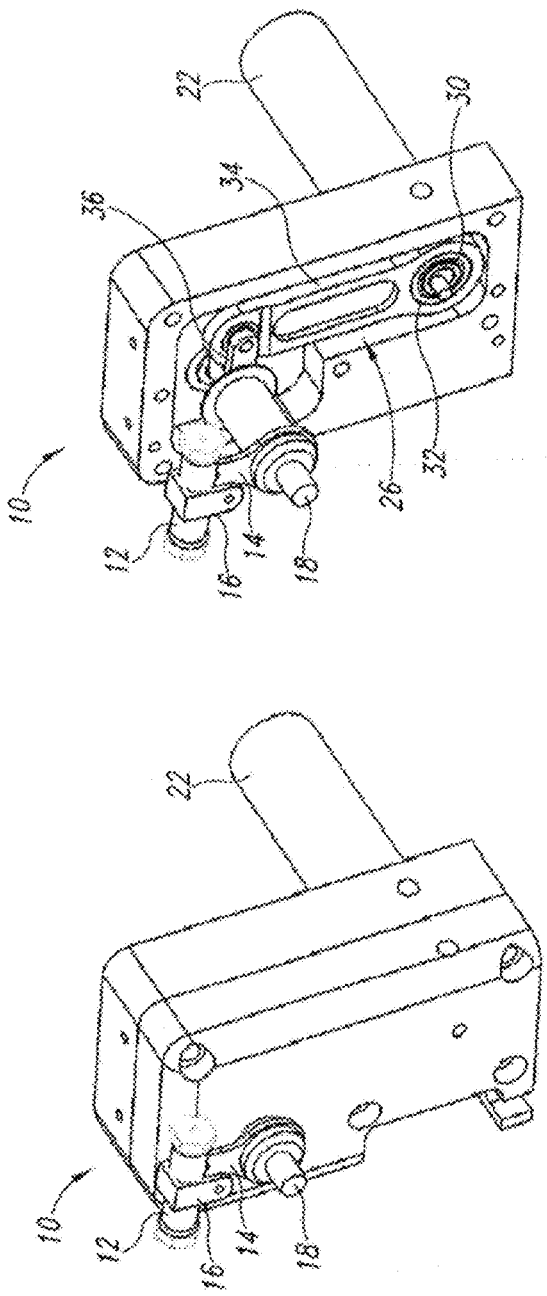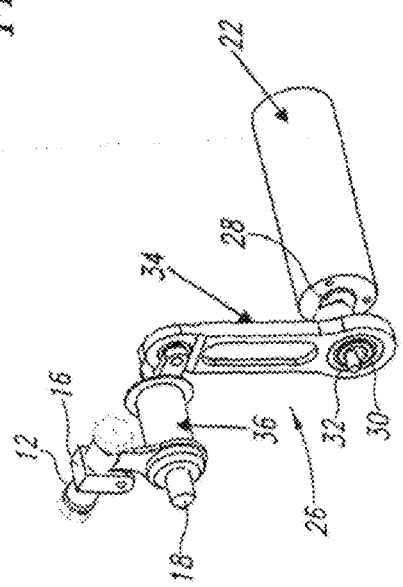

1100

```
┌─────────────────────────────────────────────────────┐
│  EVACUATE OF THE LYSED MATERIAL DURING EACH CYCLE OF THE │
│  INTERMITTENT PUMPING BY THE PUMPING INTO THE CHAMBER OF │──1102
│              MORE MATERIAL TO BE LYSED               │
└─────────────────────────────────────────────────────┘
```

```
┌─────────────────────────────────────────────────────┐
│  EVACUATE OF THE LYSED MATERIAL DURING EACH CYCLE OF THE │
│  INTERMITTENT PUMPING BY THE PUMPING INERT FLUID INTO THE │──1202
│                       CHAMBER                         │
└─────────────────────────────────────────────────────┘
```

```
┌─────────────────────────────────────────────────────┐
│   CONTINUOUSLY PUMP THE MATERIAL TO BE LYSED INTO THE   │──1320
│          CHAMBER WHILE OSCILLATING THE CHAMBER          │
└─────────────────────────────────────────────────────┘
```

```
┌─────────────────────────────────────────────────────┐
│    ADJUST FLOW RATE OF PUMPING OF MATERIAL TO BE LYSED   │
│  BASED ON LENGTH OF THE CHAMBER SUCH THAT MATERIAL TO BY │──1402
│   LYSED SPENDS SUFFICIENT TIME IN CHAMBER TO ACHIEVE DESIRED │
│                      LEVEL OF LYSING                     │
└─────────────────────────────────────────────────────┘
```

```
┌─────────────────────────────────────────────────────┐
│   DIRECT LYSED MATERIAL REMOVED FROM THE CHAMBER TO AT   │──1502
│              LEAST ONE ANALYSIS DEVICE               │
└─────────────────────────────────────────────────────┘
                            │
                            ▼
┌─────────────────────────────────────────────────────┐
│                ANALYZE LYSED MATERIAL                │──1504
└─────────────────────────────────────────────────────┘
```

*FIG. 15*

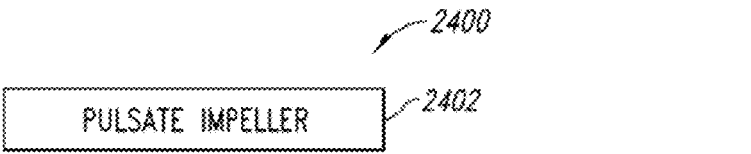
FIG. 24
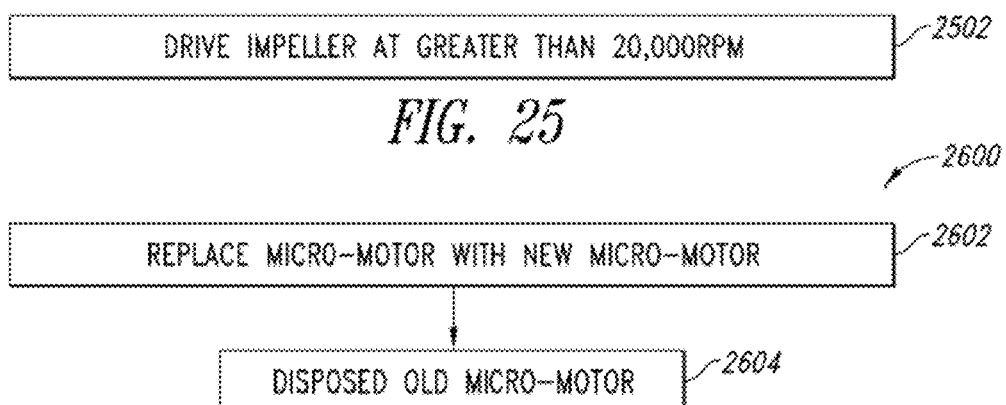
FIG. 25
FIG. 26
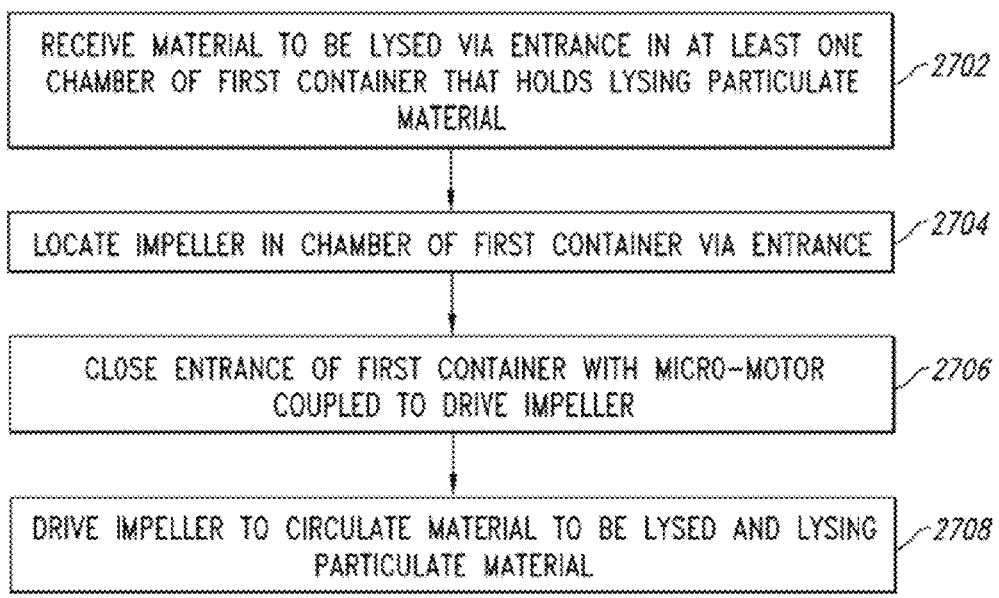
FIG. 27

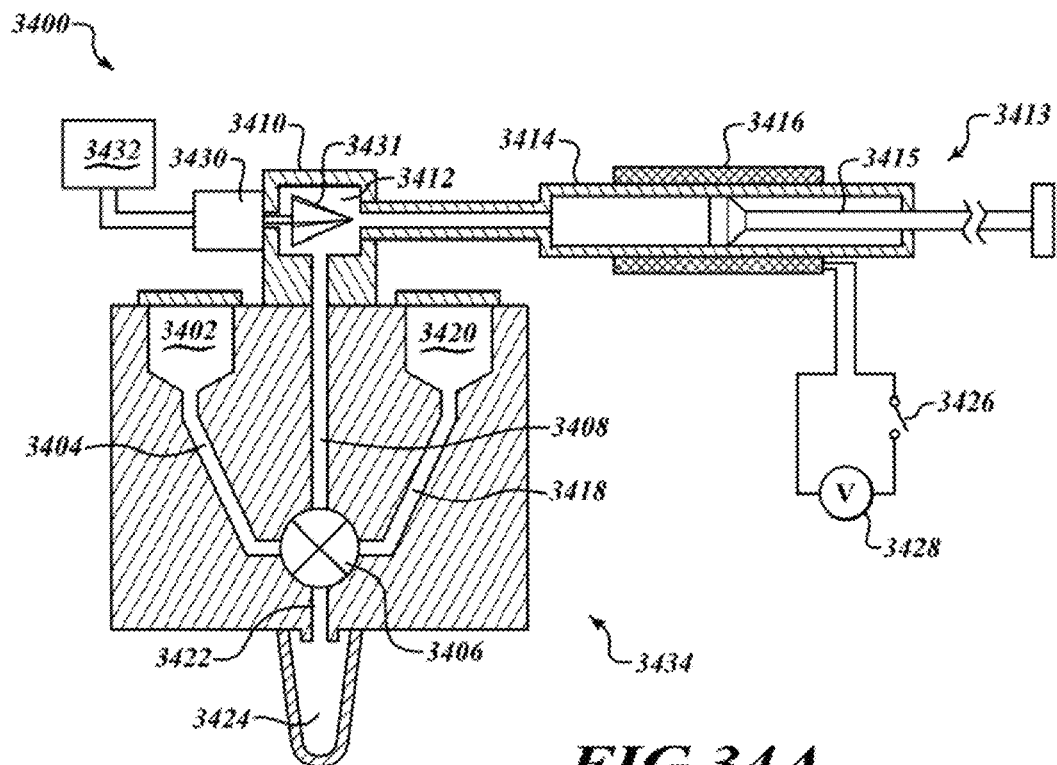
FIG.34A
FIG.34B
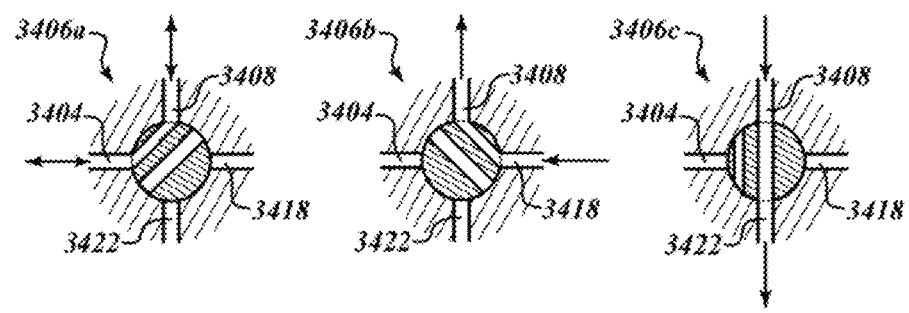

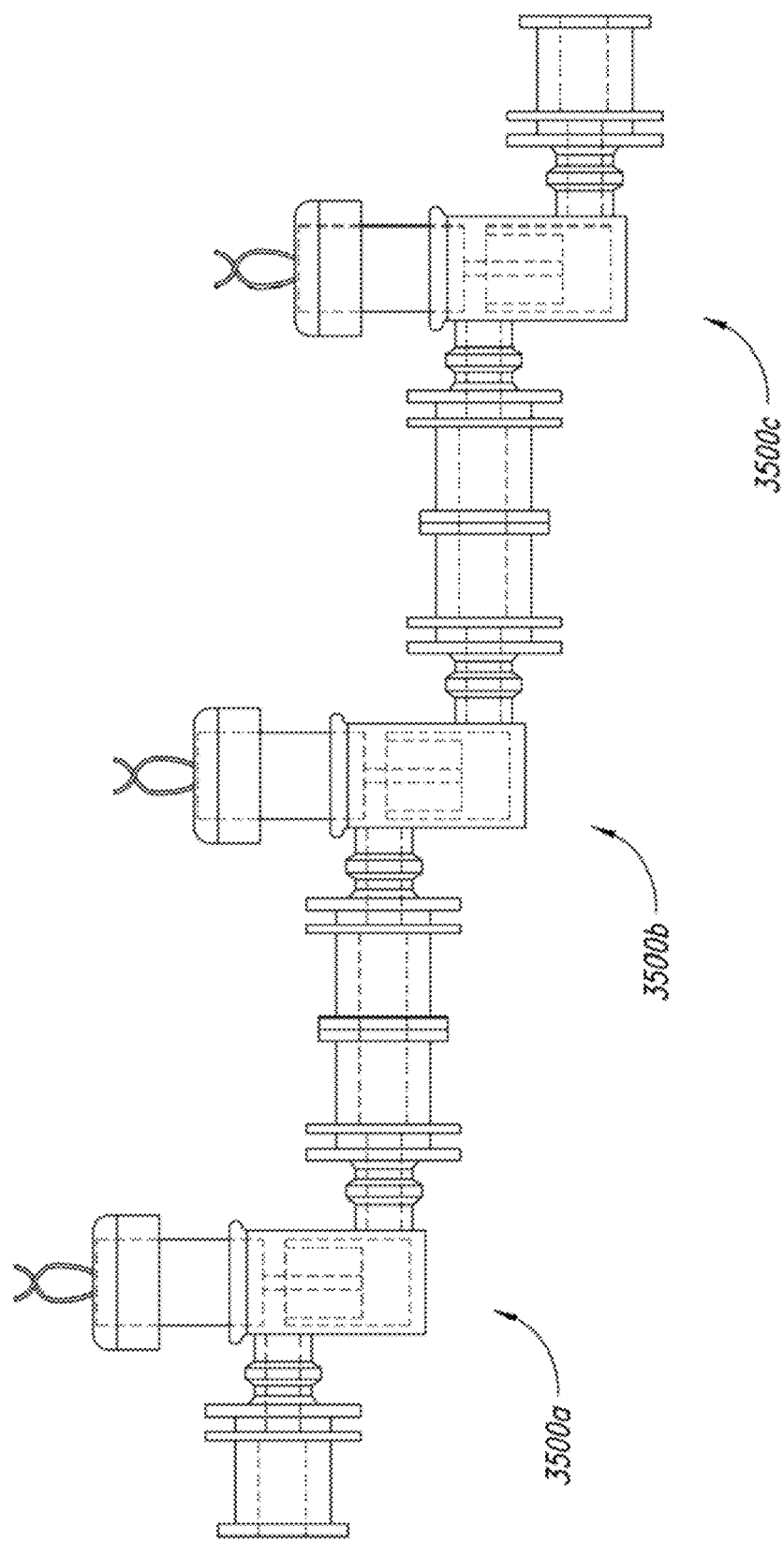

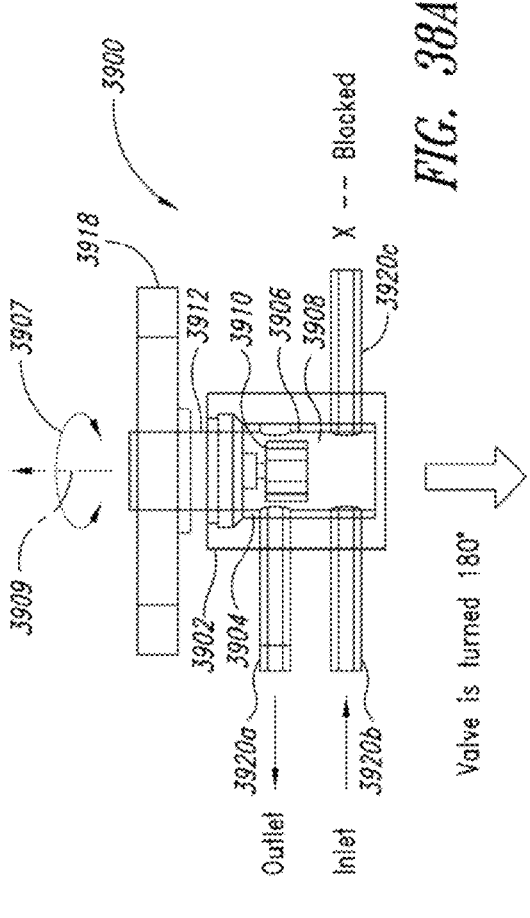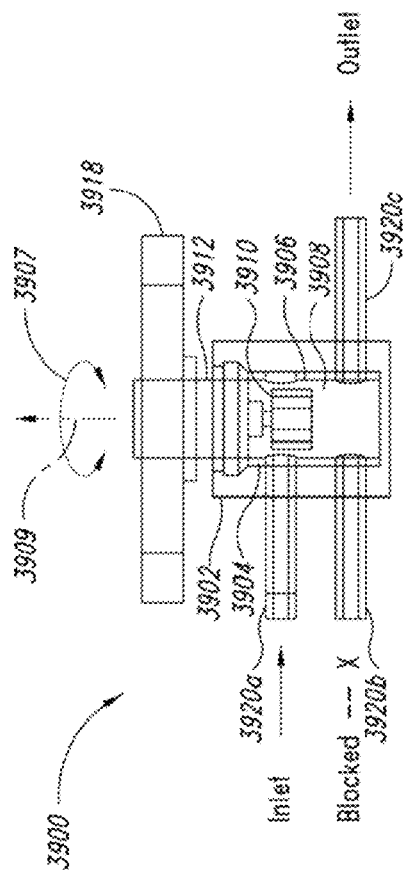

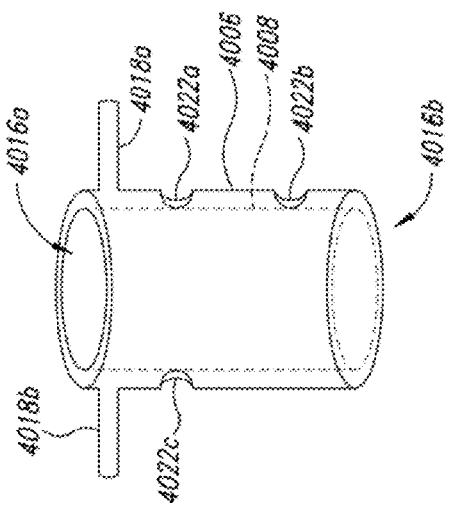
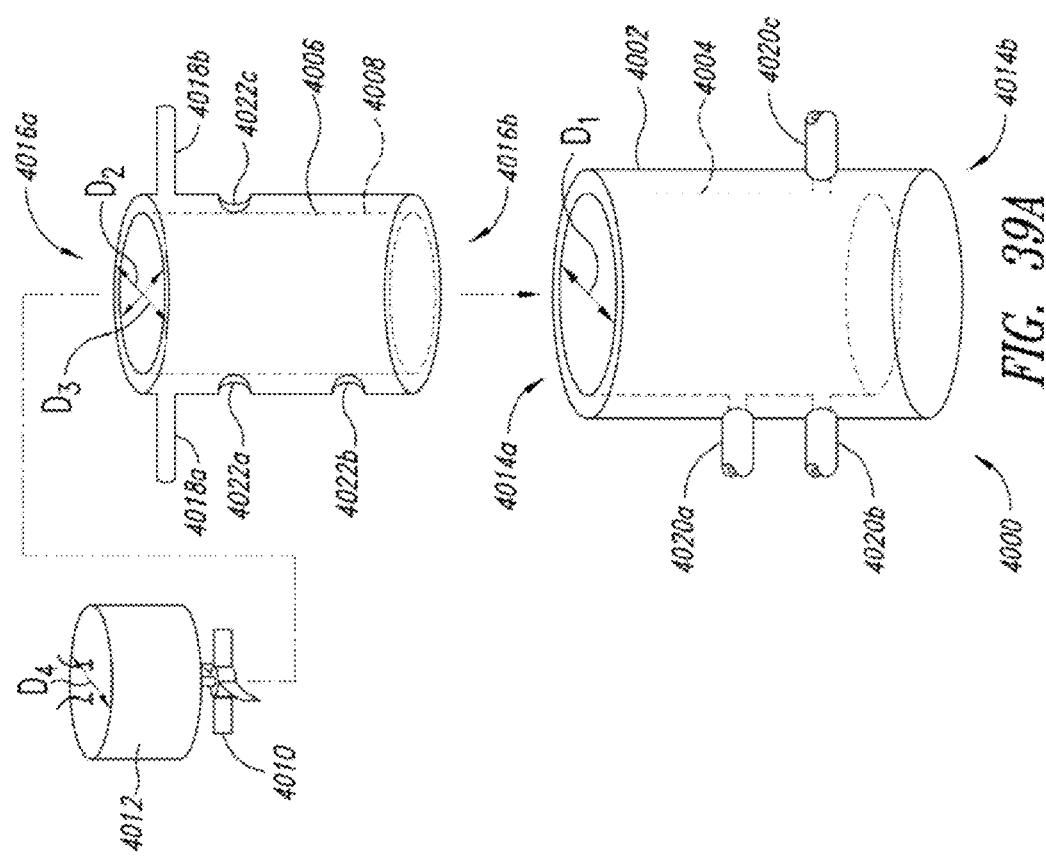
FIG. 39C
FIG. 39A

```
SEQUENCE LISTING

<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: Surface bound ligand sequence

<400> SEQUENCE: 1

Asp Tyr Lys Asp Asp Asp Asp Lys
1               5

<210> SEQ ID NO 2
<211> LENGTH: 10
<212> TYPE: PRT
<213> ORGANISM: Artificial Sequence
<220> FEATURE:
<223> OTHER INFORMATION: Surface bound ligand sequence

<400> SEQUENCE: 2

Glu Gln Lys Leu Ile Ser Glu Glu Asp Leu
1               5                   10
```

COMPOSITIONS AND METHODS FOR CAPTURE AND ELUTION OF BIOLOGICAL MATERIALS VIA PARTICULATES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200184_402C1_SEQUENCE_LISTING.txt. The text file is 875 bytes, was created on Jul. 2, 2013, and is being submitted electronically via EFS-Web.

TECHNICAL FIELD

The present disclosure relates to extraction, capture and elution of biological material, for example nucleic acids such as DNA, from biological specimens using particulate materials. The present disclosure also relates to lysing and in particular to systems, apparatus and methods to perform lysing of a biological material to be lysed using a lysing particulate material.

BACKGROUND

Lysis of biological specimens, for example cell lysis, is used to provide biological materials for compositional analysis. Specific biological materials may include proteins, lipids, and nucleic acids either individually or as complexes. When a cell membrane is lysed, certain organelles—nuclei, mitochondria, lysosomes, chloroplasts, and/or endoplasmic reticulum—may be isolated. Such may be analyzed using methods such as polymerase chain reaction (PCR), electron microscopy, Western blotting or other analysis techniques.

There are numerous approaches to performing lysis. For example, enzymatic approaches may be employed to remove cell walls using appropriate enzymes in preparation for cell disruption or to prepare protoplasts. Another approach employs detergents to chemically disrupt cell membranes. These chemical approaches may adversely affect the resulting product, for example degrading the bio-products being released. Consequently, chemical approaches may, in some instances, not be practical.

Yet another approach employs ultrasound to produce cavitation and impaction for disrupting the cells. Such an approach may not achieve as high a lysis efficiency as may be required or desired for many applications.

Yet still another approach employs beads (e.g., glass or ceramic) which are agitated, for example, via a vortex mixer. Such an approach successfully addresses the issues raised by chemical lysis approaches, yet improvements in such an approach are desirable.

Particular biological materials that are isolated from the interior of cells or viruses for use in a variety of analysis or testing procedures include nucleic acids. These may be isolated and used, for example, in testing for bacterial or viral infections. Nucleic acid analysis or testing for such purposes may provide improved sensitivity or may shorten the time between incidence of an infection and appearance of a positive test, compared to results obtained from more traditional antibody testing. Nucleic acid analysis or testing typically involves extraction and isolation of a nucleic acid of interest, e.g., deoxyribonucleic acid (DNA), from the biological specimens, followed by amplification reactions, such as PCR. Amplification of the isolated nucleic acid increases the sensitivity of detection and identification of the resulting nucleic acid.

Commonly used techniques for rapid extraction and isolation of nucleic acids, in particular DNA, from cells utilize membranes or beads, including magnetic beads, that are made from silica or from other materials that capture DNA nonspecifically on the basis of the polyanionic chemistry of DNA. Most such techniques rely on the use of harsh reagents, such as chaotropic salts, e.g., guanidinium hydrochloride, guanidinium thiocyanate, or proteases, to lyse cells to free the DNA. The harsh reagents used in such methods of DNA isolation are not compatible with subsequent amplification reactions. The reagents must thus be thoroughly removed, often by numerous wash steps, prior to elution and subsequent use or analysis of the isolated DNA. Even the wash steps may include reagents that are incompatible with subsequent reactions and must thus be removed. For example, washes may include alcohol which must then be removed by evaporation. Additionally, methods for isolating biological materials of interest, such as DNA, may co-isolate other biological materials that may interfere with subsequent analyses. Approaches that eliminate such manipulations, particularly the use and removal of harsh reagents or co-isolation of undesirable biological materials as contaminants in the products, could advantageously improve the efficiency of the process and the utility of the isolated product, and could thus simplify and optimize processing of cell-contained substances, in particular DNA, for such purposes.

BRIEF SUMMARY

There is a need for particle-based or other solid phase systems and methods that efficiently obtain biological material. Such improved systems and methods may reduce the amount of time required to process a sample (i.e., a sample from which to obtain the biological material) and/or to increase throughput. Such may also increase the degree of thoroughness of obtaining the material, yielding greater amounts of material from a given sample size. There is also a need for systems and methods for lysis, capture and elution of biological material without separate processing of particles on which the biological material is captured. In particular, there is a need for such systems and methods that allow lysis, capture and elution of biological materials within the same system by simply controlling chemical composition and flow of reagents within the system. There is also a need for systems and methods to lyse cells without use of harsh reagents. Such may avoid wash steps during processing of biological material captured by particle-based systems. There is also a need for methods and formulations for more efficiently processing particle-bound or other solid phase-bound biological materials produced by standard methods known in the art. There is also a need for solid phase materials and methods for specific capture of cells or cell components. For example, there is a need for materials and methods for efficiently isolating and processing microorganisms having cell walls with high lipid content, such as *mycobacteria*. There is also a need for materials and methods for more efficient and effective removal of contaminating substances from biological materials isolated for further analysis. For example, there is a need for materials and methods to remove biological contaminants that may interfere with subsequent analysis or may otherwise limit the sensitivity of analysis of biological materials of interest, such as DNA. There is also a need for systems and methods that may allow sample heating integrated within a system.

There is also a need for systems and methods for specific capture of cell components. There is also a need for lysing equipment that is small and hence portable, and that is relatively inexpensive yet sufficiently robust to withstand travel or harsh operating environments.

A method of isolating nucleic acid may be summarized as including contacting a specimen containing a nucleic acid with a particulate material having an affinity for the nucleic acid to allow at least a portion of the nucleic acid to bind to the particulate material; and washing the particulate material having the bound nucleic acid with a low ionic strength zwitterion-containing buffer to yield a washed particulate material having the nucleic acid bound thereto. Contacting a specimen containing a nucleic acid with a particulate material may include contacting the specimen with a plurality of particles comprising at least one of a ceramic, a glass, a zirconia, a silica, a sand, or a metal core coated by a material that facilitates binding of the nucleic acid. The specimen may include a binding medium and contacting a specimen containing a nucleic acid with a particulate material may include contacting the specimen including the binding medium with the particulate material. The binding medium may include a composition that induces binding of the nucleic acid to the particulate material. The composition that may induce binding of the nucleic acid to the particulate material may include one or more of a salt concentration greater than or equal to 2 molar, a chaotropic substance, and an alcohol. Washing the particulate material with a low ionic strength zwitterion-containing buffer may include washing the particulate material with a low ionic strength zwitterion-containing buffer having a pH between about pH 3 and about pH 6. Washing the particulate material with a low ionic strength zwitterion-containing buffer may include washing the particulate material with a buffer comprising one or more of an amino acid, an aminosulfonic acid, or an aminocarboxylic acid. Washing the particulate material with a low ionic strength zwitterion-containing buffer may include washing the particulate material with a buffer comprising at least one zwitterionic substance having a pKa within a range between about 2 and about 4. The low ionic strength zwitterion-containing buffer may be a glycine buffer at about pH 4.

The method may further include applying to the washed particulate material a low ionic strength buffer having a pH that will adjust the pH at the surface of the particulate material above at least about 6 to elute the nucleic acid from the particulate material.

A formulation for use in isolating nucleic acid by a particulate material may be summarized as including a low ionic strength zwitterion-containing buffer having a pH less than about 6 to induce binding of nucleic acid to or to prevent release of bound nucleic acid from the particulate material. The low ionic strength zwitterion-containing buffer may have a pH between about 3 and about 6. The low ionic strength zwitterion-containing buffer may include a zwitterionic substance having a pKa between about 2 and about 4. The low ionic strength zwitterion-containing buffer may include a zwitterionic substance having a pKb between about 9 and about 11. The low ionic strength zwitterion-containing buffer may include a zwitterionic substance that is an amino acid, an aminosulfonic acid, or an aminocarboxylic acid. Low ionic strength zwitterion-containing buffer may be a glycine buffer having a pH about 4.

A kit for use in isolating nucleic acid may be summarized as including a particulate material that has an affinity for nucleic acid; a low ionic strength zwitterion-containing buffer having a pH less than about 6; and instructions for use of the kit to isolate nucleic acid. The low ionic strength zwitterion-containing buffer may have a pH between about 3 and about 6. The low ionic strength zwitterion-containing buffer may include a zwitterionic substance that is an amino acid, an aminosulfonic acid, or an aminocarboxylic acid.

A method of isolating phosphate-containing polyanions may be summarized as including contacting a specimen having a phosphate-containing polyanion with an amine-containing solid phase material having an affinity for the phosphate-containing polyanion to allow at least a portion of the phosphate-containing polyanion to bind to the solid phase material; and applying to the amine-containing solid phase material a formulation comprising phosphate-containing anions to elute the phosphate-containing polyanion from the amine-containing solid phase material. The phosphate-containing polyanion may be a nucleic acid and contacting a specimen having a phosphate-containing polyanion includes contacting the specimen having the nucleic acid present therein. The formulation including phosphate-containing anions may include one or more types of nucleoside phosphate. The formulation including phosphate-containing anions may include one or more types of nucleoside triphosphate. The one or more types of nucleoside triphosphate may include at least one of adenosine triphosphate, guanosine triphosphate, cytidine triphosphate, uridine triphosphate, deoxyadenosine triphosphate, deoxyguanosine triphosphate, deoxycytidine triphosphate, or deoxythymidine triphosphate. The solid phase material may include at least one of a particulate, a bead, a membrane, a flow channel, or a tube.

A kit for use in isolating phosphate-containing polyanions from a specimen may be summarized as including an amine-containing solid phase material having an affinity for phosphate-containing polyanions; a formulation having phosphate-containing anions; and instructions for use of the kit to isolate phosphate-containing polyanions from a specimen. The formulation may include one or more nucleoside phosphates. The formulation may include one of more nucleoside triphosphates. The formulation may include at least one of adenosine triphosphate, guanosine triphosphate, cytidine triphosphate, uridine triphosphate, deoxyadenosine triphosphate, deoxyguanosine triphosphate, deoxycytidine triphosphate, or deoxythymidine triphosphate. The amine-containing solid phase material may include at least one of a particulate, a bead, a membrane, a flow channel, or a tube.

A method of isolating a sulfonated polyanions may be summarized as including contacting a specimen having the sulfonated polyanion with an amine-containing solid phase material having an affinity for the sulfonated polyanion to allow at least a portion of the sulfonated polyanion to bind to the solid phase material; and applying to the amine-containing solid phase material a formulation comprising sulfate-containing anions to elute the sulfonated polyanion from the amine-containing solid phase material.

A kit for use in isolating sulfonated polyanions from a specimen may be summarized as including an amine-containing solid phase material having an affinity for sulfonated polyanions; a formulation having sulfate-containing anions; and instructions for use of the kit to isolate sulfonated polyanions from a specimen.

A method of capturing microorganisms having high cell wall lipid content may be summarized as including modifying a surface of a material to induce binding of microorganisms having a high cell wall lipid content; and contacting a specimen that contains microorganisms having the high cell wall lipid content with the material having the modified surface to capture the microorganisms having high cell wall lipid content on the modified surface of the material. Modifying a surface of a material to induce binding of microorganisms having a high cell wall lipid content may include reacting the surface of the material with one or more reagents to yield a hydrophobic surface.

The method may further include lysing the captured microorganisms having high cell wall lipid content to release nucleic acids from the captured microorganisms; and recovering the nucleic acids released from the captured microorganisms. Lysing the captured microorganisms may include lysing the microorganisms in a formulation having low to moderate ionic strength. Recovering the nucleic acids released from the captured microorganisms may include binding the nucleic acids to the material modified to induce binding of microorganisms and eluting the nucleic acids from the material. Modifying the surface of the material to induce binding of microorganisms having a high cell wall lipid content may include reacting the surface of the material with one or more reagents to yield a hydrophobic and positively charged surface. Reacting the surface of the material with one or more reagents to yield a hydrophobic and positively charged surface may include reacting the surface of the material with polydiallyldimethylammonium chloride.

The method may further include lysing the captured microorganisms having high cell wall lipid content to release nucleic acids from the captured microorganisms; and recovering the nucleic acids released from the captured microorganisms. Lysing the captured microorganisms may include lysing the microorganisms in a formulation containing one or more nucleoside triphosphates to limit binding of nucleic acids to the hydrophobic and positively charged surface of the material. Modifying the surface of the material to induce binding of microorganisms having a high cell wall lipid content may include reacting the surface of the material with one or more reagents to yield a hydrophobic and negatively charged surface. Contacting a specimen that contains microorganisms having a high cell wall lipid content with the surface of the modified material may include contacting the specimen with the surface in a formulation containing one or more of a high salt concentration, a low pH, and divalent cations.

The method may further include lysing the captured microorganisms having high cell wall lipid content to release nucleic acids from the captured microorganisms; and recovering the nucleic acids released from the captured microorganisms.

The method may further include washing the captured microorganisms in a formulation having low ionic strength to limit binding of nucleic acids to the hydrophobic and negatively charged surface of the material before the lysing. Modifying the surface of the material to induce binding of microorganisms having a high cell wall lipid content may include reacting the surface of the material with one or more silane reagents. Reacting the surface of the material with one or more silane reagents may include reacting the surface with at least one silane reagent selected from alkyl silanes, vinyl silanes, or amino silanes. The material having a surface modified to induce binding of microorganisms having high cell wall lipid content may include at least one of a particulate, a bead, a membrane, a flow channel, or a tube. The material having a surface modified to induce binding of microorganisms having high cell wall lipid content may include at least one of a ceramic, a glass, a silica, or a sand. The material having a surface modified to induce binding of microorganisms having high cell wall lipid content may include at least one of a gold particulate, a gold bead, a gold-coated particulate, or a gold-coated bead.

The method of may further include amplifying the recovered nucleic acids by an amplification reaction; and detecting the nucleic acids amplified by the amplification reaction. The microorganisms having high cell wall lipid content may include *mycobacteria*.

A solid phase material for binding microorganisms having high cell wall lipid content may be summarized as including a hydrophobic surface to induce binding of microorganisms having high cell wall lipid content. The hydrophobic surface may include a hydrophobic and positively charged surface. The hydrophobic and positively charged surface may include a coating comprising polydiallyldimethylammonium chloride. The hydrophobic surface may include a hydrophobic and negatively charged surface. The hydrophobic surface may include a surface modified by reaction with silane reagents. The hydrophobic surface may include a surface modified by reaction with silane reagents including at least one of alkyl silanes, vinyl silanes, and amino silanes. The hydrophobic surface may include a surface modified by reacting an amine-modified surface with a polymeric anhydride. The polymeric anhydride may be PA-18. The material may include at least one of a particulate, a bead, a membrane, a flow channel, or a tube. The material may include a mineral oxide modified to have a hydrophobic surface. The mineral oxide may be silica. The material may include gold modified to have a hydrophobic surface. The material may include at least one of a gold particulate, a gold bead, a gold-coated particulate, or a gold-coated bead.

The material may further include a monolayer coating on the surface comprising a hydrophobic thiol compound.

A kit for use in isolating microorganisms having high cell wall lipid content from a specimen may be summarized as including a solid phase material having a modified surface with an affinity for microorganisms that have a high cell wall lipid content; and instructions for use of the kit to isolate microorganisms having a high cell wall lipid content. The modified surface may include a hydrophobic surface, a hydrophobic and positively charged surface, or a hydrophobic and negatively charged surface. The hydrophobic and positively charged surface may include a coating comprising polydiallyldimethylammonium chloride. The modified surface may include a surface modified by reaction with a silane, an alkyl silane, a vinyl silane, or an amino silane. The modified surface may include a surface modified by reacting an amine-modified surface with a polymeric anhydride, including PA-18. The solid phase material having a modified surface may include at least one of a particulate, a bead, a membrane, a flow channel, or a tube. The solid phase material having a modified surface may include at least one of a mineral oxide, silica, or gold.

A method of obtaining biological material of interest may be summarized as including introducing a specimen containing a quantity of a biological material of interest into a chamber; and agitating the specimen in the chamber with a medium that includes a mixed population of particulate material and a fluid to mechanically lyse the specimen and to bind the biological material of interest to a particulate lysing material and secondary biological materials to a particulate secondary binding material; wherein the mixed population of particulate material includes the particulate lysing material and the particulate secondary binding material, the particulate lysing material having an affinity for the biological material of interest in the presence of the fluid, the particulate secondary binding material having an affinity for secondary biological materials other than the biological material of interest and a lateral dimension smaller than a lateral dimension of the particulate lysing material to allow selection of a mesh to selectively substantially pass the particulate secondary binding material and substantially block passage of the particulate lysing material; and wherein the fluid induces binding of the biological material of interest to the particulate lysing material. Agitating the specimen with a medium that includes a mixed population of particulate material may include agitating the specimen with a medium that includes the particulate lysing material and the particulate secondary binding material, each including a plurality of beads. Agitating the specimen with a medium that includes a mixed population of particulate material may include agitating the specimen with a medium that includes the particulate lysing material, the particulate lysing material including at least one of a plurality of ceramic beads, a plurality of glass beads, a plurality of zirconia (e.g., zirconium) beads, a plurality of silica beads, a plurality of sand, or a plurality of beads with a metal core coated by a material that facilitates binding of the biological material of interest. Agitating the specimen with a medium that includes a mixed population of particulate material may include agitating the specimen with a medium that includes the particulate secondary binding material, the particulate secondary binding material including at least one of a plurality of ceramic beads, a plurality of glass beads, a plurality of zirconia (e.g., zirconium) beads, a plurality of silica beads, a plurality of sand, or a plurality of beads with a metal core coated by a material that facilitates binding of the secondary biological material. Obtaining a biological material of interest may include obtaining a nucleic acid. Agitating the specimen with a medium that includes a mixed population of particulate material to bind secondary biological materials may include agitating the specimen to bind biological materials that interfere with binding of the biological material of interest by the particulate lysing material. Agitating the specimen with a medium that includes a mixed population of particulate material to bind secondary biological materials may include agitating the specimen to bind biological materials that interfere with subsequent reactions with and analysis of the biological material of interest. Agitating the specimen with a medium that includes a mixed population of particulate material to bind secondary biological materials may include agitating the specimen to bind lipids and lipid-like materials, proteins, polypeptides and polysaccharides. Agitating the specimen with a medium that includes a mixed population of particulate material may include agitating the specimen with a medium that includes particulate secondary binding material modified to include one or more agents to bind and remove from specimen lysate particular secondary biological materials. Agitating the specimen with a medium that includes a mixed population of particulate material may include agitating the specimen with a medium that includes particulate secondary binding material modified to include one or more of Protein A, Protein G, or Protein L to bind and remove immunoglobulins; anti-albumin antibody to bind and remove albumin; concanavalin A to bind and remove glycosylated proteins; or titanium dioxide to bind and remove phosporylated proteins. Agitating the specimen with a medium that includes a mixed population of particulate material may include agitating the specimen with a medium that includes paramagnetic particulate secondary binding material. Agitating the specimen with a medium that includes a mixed population of particulate material may include agitating the specimen with a medium that includes particulate secondary binding material to bind and remove secondary biological material before lysis of the specimen containing the biological material of interest. Agitating the specimen with a medium that includes a mixed population of particulate material may include agitating the specimen with a medium that includes particulate secondary binding material to bind and remove secondary biological material for later elution and analysis.

The method may further include providing a filter having passages sized to substantially prevent passage of the particulate lysing material and substantially pass the particulate secondary binding material; and flowing a mixture of the agitated, lysed specimen with the fluid and the mixed population of particulate material through the filter.

A kit for use in obtaining biological material of interest may be summarized as including a mixed population of particulate material including a particulate lysing material and a particulate secondary binding material, the particulate lysing material having affinity for the biological material of interest, the particulate secondary binding material lacking affinity for the biological material of interest and having a size smaller than that of the particulate lysing material; and instructions for use of the kit to obtain biological material of interest. Each of the particulate lysing material and the particulate secondary binding material may include a plurality of beads. The particulate lysing material may include at least one of a plurality of ceramic beads, a plurality of glass beads, a plurality of zirconia beads, a plurality of silica beads, a plurality of sand, or a plurality of beads with a metal core coated by a material that facilitates binding of the biological material of interest. The particulate secondary binding material may include at least one of a plurality of ceramic beads, a plurality of glass beads, a plurality of zirconia beads, a plurality of silica beads, a plurality of sand, or a plurality of beads with a metal core coated by a material that facilitates binding of the secondary biological material. The particulate secondary binding material may include one or more agents to bind and remove from specimen lysate particular secondary biological materials. The particular secondary binding material may include one or more of Protein A, Protein G, or Protein L to bind and remove immunoglobulins; anti-albumin antibody to bind and remove albumin; concanavalin A to bind and remove glycosylated proteins; or titanium dioxide to bind and remove phosporylated proteins. At least a portion of the particulate secondary binding material may be paramagnetic.

The kit may further include a filter having passages sized to substantially prevent passage of the particulate lysing material and substantially pass the particulate secondary binding material.

A system to lyse specimens and isolate biological materials of interest may be summarized as including a chamber to receive a specimen containing the biological material of interest; a medium that includes a mixed population of particulate material and a fluid; and an agitator selectively operable to agitate the specimen in the chamber along with the medium that includes the mixed population of particulate material; and wherein the mixed population of particulate material includes a particulate lysing material and a particulate secondary binding material, the particulate lysing material having an affinity for the biological material of interest in the presence of the fluid, the particulate secondary binding material having an affinity for secondary biological materials other than the biological material of interest and a lateral dimension smaller than a lateral dimension of the particulate lysing material to allow selection of a filter to selectively substantially pass the particulate secondary binding material and substantially block passage of the particulate lysing material; and wherein the fluid induces binding of the biological material of interest to the particulate lysing material. Each of the particulate lysing material and the particulate secondary binding material may include a plurality of beads. The particulate lysing material may include at least one of a plurality of ceramic beads, a plurality of glass beads, a plurality of zirconia beads, a plurality of silica beads, a plurality of sand, or a plurality of beads with a metal core coated by a material that facilitates binding of the biological material of interest. The particulate secondary binding material may include at least one of a plurality of ceramic beads, a plurality of glass beads, a plurality of zirconia beads, a plurality of silica beads, a plurality of sand, or a plurality of beads with a metal core coated by a material that facilitates binding of the secondary biological material. The particulate secondary binding material may include at least one agent to bind and remove from specimen lysate particular secondary biological materials. The particulate secondary binding material may include at least one of Protein A, Protein G, or Protein L to bind and remove immunoglobulins; anti-albumin antibody to bind and remove albumin; concanavalin A to bind and remove glycosylated proteins; or titanium dioxide to bind and remove phosporylated proteins. At least a portion of the particulate secondary binding material may be paramagnetic.

The system may further include a filter having a mesh size to retain the particulate lysing material and to pass the particulate secondary binding material.

A method of capturing a biological material may be summarized as including introducing a fluid specimen containing the biological material into a chamber of a device, the chamber containing a solid phase material that has an affinity for the biological material, the device having a fitting attached to the chamber, the fitting having a thin filter insert that retains the solid phase material while allowing rapid flow of the fluid specimen through the filter insert; and flowing the fluid specimen containing the biological material through the particulate at low pressure and rapid rate, the fluid specimen exiting the device via the filter insert. Introducing a fluid specimen into the chamber of a device may include introducing the specimen into a chamber containing a solid phase material having an affinity for at least one of a nucleic acid, a protein, a polypeptide, a His-tagged protein, a His-tagged polypeptide, a lipid-containing biological material, a glycosylated protein, a phosphorylated protein, or a microorganism having a high cell wall lipid content. Introducing a fluid specimen into the chamber of a device may include introducing the specimen into a chamber containing a solid phase material having an affinity for more than one biological material. Introducing a fluid specimen into the chamber of a device may include introducing the specimen into a chamber containing a solid phase material comprising the solid phase material is a particulate or a bead. Introducing a fluid specimen into the chamber of a device may include introducing the specimen into a chamber containing a solid phase material comprising a particulate or bead having a diameter or lateral dimension of at least 200 µm. Introducing a fluid specimen into the chamber of a device having a fitting having a filter insert may include introducing the specimen into a device having a filter insert of pore size between about 10 µm and about 200 µm and more preferably between about 10 µm and about 200 µm and more preferably between about 40 µm and about 80 µm. Introducing a fluid specimen into the chamber of a device having a fitting having a filter insert may include introducing the specimen into a device having a filter insert with a thickness between about 0.002" and about 0.003". Introducing a fluid specimen into the chamber of a device having a fitting having a filter insert may include introducing the specimen into a device having a wire mesh insert. Introducing a fluid specimen into the chamber of a device having a fitting having a wire mesh insert may include introducing the specimen into a device having a stainless steel mesh insert.

The method may further include eluting the biological material captured on the solid phase material by flowing an elution medium through the solid phase at low pressure and uninhibited flow; and collecting an effluent containing the biological material, the effluent exiting the device via the filter insert.

A device for capturing a biological material from a fluid specimen at high flow rate and low operating pressure may be summarized as including a chamber containing a solid phase material that has an affinity for the biological material; and a fitting attached to the chamber, the fitting having a thin filter insert that retains the solid phase material while allowing rapid flow of the fluid specimen at low pressure. The solid phase material may have an affinity for at least one of a nucleic acid, a protein, a polypeptide, a His-tagged protein, a His-tagged polypeptide, a lipid-containing biological material, a glycosylated protein, a phosphorylated protein, or a microorganism having a high cell wall lipid content. The solid phase material may have an affinity for more than one biological material. The solid phase material may be a particulate or a bead. The particulate or bead may have a diameter or lateral dimension of at least about 10 µm and more preferably about 100 µm. The filter insert may have a pore size between about 10 µm and about 200 µm and more preferably between about 40 µm and about 80 µm. The filter insert may have a thickness between about 0.002" and about 0.003". The filter insert may be a wire mesh insert. The wire mesh insert may be stainless steel.

A method for removing fluid containing particulate matter from a chamber or a container may be summarized as including attaching a pipette tip to a pipette or a syringe, the pipette tip having a filter or mesh material at least proximate an end of the pipette tip; inserting the end of the pipette tip having the filter or mesh material into the chamber or container holding the fluid containing the particulate matter; and withdrawing fluid from the chamber or container into the pipette tip through the filter or mesh. The filter or mesh material may be removable from or replaceable on the pipette tip.

A device for removing fluid containing particulate matter from a chamber or container may be summarized as including a pipette tip having a filter or mesh material at least proximate an end of the pipette tip.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIG. 1B is a front, right side, top isometric view of the apparatus of FIG. 1A.

FIG. 2B is a front, right side, top isometric view of the apparatus of FIG. 2A.

FIG. 3 is a front, right side isometric view of a motor and drive mechanism of the apparatus of FIGS. 1A-2C.

FIG. 11 is a flow diagram of a method of evacuating lysed material in a flow-through lysing system such as that of FIG. 4, according to one illustrated embodiment.

FIG. 12 is a flow diagram of a method of evacuating lysed material in a flow-through lysing system such as that of FIG. 4, according to another illustrated embodiment.

FIG. 13 is a method of pumping material to be lysed in a flow-through lysing system such as that of FIG. 4, according to a further illustrated embodiment.

FIG. 14 is a flow diagram of a method of pumping material to be lysed in a flow-through lysing system such as that of FIG. 4, according to still a further illustrated embodiment.

FIG. 15 is a method of operating a flow-through lysing system such as that of FIG. 4 to analyze lysed material, according to one illustrated embodiment.

FIG. 24 is a flow diagram of a method of operating an impeller of a lysing system such as that of FIG. 16, 17 or 18, according to one illustrated embodiment.

FIG. 25 is a flow diagram of a method of operating an impeller of a lysing system such as that of FIG. 16, 17 or 18, according to one illustrated embodiment.

FIG. 26 is a flow diagram of a method of replacing a micromotor of a lysing system such as that of FIG. 16, 17 or 18, according to one illustrated embodiment.

FIG. 27 is a flow diagram of a method of operating a lysing apparatus such as that of FIG. 18, according to one illustrated embodiment.

FIG. 34A is a schematic diagram of a bidirectional flow system for lysing, capture and elution including a sample and elution module, a lysing module, a syringe pump, and a heater, according to one illustrated embodiment.

FIG. 34B is a schematic diagram showing valve positions in the sample and elution module during operation of the system in the embodiment of FIG. 34A.

FIG. 36 is a plan view of a plurality of lysing apparatus coupled sequentially to one another, according to one illustrated embodiment.

FIG. 38A is a side elevational view of a stopcock style lysing device, according to one illustrated embodiment, showing an inner portion rotated or configured to provide a first flow path via two selected ports.

FIG. 38B is a side elevational view of the stopcock style lysing device of FIG. 38A, showing the inner portion rotated or configured to provide a second flow path via two selected ports.

FIG. 39A is an exploded isometric view of a stopcock style lysing device, according to one illustrated embodiment, showing an inner vessel having an open bottom portion, the inner vessel in a first orientation with respect to an outer vessel.

FIG. 39C is an isometric view of the inner vessel of FIG. 39A, showing the inner vessel in a second orientation, different from the orientation illustrated in FIG. 39A.

DETAILED DESCRIPTION

Figure 2A:
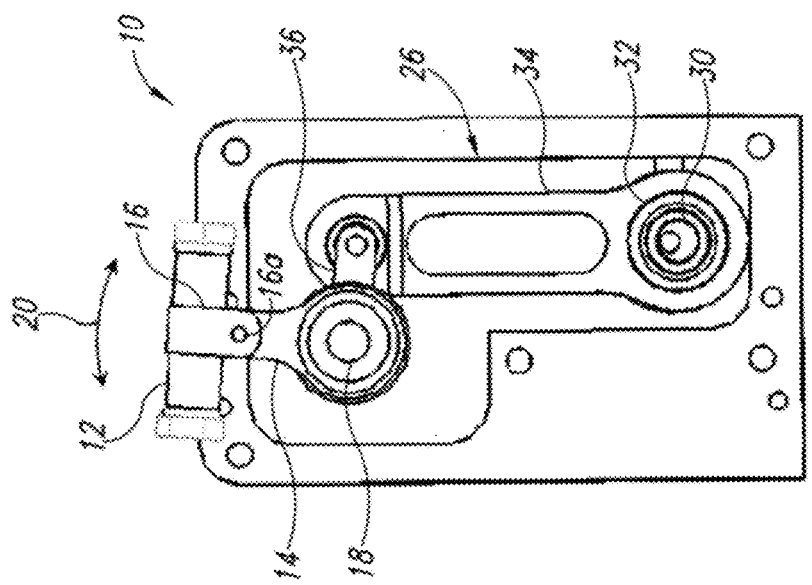
FIG. 2A is a front elevational view of the apparatus of FIG. 1A with a front cover removed, according to one illustrated embodiment.
Figure 1A:
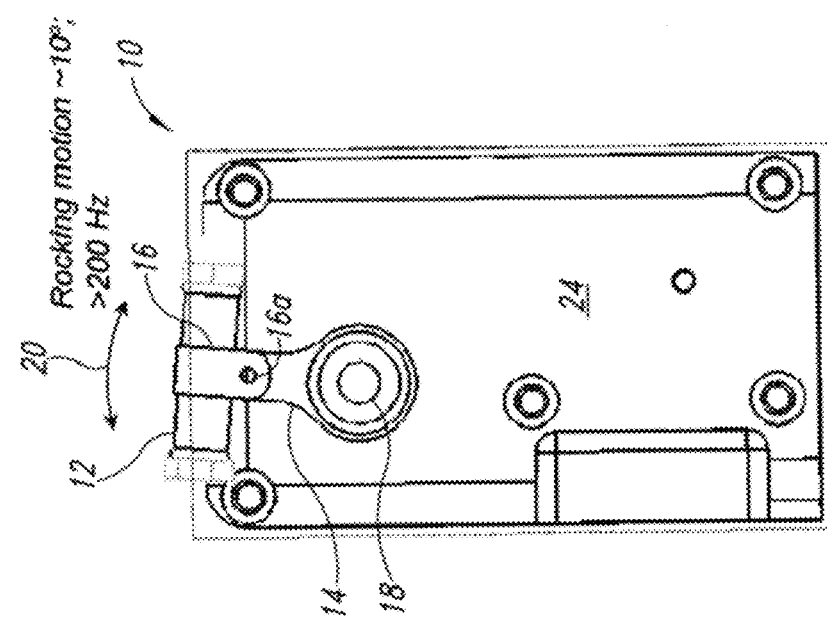
FIG. 1A is a front elevational view of an apparatus to perform material lysis, according to one illustrated embodiment.
Figure 2C:
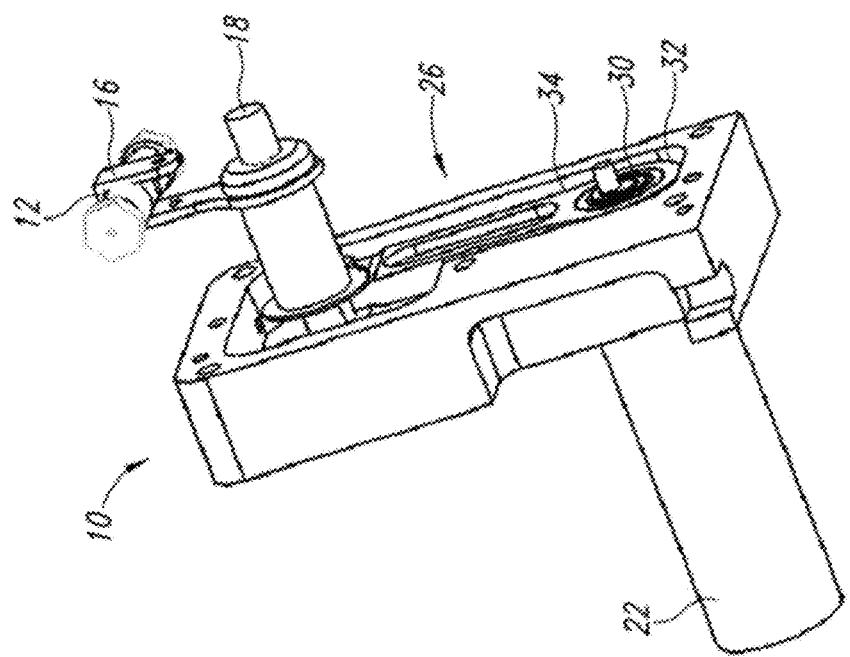
FIG. 2C is a front, right side, bottom isometric view of the apparatus of FIG. 2A.
Figure 1C:
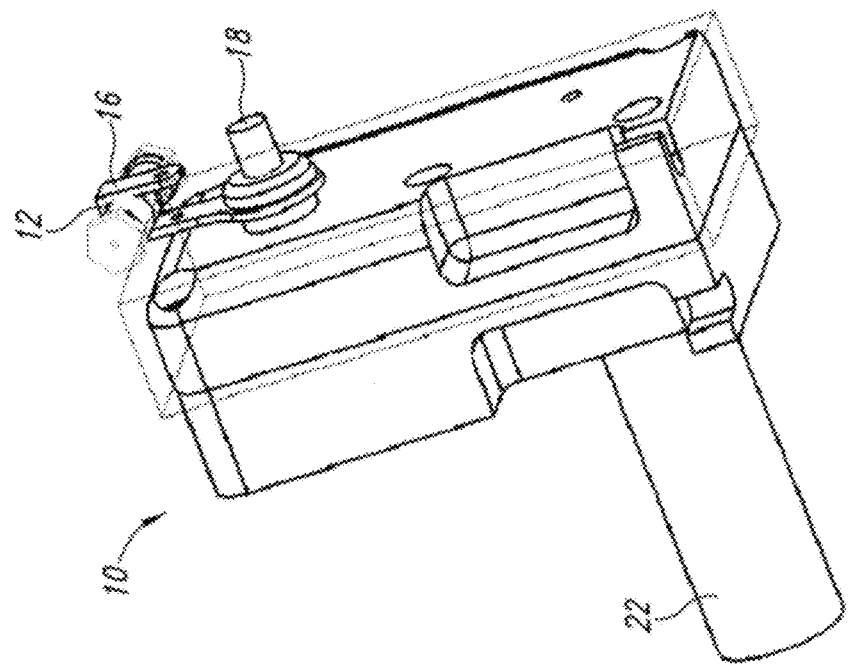
FIG. 1C is a front, left side, bottom isometric view of the apparatus of FIG. 1A.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with micromotors, controllers including motor controllers, and control systems such as programmed general purpose computing systems and the like have not been shown or described in detail to avoid unnecessarily obscuring descriptions of the embodiments. In other instances, methods commonly known for use with and manipulation of nucleic acids, proteins, polypeptides, and other biological materials have not been described as they would be readily available to those of ordinary skill in the art of such materials. Such common methods include, for example, PCR and heat denaturation of DNA.

Unless the context requires otherwise, throughout the specification and claims which follow, the word "comprise" and variations thereof, such as, "comprises" and "comprising" are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

A number of embodiments of lysis apparatus, systems and methods of use are described herein. The lysis apparatus and systems perform lysis on a material to be lysed using lysing particulate material, to produce lysed material or material that has been lysed. The material to be lysed may take the form of biological materials, for example cells, spores, tissue, yeast, fungi, plants, bacteria, etc., typically suspended in a liquid medium. The lysing particulate material may take a variety of forms. While often referred to herein as beads, the term bead is not meant to be limiting with respect to size or shape. The beads may, for example, comprise ceramic, glass, zirconia, zirconia/silica, zirconium silicate, metal, plastic, nickel, tungsten, tungsten carbide. Yttrium stabilized zirconia, sand, and/or particles of any geometry such as shard or of random shape. The lysed material may likewise take a variety of forms, for example nucleic acids, polypeptides, proteins, organelles-nuclei, mitochondria, lysosomes, chloroplasts, endoplasmic reticulum, etc.

Various embodiments of the material separation and/or lysis apparatus and systems may, for example, operate in: 1) a batch mode, 2) flow-through stop or semi-batch mode, or 3) continuous flow-through mode. In batch mode, a container having a chamber holding a sample of material to be lysed is located in a holder and oscillated. The container is removed after sufficient oscillation and the lysed material is recovered. In the flow-through stop or semi-batch mode, a sample of material to be lysed flows into to fill the chamber. The container is then oscillated until sufficiently lysed. The chamber is evacuated of the lysed material. In the flow-through mode, a sample of material to be lysed flows through the chamber of the container during oscillation at a desired flow rate, providing a desired or defined residence time within the chamber. In the flow-through stop or semi-batch mode, the sample may be abutted by an immiscible liquid or gas and the chamber may be evacuated by a blast of a fluid, for example a liquid or a gas.

At least some of the embodiments take advantage of the understanding that the forces responsible for mechanical rupture of biological samples scale with the oscillation frequency squared, and that by employing relatively small sample sizes, the various embodiments described herein can achieve relatively higher frequencies than commercially available apparatus, resulting in rapid and efficient lysis.

A number of embodiments of systems and methods for extraction, capture and elution of biological materials, in particular nucleic acids such as DNA, are described herein. Biological specimens, such as cells or viruses, may be lysed by mechanical disruption in a lysing chamber containing particulate material, for example beads made from silica and/or zirconia. The volume of the lysing chamber may be crowded with the particulate material. The particulate material in the lysing chamber may be driven rapidly by an impeller connected to a small motor to lyse the biological specimens. The motor may be disposable. Alternatively, the lysing chamber may be oscillated to drive the particulate material to lyse the biological specimens. Further, treatment of the contents of the lysing chamber may include ultrasonic treatment. Such different types of mechanical disruption allow lysis to occur without the use of harsh chemicals, such as chaotropic agents. In comparison to standard procedures for preparation of biological materials, the procedures disclosed herein may save time by eliminating wash steps that are typically included to remove harsh chemicals. Chemical conditions within the lysing chamber may be controlled during lysis to allow simultaneously lysis of the biological specimen and binding or collection of the biological material released by lysis, e.g., DNA or protein or both, on the particulate material. The apparatus or system may then be operated to alter chemical and/or flow conditions within the lysing chamber to elute the biological material of interest from the particulate material. The systems and methods disclosed herein thus advantageously allow simple, efficient approaches to lysis, capture and elution of biological materials from biological specimens. The surprisingly advantageous approaches involve appropriately timed, simple control of flow direction and chemical compositions of fluids within a lysing system. The biological material, e.g., DNA, may then be subjected to testing or analysis or used for other purposes. The absence of harsh reagents during lysis may not only save time but also yield materials that are more suitable for use in subsequent procedures. Thus, the disclosed systems and methods provide rapid and efficient lysis of specimens, e.g., cells, and capture of biological materials, e.g., DNA, in a single chamber by sequential use of fluids having chemical compositions particularly appropriate for lysis, capture and elution. Various specific embodiments will now be discussed.

Figure 4:
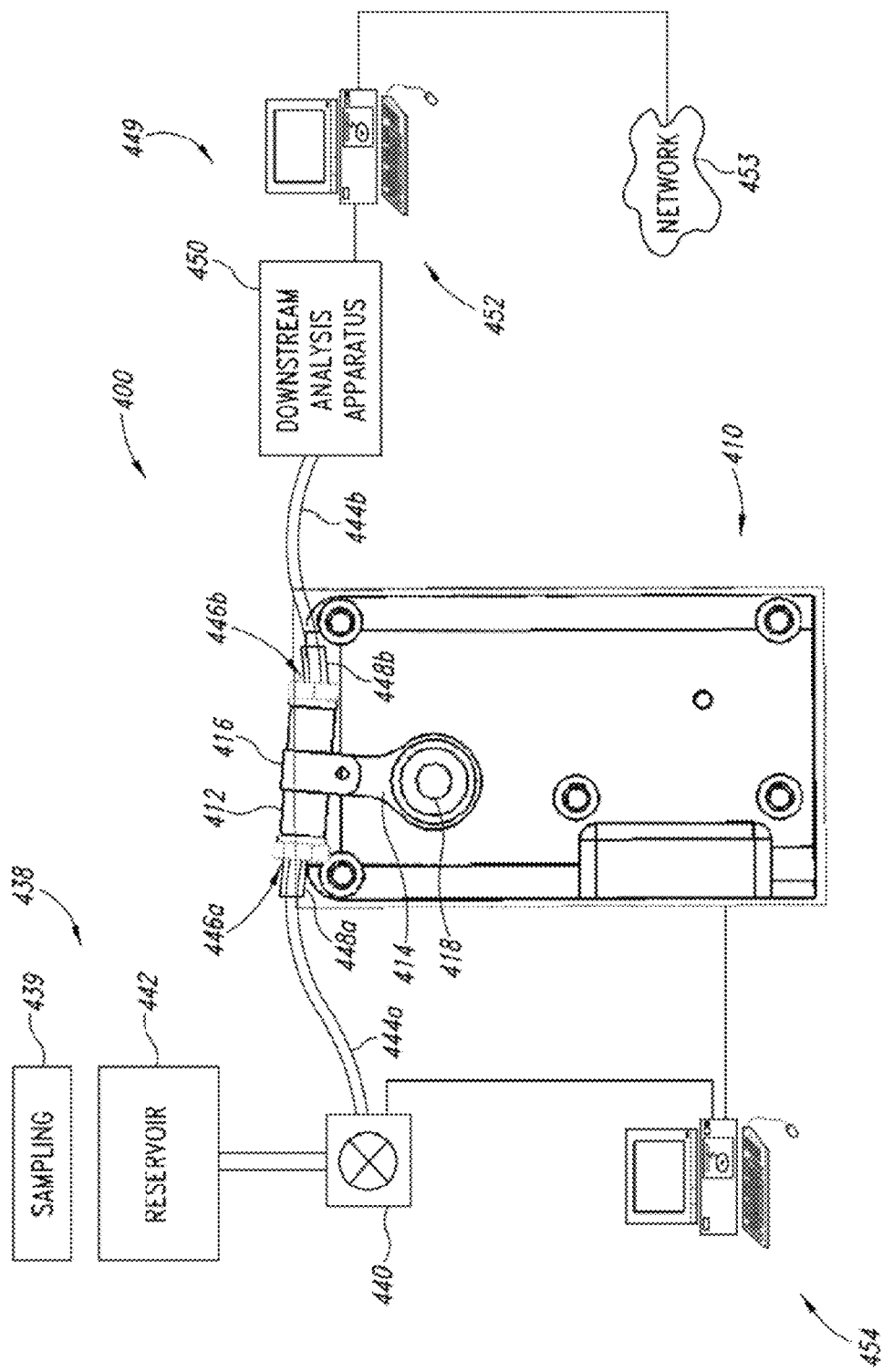
FIG. 4 is a schematic view of a system to perform flow-through processing, including an apparatus to perform material lysis, an upstream subsystem to provide material to be lysed, a downstream subsystem to analyze material that has been lysed, and a control subsystem, according to one illustrated embodiment.

FIGS. 1A-1C and 2A-2C show an apparatus 10 operable to perform lysing on a material to be lysed contained in a container 12, according to one illustrated embodiment. In some embodiments, off-the-shelf vials and tubes may be employed as the container 12 to hold specimens of material to be lysed and the lysing particulate material or other material, for example PCR or Eppendorf tubes. While illustrated in FIGS. 1A-1C and 2A-2C in a batch mode, the lysis apparatus 10 may be used in a flow-through stop or semi-batch mode or in a continuous mode as illustrated in FIG. 4.

The container 12 may be removably coupled to an arm 14 via a holder 16. The holder 16 may take a variety of forms. For example, the holder 16 may take the form of a U-shaped clamp or other member. The holder 16 may include a fastener (e.g., screw, bolt, etc.) 16a operable to secure the holder 16 in a container securing configuration. Alternatively, the holder 16 may be resilient and biased into the container securing configuration.

The arm 14 may be coupled to pivot about an axle 18 such that the container 12 oscillates along an arcuate path 20. Oscillation along an arcuate path 20 achieves confined periodic flow fields with angular accelerations that provide strong particulate flow fields and large shear rates between beads in a liquid solution or slurry. Experiments by the applicants have demonstrated that miniaturized geometries can provide superior lysis through the application of high frequencies (e.g., greater than approximately 100 Hz). Since the relative forces on non-neutral density beads in a liquid scale according to $\omega^2 r$, where $\omega$ represents angular velocity and r is the distance of a bead from the center of rotation, a small increase in angular speed can allow for a substantial decrease in size to attain similar performance. Linear oscillatory motions, even at high frequencies result in little lysis of biological samples, while those with an arc motion may achieve lysis that is superior to commercially available bead-based lysis apparatus. High-speed movies clearly show that linear motions result in periodic concentration of beads followed by expansion of beads away from one another, but relatively little relative motion of beads that is not along the axis of motion. In contrast, where a container oscillates in an arc, the beads are seen to compress to higher density just as a strong swirl is induced, resulting in very effective lysing. Collisions and shearing provided by the relative motion of the suspended beads contribute to the high efficiency of the lysing.

The arm 14 may be a rigid arm, i.e., an arm that does not appreciably bend during oscillation with a load having a mass at least roughly equivalent to an expected load of a container containing a material to be lysed and a lysing particulate material. Alternatively, the arm 14 may be a flexible arm, i.e., an arm that does appreciably bend during oscillation with a load having a mass at least roughly equivalent to an expected load of a container containing a material to be lysed and optionally a lysing particulate material.

As best illustrated in FIGS. 2A-2C and 3 in which a cover plate 24 is removed, the arm 14 may be driven via a motor 22 and a drive mechanism 26, which may take the form of a four-bar linkage. In particular, a shaft 28 of the motor 22 drives a first member such as a bar, here in the form of eccentric cam 30. The eccentric cam 30 is received in a bore 32 of a second member or connecting arm 34. The connecting arm 34 is drivingly coupled to the holder 16 by the axle 18 of a rocker arm 36. The drive mechanism 26 provides a low cost, reliable mechanism to realize relatively high frequency oscillatory motion along the arcuate path 20. While such frequencies may not be considered high for other types of devices, of instance rotating devices or ultra-sonic devices, such frequencies are considered high oscillating type devices.

FIG. 4 shows a flow-through lysis system 400 according to one illustrated embodiment. As described in more detail herein, the flow-through lysis system 400 may be operated in a flow-through stop or semi-batch mode, or in a continuous flow mode.

The flow-through system 400 includes a lysing apparatus 410 and a container 412, which may be similar to those described in previous embodiments. For example, the lysing apparatus 410 may include an arm 414 and holder 416 to hold the container 412 as the container pivotally oscillates about an axle 418.

The flow-through lysis system 400 may include an upstream subsystem 438 to deliver material to be lysed. For example, the upstream subsystem 438 may include a pump 440 operable to pump or otherwise deliver material to be lysed to the container 412. The upstream subsystem 438 may also include a reservoir 442 that holds the material to be lysed.

The upstream subsystem 438 may additionally or alternatively include a mechanism to collect material to be lysed, for example a sampling apparatus 439. The sampling apparatus 439 may be manually operated or may be automatic. The sampling apparatus 439 may, for example, sample the ambient environment, for example the air or atmosphere, water or fluids, soil or other solids. The sampling apparatus 439 may include a vacuum or mechanism to create a negative pressure to extract a sample. The sampling apparatus 439 may include an actuator, for example an arm with a shovel or broom to retrieve samples. The sampling apparatus may include an actuator, for example a needle and syringe to example samples.

The material to be lysed may be delivered via one or more conduits, for example, a tube 444a to an entrance 446a of the container 412. The tube 444a may be reinforced at one or both ends, for example, being reinforced with multiple layers of concentrically arranged tubes 448a. The tube 444a may have a length $L_1$ that is sufficiently long to allow the container 412 and arm 414 to oscillate, while being sufficiently short as to prevent resonance in the tube. The length $L_1$ would be a function of the density, the rigidity, or the attachment method of the tube 444a as well as the density, mass and/or rigidity of any material to be lysed carried therein.

The flow-through lysis system 400 may further include a downstream analysis subsystem 449. The downstream analysis subsystem 449 may include one or more downstream analysis apparatus 450. The downstream analysis apparatus 450 may take any of a variety of forms. For example, the downstream analysis apparatus 450 may include a nucleic acid amplification instrument, electron-microscope, western blotting apparatus, mass spectrometer, gas chromatograph, etc.

The downstream analysis subsystem 449 may further include one or more computing systems 452 communicatively coupled to the downstream analysis apparatus 450. The computing system 452 may be coupled to one or more networks 453, for example a local area network (LAN), a wide area network (WAN) such as the Internet, and/or a wireless wide area network (WWAN). The computer system 452 may provide information about the results of an analysis performed on lysed material via the network 453. For example, the computing system 452 may automatically provide an alert or other message to suitable system based on the results of the analysis. Such may, for example, be used to provide an alert when a toxic or dangerous substance or condition is detected.

The downstream analysis apparatus 450 may be fluidly communicatively coupled to an exit 446b of the container 412 via one or more conduits, for example, tube 444b. The tube 444b may be reinforced at one or both ends, for example, by one or more concentrically arranged lengths of tube 448b. The tube 444b may have a length $L_2$ that is sufficiently long as to allow the container 412 and arm 414 to oscillate freely while being sufficiently short as to prevent resonance of the tube 444b. The length $L_2$ may be based on the density, the rigidity, or the attachment method of the tube 444b as well as a density, mass and/or rigidity of any material carried therein.

The flow-through lysis system 400 may further include one or more control systems 454. The control system 454 may take the form of one or more motor controllers and/or computing systems. The control system 454 may be configured to operate the flow-through system 400 in a flow-through stop or semi-batch mode and/or in a flow-through continuous flow mode. The control systems 454 may, for example, be communicatively coupled to control the lysing apparatus 410 and/or pump 440.

The flow-through system 400 provides a number of advantages over batch based apparatus. For example, some types of beads may have an affinity for certain bio-products that are released on lysis, so some of the cell contents may be "lost" due to adsorption on the bead surfaces. The flow-through design may advantageously automatically elute the adsorbed biomolecules. It also avoids difficult or additional acts that may be required in batch mode configurations to evacuate the chamber. For example, the flow-through embodiments may eliminate any possible need to blast the chamber with a fluid such as air to clear the chamber of the lysed material.

Figure 5:
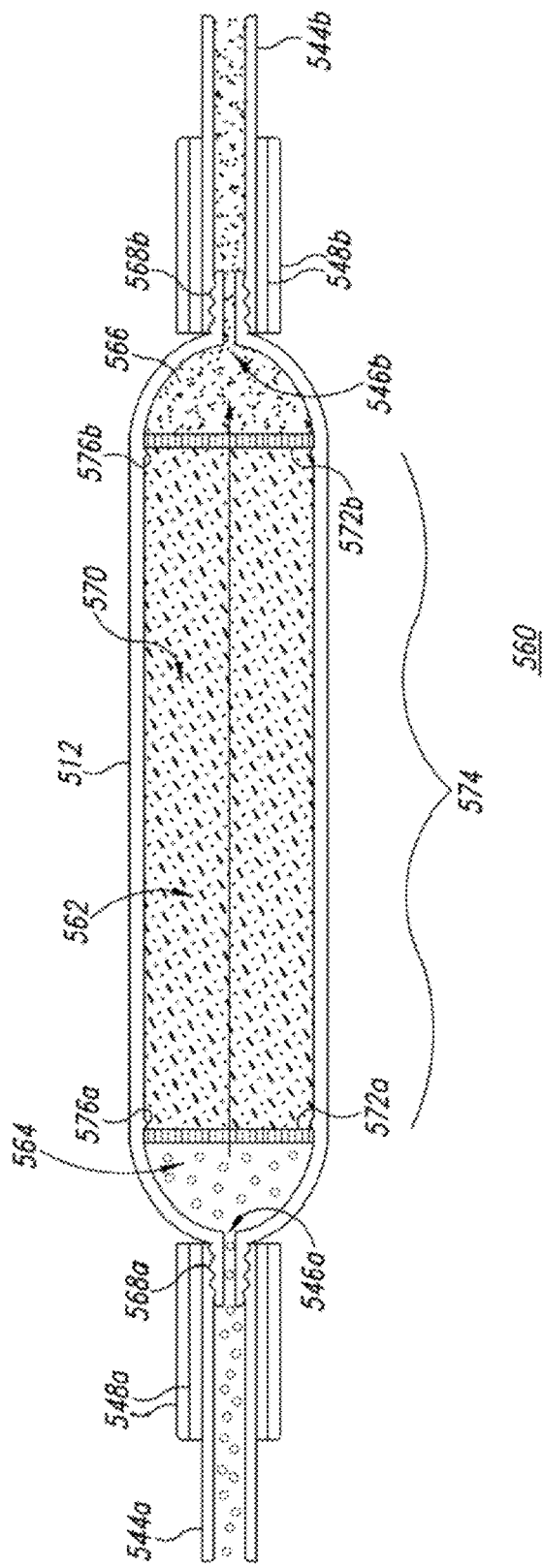
FIG. 5 is a cross-sectional view of a container having a chamber that houses material to be lysed, particulate lysing material, and material that has been lysed, according to one illustrated embodiment particularly useful in flow-through lysing.

FIG. 5 shows a container 512 according to one illustrated embodiment.

The container 512 may have an entrance 546a to provide fluid communication from an exterior 560 of the container to a chamber 562 of the container 512. The container 512 may include an exit 546b providing fluid communication between the exterior 560 and the chamber 562 of the container 512. A first tube 544a may be coupled to the container 512 to provide material to be lysed 564 to the chamber 562 via the entrance 546a. As noted previously, the tube 544a may be reinforced, for example, with one or more layers of concentrically arranged tubing 548a. A second tube 544b may be coupled to the container 512 via the exit 546b to remove lysed material 566 via the exit 546b. In some embodiments, the container 512 may include attachment structures to attach or otherwise couple or secure the tubes 544a, 544b. For example, the container 512 may include a ribbed nipple 568a at the entrance 546a and/or a ribbed nipple 568b at or proximate the exit 546b.

The container includes lysing material 570. The lysing material 570 may take a variety of forms, for example, a plurality of beads. The beads may take a variety of forms including one or more of ceramic beads, glass beads, zirconia beads, zirconia/silica beads, metal beads, plastic beads, sand, and/or metal beads that are coated with a bio-affinity material or receptor, such as a sequence specific probe or an antibody. The beads may have a variety of diameters, for example, between approximately 10 microns and approximately 600 microns.

In the flow through embodiments, the container 512 may include a first filter 572a positioned relatively proximate the entrance 546a and a second filter 572b positioned relatively proximate the exit 546b. The first and second filters 572a, 572b form a particulate retainment area 574 in which the lysing particulate material 570 is retained. In particular, the filters 572a, 572b may have a plurality of openings sized to substantially pass the material to be lysed 564 and the lysed material 566, respectively, while blocking the particulate lysing material 570. The container 512 may include one or more structures, for example, tabs or annular ridges 576a, 576b to retain the first and second filters 572a, 572b in place. Filters may, for example take the form of nylon or stainless steel mesh filter.

Many of the embodiments include chambers which have multiple openings and which include filters of mesh to retain particulates in the chamber. In some embodiments it is advantageous to use filters having different pore sizes for different chamber openings. For example, a filter at the opening where sample enters the chamber may have a larger pore size to facilitate the entry of cells or particles of tissue while a filter at the opening which serves as an exit to the chamber may have a filter with a smaller pore size to retain the cells or particles of tissue within the chamber. This embodiment would, for example, retain large cells in the chamber of a lysis device until the cells are effectively lysed.

The embodiments of FIGS. 1A-5 may advantageously allow extremely high packing densities. In these embodiments, the volume of particulate material may advantageously exceed the volume of material to be lysed or may exceed the volume of material that has been lysed. Additionally or alternatively, these embodiments may advantageously have essentially no air in the chamber. As used herein, essentially no air means that the chamber is free of air other than small bubbles which may be unintentionally entrapped in the chamber. Such may increase lysing efficiency and prevent undesirable heating of the system from friction associated with liquid-air contact line motions.

Figure 6:
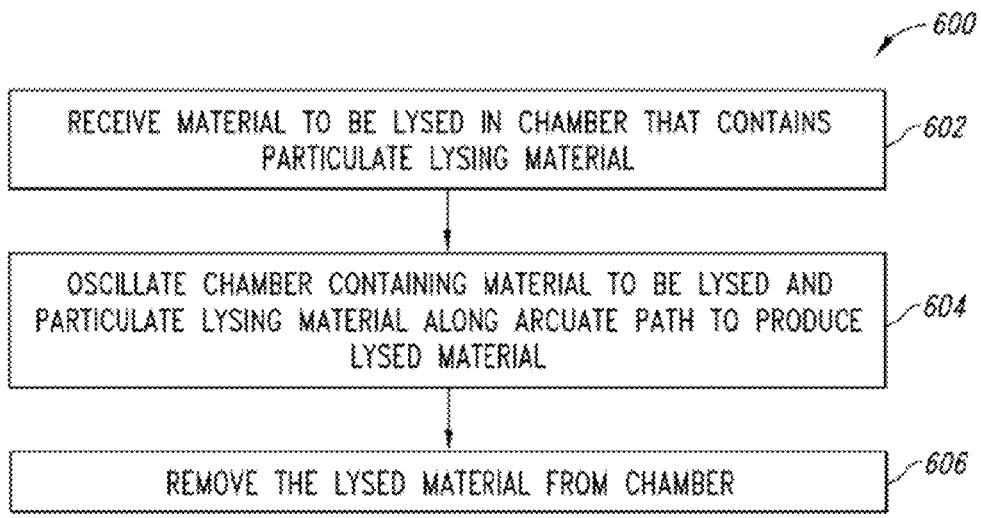
FIG. 6 is a flow diagram of a method of operating an apparatus, such as the apparatus of FIGS. 1A-4, to perform lysing.

FIG. 6 shows a method 600 of operating an apparatus such as that illustrated in FIGS. 1A-4 to lyse material, according to one illustrated embodiment.

At 602, material to be lysed is received in the chamber of the container. The chamber may already hold lysing particulate material. At 604, the container is oscillated along an arcuate path. The oscillation produces large variations in movement between respective ones of the lysing particulate material. Such variations are more pronounced than in translational or rotational movements. At 606, the lysed material is removed from the chamber of the container.

Figure 7:
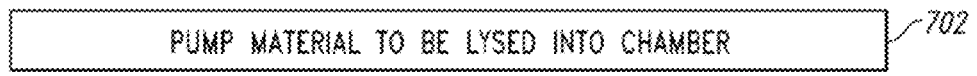
FIG. 7 is a flow diagram of a method of pumping material to be lysed in a flow-through lysing system such as that of FIG. 4 according to one embodiment.

FIG. 7 shows a method 700 of pumping material to be lysed in a flow-through lysing system such as the one of FIG. 4, according to one illustrated embodiment.

At 702, the material to be lysed is pumped into the chamber of the container.

Figure 8:
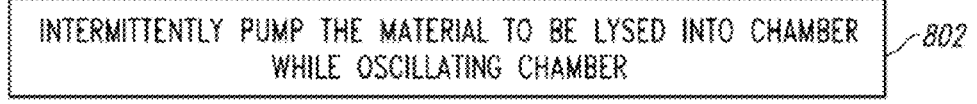
FIG. 8 is a flow diagram of a method of pumping material to be lysed in a flow-through lysing system such as that of FIG. 4, according to another illustrated embodiment.

FIG. 8 shows a method 800 of pumping material to be lysed in a flow-through lysing system such as that of FIG. 4, according to one illustrated embodiment.

At 802, the material to be lysed is intermittently pumped into the chamber of the container while the container is oscillated. Such is suitable for the flow-through stop or semi-batch mode.

Figure 9:
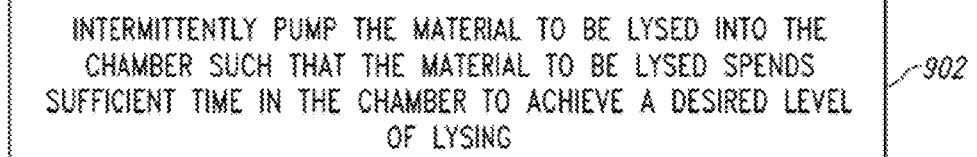
FIG. 9 is a flow diagram of a method of pumping material to be lysed in a flow through lysing system such as that of FIG. 4, according to yet another illustrated embodiment.

FIG. 9 shows a method 900 of pumping material to be lysed in a flow-through lysing system such as that of FIG. 4, according to another illustrated embodiment.

At 902, the material to be lysed is intermittently pumped into the chamber such that the material to be lysed spends a sufficient time in the chamber to achieve a desired level of lysing. Thus, if it is determined that 30 seconds of oscillation achieves a desired level of lysing, the pump may be intermittently operated to load the chamber with material to be lysed approximately every 30 seconds. Oscillation times of few seconds or tenths of seconds may be suitable. Such operation is suitable for the flow-through stop or semi-batch mode.

Figure 10:
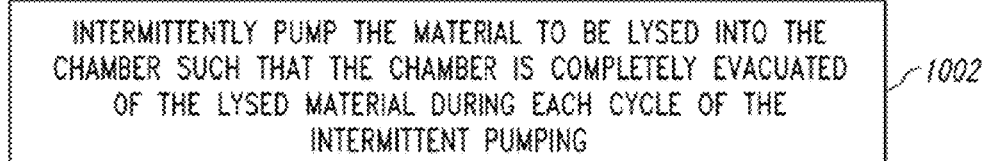
FIG. 10 is a flow diagram of a method of pumping material to be lysed in a flow-through lysing system such as that of FIG. 4, according to still another illustrated embodiment.

FIG. 10 shows a method 1000 of pumping material to be lysed in a flow-through lysing system such as that of FIG. 4, according to another illustrated embodiment.

At 1002, the material to be lysed is intermittently pumped into the chamber such that the chamber is completely evacuated of the lysed material during each cycle of the intermittent pumping. Such is suitable for the flow-through stop or semi-batch mode.

FIG. 11 shows a method 1100 of evacuating lysed material in a flow-through lysing system such as that of FIG. 4, according to another illustrated embodiment.

At 1102, the chamber is evacuated of the lysed material during each cycle of the intermittent pumping by pumping into the chamber more material to be lysed. Such is suitable for the flow-through stop or semi-batch mode.

FIG. 12 shows a method 1200 of operating a lysing apparatus such as that of FIG. 4, according to another illustrated embodiment.

At 1202, the chamber is evacuated of the lysed material each cycle of the intermittent pumping by pumping an inert fluid into the chamber. The inert fluid may take the form of a liquid or gas, and may be immiscible with the lysed material or material to be lysed. Such is suitable for the flow-through stop or semi-batch mode.

FIG. 13 shows a method 1300 of operating a continuous lysing apparatus, according to one illustrated embodiment.

At 1302, the material to be lysed is continuously pumped into the chamber of the container while the container is oscillated. Such is suitable for the flow-through continuous mode.

FIG. 14 shows a method 1400 of operating a flow-through lysing apparatus, according to another illustrated embodiment.

At 1402, a flow rate of the pumping of the material to be lysed is adjusted based at least in part on the length and free volume of the chamber such that the material to be lysed spends sufficient time in the chamber (i.e., desired or defined residence time) to achieve a desired level of lysing. Such is suitable for the flow-through continuous mode.

FIG. 15 shows a method 1500 of operating a flow-through lysing apparatus, such as that of FIG. 4, according to another illustrated embodiment.

At 1502, the lysed material removed from the chamber of the container is directed to at least one analysis device. At 1504, the lysed material is analyzed. Analysis may take a variety of forms, for example analysis with electron-microscope, western blotting, mass spectrometry, gas chromatography, etc. Such is suitable for any of the modes, and particularly suited to the flow-through modes.

Figure 16:
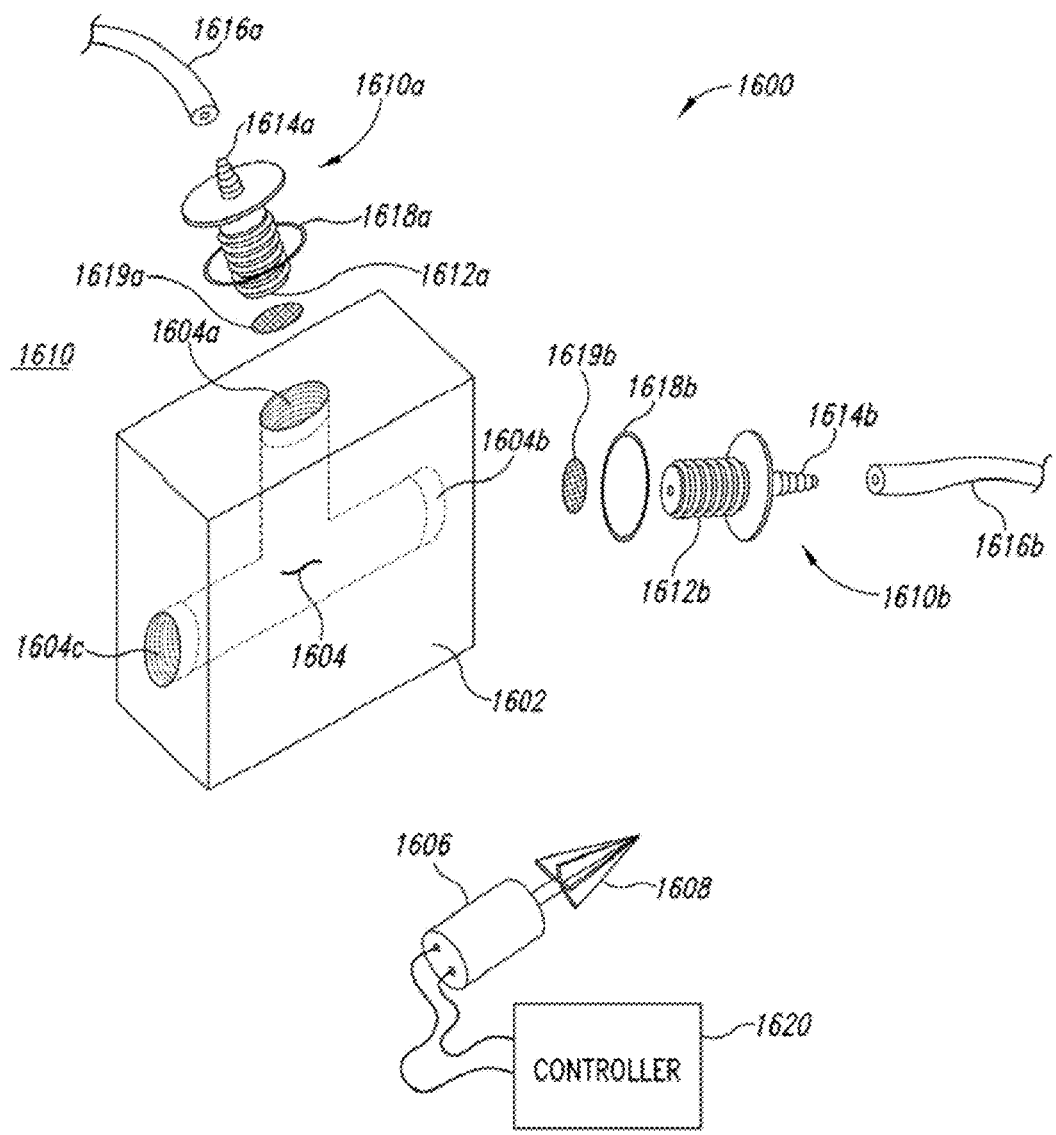
FIG. 16 is an exploded isometric view of a lysing apparatus according to another illustrated embodiment.

FIG. 16 shows a flow-through lysing apparatus 1600 according to another illustrated embodiment. As described in more detail herein, the flow through lysis system 1600 may be operated in a flow-through stop or semi-batch mode, or in a continuous flow mode.

The flow-through lysing apparatus 1600 includes a container 1602 having a chamber 1604, and a micromotor 1606 coupled to drive an impeller 1608.

As illustrated, the chamber 1604 may have a first opening 1604a that serves as an entrance providing fluid communication from an exterior 1610 of the container 1602 to the chamber 1604. Also as illustrated, the chamber 1604 may have a second opening 1604b that serves as an exit, providing fluid communication from the chamber 1604 to the exterior 1610. The container 1602 may further have a third opening 1604c sized to receive the impeller 1608 and to sealingly engage an outer portion of the micromotor 1606. Some embodiments may include a bushing or O-ring to form or enhance the sealing between the micromotor 1606 and third opening 1604c.

A first coupler 1610a may include a stem 1612a sized to be sealingly received in the opening 1604a to provide fluid communication into the chamber 1604. The stem 1612a may be threaded with the hole 1604a having a complementary thread. The first coupler 1610a may include an attachment structure, for example, a ribbed nipple 1614a to secure a tube 1616a and provide a flow of material to be lysed to the chamber 1604. An O-ring 1618a, or other similar structure, may enhance a seal between a flange of the first coupler 1610a and the container 1602.

A second coupler 1610b may include a stem 1612b sized to be sealingly received in the opening 1604b to provide fluid communication into the chamber 1604. The stem 1612b may be threaded with the hole 1604b having a complementary thread. The second coupler 1610b may include an attachment structure, for example, a ribbed nipple 1614b to secure a tube 1616b and provide a flow of material to be lysed to the chamber 1604. An O-ring 1618b, or other similar structure, may enhance a seal between a flange of the second coupler 1610b and the container 1602.

Filters 1619a, 1619b may be positioned in the chamber to retain lysing particulate material therebetween. The filters 1619a, 1619b may, for example, take the form of nylon mesh filters with 50 micron openings mounted to suitable fittings.

The micromotor 1606 may, for example, take the form of a micromotor having a 4 mm diameter, and may be capable of driving the impeller at high speed, for example approximately 50,000 RPM, when not in the presence of liquid and beads. The impeller 1608 may be a nylon or acrylic impeller having a number of vanes. The vanes may be straight, without curvature or angle of attachment, such that movement of material is primarily circumferential. Should axial/horizontal movement of the material through the chamber be desirable, for example in a flow-through mode (e.g., FIGS. 16 and 17), such axial or flow movement comes from pumping and not from rotation of the impeller. This allows more precise control over amount of time that the material remains in the chamber and hence is subject to lysis. The vanes may, for example, produce a periodic flow at a frequency nearly 5 times as high as the embodiments of FIGS. 1A-4, however with a smaller amplitude of motion.

The lysing apparatus 1600 may also include a controller 1620 coupled to control the micromotor 1606. The controller 1620 may, for example include a motor controller and/or a programmed general purpose computing system, a special purpose computer, an application specific integrated circuit (ASIC) and/or field programmable gate array (FPGA). The controller 1620 may for example, be programmed or configured to cause the motor to pulsate. Pulsating may increase the effectiveness of the lysing.

Figure 17:
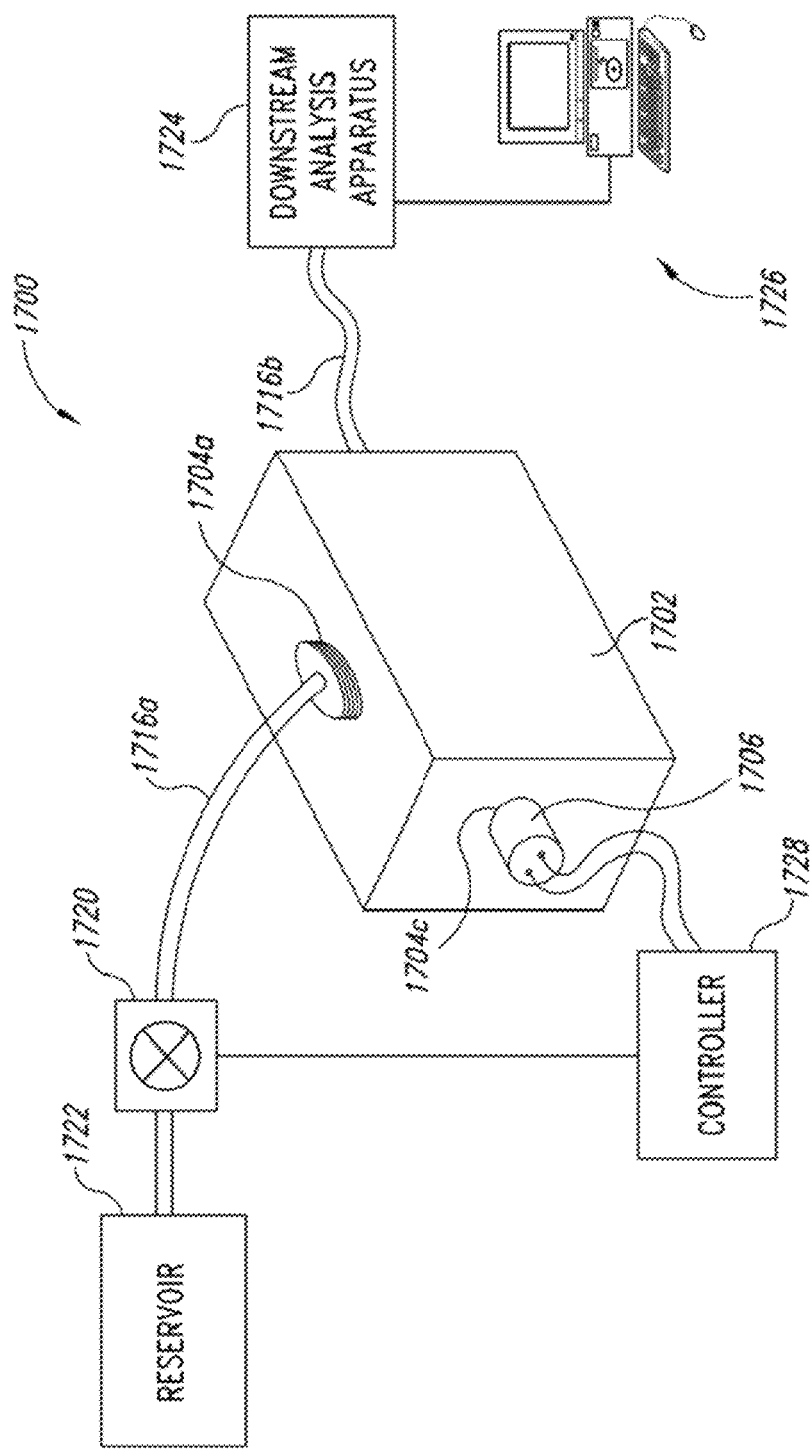
FIG. 17 is a schematic diagram of a lysing system including a lysing apparatus, an upstream subsystem to provide material to be lysed, a downstream subsystem to analyze material that has been lysed, and a control subsystem, according to another illustrated embodiment.

FIG. 17 shows a flow-through lysing system 1700 according to one illustrated embodiment. As described in more detail herein, the flow-through lysis system 1700 may be operated in a flow-through stop or semi-batch mode, or in a continuous flow mode.

The flow-through lysing system 1700 includes a container 1702 having a chamber (not illustrated in FIG. 17), openings 1704a, 1704c (only two illustrated), and a micromotor 1706 coupled to an impeller (not shown in FIG. 17). The opening or entrance 1704 may be fluidly communicatively coupled to a pump 1720 that delivers material to be lysed from a reservoir 1722 via a first conduit or tube 1716a. A second opening or exit may deliver lysed material to one or more downstream analysis apparatus 1724 via one or more conduits such as tubes 1716b. As previously noted, downstream analysis may take a variety of forms, for instance nucleic acid amplification, electrophoresis, western blotting, mass spectrometry, gas chromatography, etc. The downstream analysis apparatus 1724 may be communicatively coupled to one or more computing systems 1726. The flow-through lysing system 1700 may also include one or more control systems 1728 which may control the micromotor 1706 and/or pump 1720. The control system 1728 may for example synchronize the pumping and oscillation, for example to implement a flow-through stop or semi-batch mode. The control system 1728 may for example control the pumping to attain a desired or defined residence time of the material in the chamber to achieve a desired or defined level of lysing, for example to implement a flow-through continuous mode.

The embodiments of FIGS. 16 and 17 may advantageously allow extremely high packing densities. In these embodiments, the volume of particulate material may advantageously exceed the volume of material to be lysed or may exceed the volume of material that has been lysed. Additionally or alternatively, these embodiments may advantageously have essentially no air in the chamber. As used herein, essentially no air means that the chamber is free of air other than small bubbles which may be unintentionally entrapped in the chamber. Such may increase lysing efficiency and prevent undesirable heating of the system from friction associated with liquid-air contact line motions.

Figure 18:
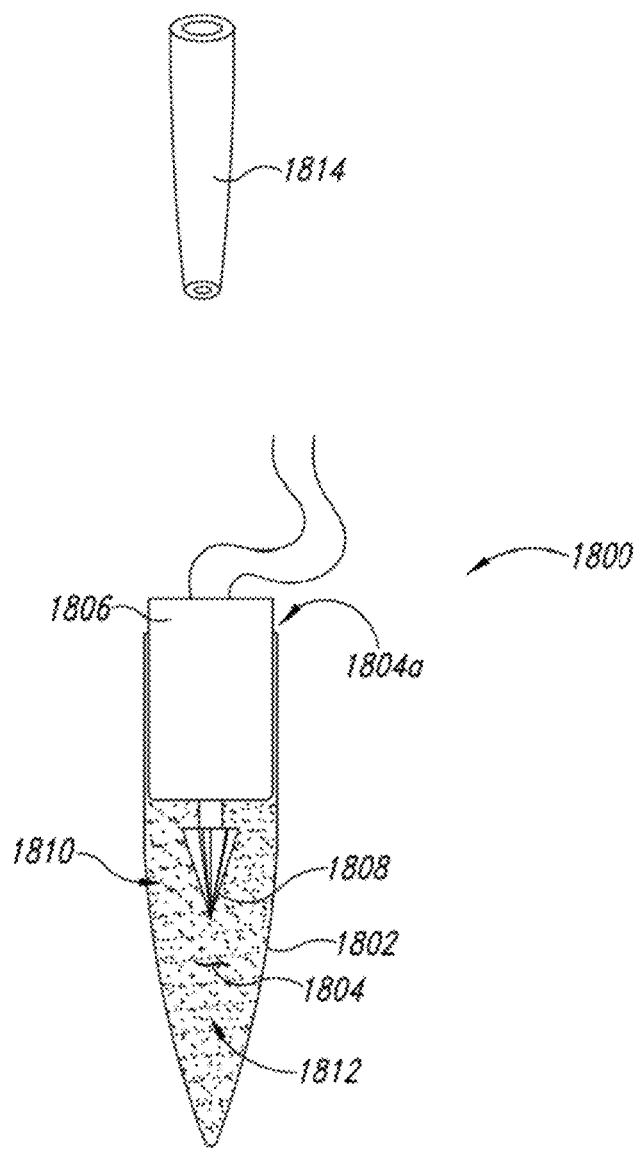
FIG. 18 is a front elevation view of a lysing apparatus and pipette according to one illustrated embodiment.

FIG. 18 shows a lysing system 1800 according to another illustrated embodiment. The lysing system 1800 is particularly suitable for batch mode lysing operations.

The lysing system 1800 includes a container 1802 having a chamber 1804 that has a single opening 1804a to provide fluid communication with an exterior of the container 1802. The apparatus 1800 includes a micromotor 1806 coupled to drive an impeller 1808 that is received in the chamber 1804. A portion of the micromotor 1806 is sized to form a sealing engagement with the container 1802 to seal the opening 1804a. Some embodiments may include one or more bushings or O-rings (not shown) to ensure the seal.

Initially, the chamber 1804 is packed with material to be lysed 1810 and lysing particulate material 1812. After rotation of the impeller 1808, for a sufficient length of time, the chamber 1804 contains material that has been lysed and the lysing particulate material 1812. The micromotor 1806 and impeller 1808 may then be removed and the lysed material may be extracted, for example using a pipette 1814. The chamber 1804 of the batch mode embodiments may not be as densely packed as in flow-through embodiments since room may be required for the apparatus to withdraw the lysed material.

In some embodiments, off-the-shelf vials and tubes may be employed as the container 1802 to hold specimens of material to be lysed and the lysing particulate material, for example PCR or Eppendorf tubes.

The embodiment of FIG. 18 may advantageously allow extremely high packing densities. In these embodiments, the volume of particulate material may advantageously exceed the volume of material to be lysed or may exceed the volume of material that has been lysed. This embodiment is less likely to ensure that there is essentially no air in the chamber since room may be required for receiving the withdrawal apparatus (e.g., pipette). However, where possible, elimination of air in the chamber may increase lysing efficiency and prevent undesirable heating of the system from friction associated with liquid-air contact line motions.

Figure 19:
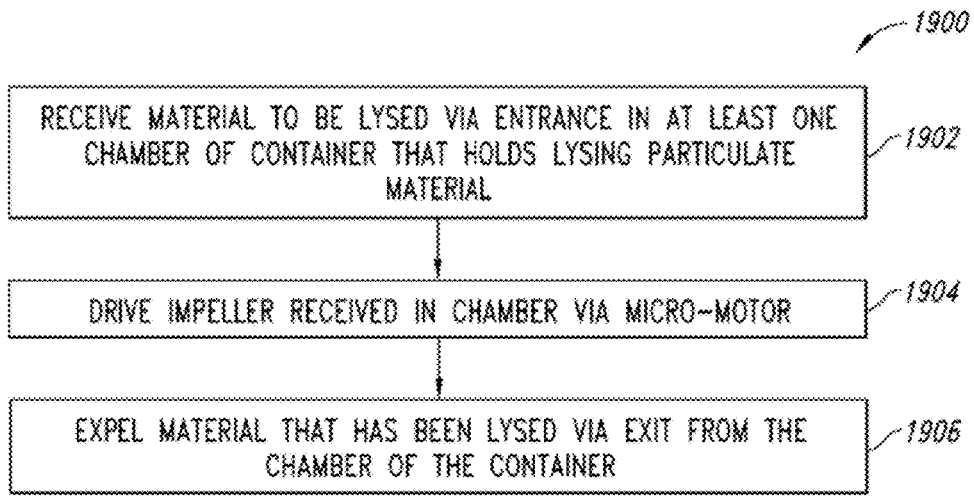
FIG. 19 shows a flow diagram of a method of operating a lysing apparatus such as that of FIGS. 16 and 17, according to one illustrated embodiment.

FIG. 19 shows a method 1900 of operating a flow-through lysing apparatus and/or system according to one illustrated embodiment. Such may be useful in a flow-through stop or semi-batch mode or in a flow-through continuous mode.

At 1902, material to be lysed is received in the chamber of a container via an entrance. The chamber may already hold lysing particulate material. At 1904, the micromotor drives the impeller to cause the lysing particulate material to lyse the material to be lysed. At 1906, material that has been lysed is expelled from the chamber of the container via an exit.

Figure 20:
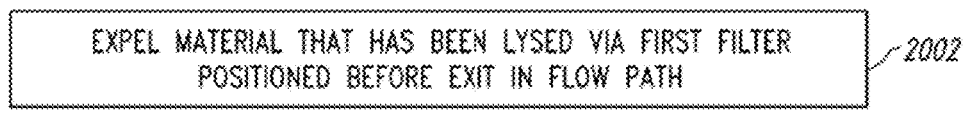
FIG. 20 is a flow diagram of a method of evacuating material that has been lysed from a chamber in operating a lysing apparatus such as that of FIGS. 16 and 17, according to another illustrated embodiment.

FIG. 20 shows a method 2000 of evacuating material that has been lysed from a chamber, according to one illustrated embodiment.

At 2002, the material that has been lysed may be expelled via a first filter position before the exit in a flow path of material through the apparatus or system.

Figure 21:
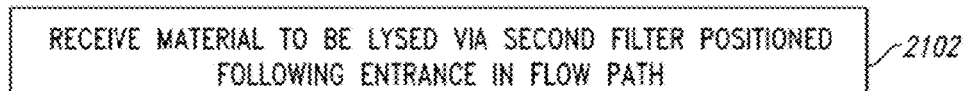
FIG. 21 is a flow diagram of a method of receiving material to be lysed in a chamber in operating a lysing apparatus such as that of FIGS. 16 and 17, according to one illustrated embodiment.

FIG. 21 shows a method 2100 of receiving material to be lysed in a chamber, according to another illustrated embodiment.

At 2102, the material to be lysed is received in the chamber via a second filter positioned following the entrance of the chamber in the flow path through the apparatus or system.

Figure 22:
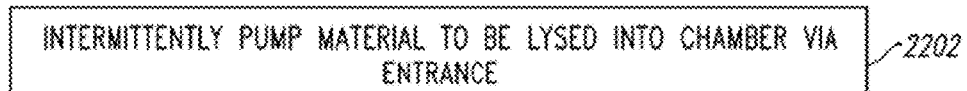
FIG. 22 is a flow diagram of a method of pumping material to be lysed into a chamber in operating a lysing apparatus such as that of FIGS. 16 and 17, according to one illustrated embodiment.

FIG. 22 shows a method 2200 of pumping material to be lysed into a chamber, according to another illustrated embodiment.

At 2202, the material to be lysed is intermittently pumped into the chamber via the entrance. Such may be particularly suitable for flow-through stop or semi-batch mode operation.

Figure 23:
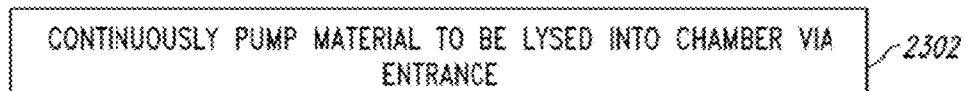
FIG. 23 is a flow diagram of a method of pumping material to be lysed into a chamber in operating a lysing apparatus such as that of FIGS. 16 and 17, according to another illustrated embodiment.

FIG. 23 shows a method 2300 of pumping material to be lysed into a chamber, according to one illustrated embodiment.

At 2302, the material to be lysed is continuously pumped into the chamber of the container via the entrance, at a flow rate that provides for a resident time of the material to be lysed in the chamber that is sufficiently long to achieve a desired or defined level of lysing. The micromotor may continuously drive the impeller to lyse the material. Such may be particularly suitable for flow-through continuous mode operation.

FIG. 24 shows a method 2400 of operating an impeller of a lysing system, according to one illustrated embodiment.

At 2402, the micromotor pulsatingly drives the impeller. Pulsations may be achieved by varying a voltage or current delivered to the micromotor. Pulsating may achieve a higher efficiency of lysing, thereby increasing throughput or decreasing time required to achieve a desired or defined level of lysing.

FIG. 25 shows a method 2500 of operating an impeller of a lysing system according to one illustrated embodiment.

At 2502, the micromotor drives the impeller at greater than 10,000 RPM in the presence of liquid and beads. Driving the impeller at a relatively high speed achieves a desired or defined level of lysing.

FIG. 26 shows a method 2600 of replacing a micromotor of a lysing system according to one illustrated embodiment.

At 2602, the micromotor may be replaced with a new micromotor. At 2604, the old micromotor may be disposed or recycled. This may be particularly useful since it is difficult to seal the internal elements (e.g., rotor, stator) of the high speed micromotor from exposure to the ambient environment, thus the micromotors may fail more frequently than in other embodiments or environments.

FIG. 27 shows a method 2700 of operating a batch based lysing apparatus according to one illustrated embodiment. The method 2700 may be particularly useful for use with the embodiment of FIG. 18.

At 2702, material to be lysed is received in a chamber of a first container via an entrance. The chamber may already hold a lysing particulate material or the lysing material may be provided into the chamber with or after the material to be lysed.

At 2704, an impeller is located in the chamber of the first container. At 2706, the entrance to the first container is closed or sealed with a micromotor. At 2708, the micromotor drives the impeller to circulate the material to be lysed and the lysing particulate material. The micromotor may drive the impeller for a sufficient length of time at a sufficient speed until a desired or defined level of lysing has occurred.

Figure 28:
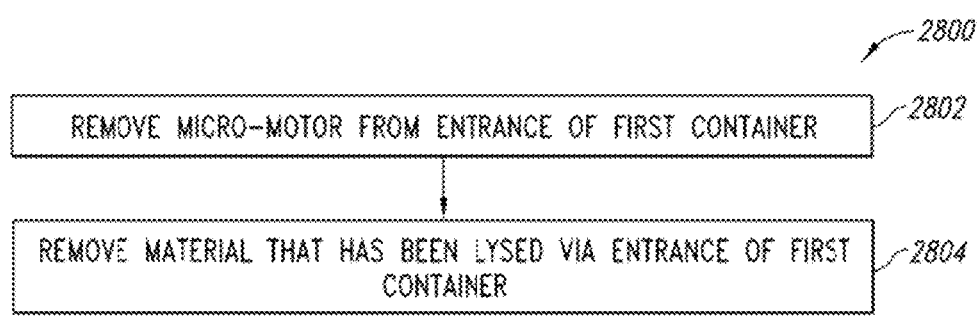
FIG. 28 is a flow diagram of a method of operating a lysing apparatus such as that of FIG. 18, according to one illustrated embodiment.

FIG. 28 shows a method 2800 of operating a lysing apparatus according to one illustrated embodiment. The method 2800 may be particularly useful for use with the embodiment of FIG. 18.

At 2802, the micromotor may be removed from the entrance of the first container. At 2804, the material that has been lysed is removed from the chamber of the first container via the entrance.

Figure 29:
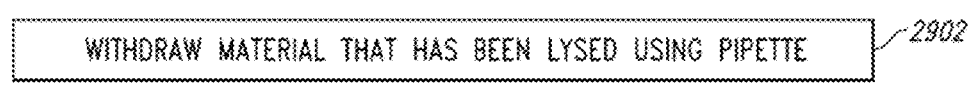
FIG. 29 is a flow diagram of a method withdrawing lysed material from a chamber of a lysing apparatus such as that of FIG. 18, according to one illustrated embodiment.

FIG. 29 shows a method 2900 of removing material that has been lysed according to one illustrated embodiment.

At 2902, the material that has been lysed may be withdrawn using a pipette.

Figure 30:
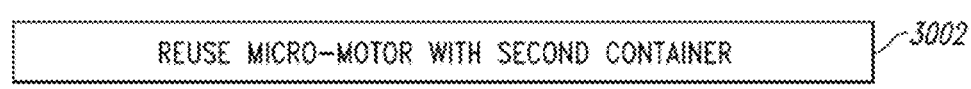
FIG. 30 is a flow diagram of a method of reusing a micromotor of a lysing apparatus such as that of FIG. 18, according to another illustrated embodiment.

FIG. 30 shows a method 3000 of operating a lysing apparatus according to another illustrated embodiment.

At 3002, the micromotor may be reused with one or more additional containers. It is noted that the micromotor, particularly when operated at high speed, may not be particularly well protected from the material to be lysed, lysing particulate material, or lysed material. Consequently, the micromotor may wear out. In many applications the micromotor may be employed to lyse multiple samples before failing.

Figure 31:
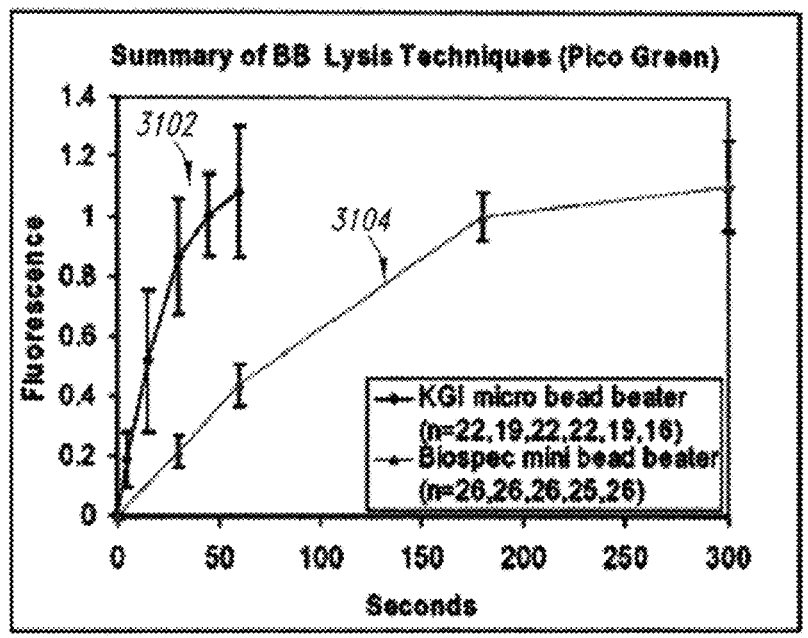
FIG. 31 is a graph showing data representing an efficiency of lysis as a function of lysing duration using an apparatus similar to that of FIG. 4.

FIG. 31 shows data on efficiency of lysis using an apparatus similar to that of FIG. 4.

A first curve 3102 represents measured fluorescence versus time of oscillation using an embodiment similar to that illustrated in FIG. 4. Fluorescence is proportional to the amount of nucleic acid released from cells. A second curve 3105 represents measured fluorescence versus time of oscillation using a commercially available "MINI-BEAD-BEATER-1 product from Biospec Products, Inc. of Bartlesville, Okla. As seen by comparison of the first curve 3102 and second curve 3105, the embodiment of FIG. 4 causes the release of cell contents more efficiently than the commercially available apparatus.

Figure 32:
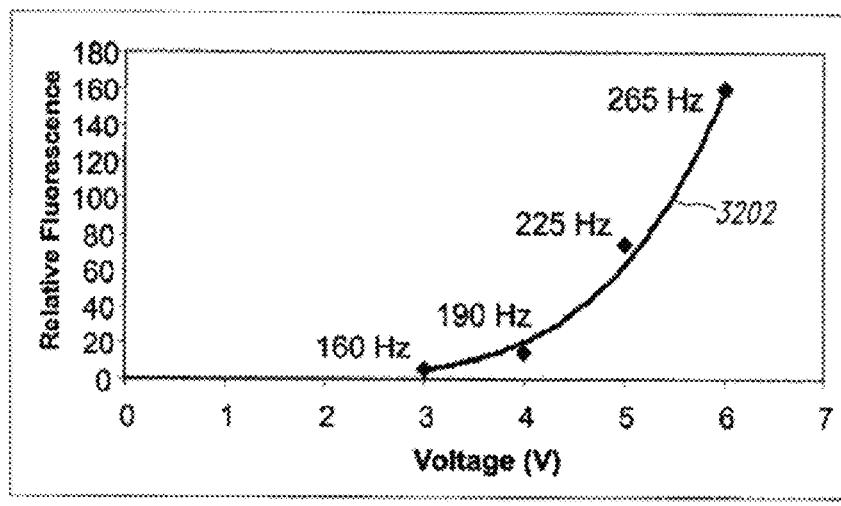
FIG. 32 is a graph showing a dependency of lysis efficiency on frequency of oscillation.

FIG. 32 illustrates a dependency of lysis efficiency on the frequency.

A curve 3202 appears to indicate a nearly quadratic dependence of the degree of lysis on frequency as controlled by changes to the applied voltage for a fixed amount of time.

Figure 33:
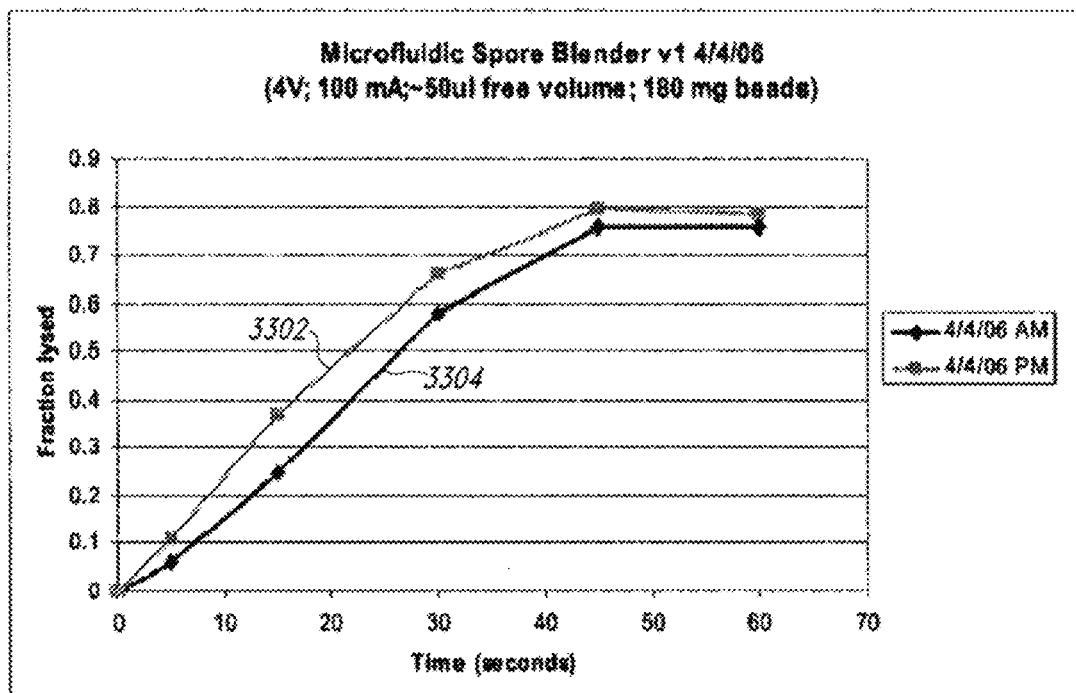
FIG. 33 is a graph showing spore lysis as a function of lysis duration for an apparatus similar to that of the embodiment of FIG. 16.

FIG. 33 shows data representing spore lysis as a function of time for an embodiment similar to that illustrated in FIGS. 16 and 17.

The curves 3302, 3304 illustrate that the time to saturation is comparable to that of the embodiments of FIG. 4, but with peak efficiency of only 80%. The power required for this efficiency was only 400 mW, which is lower than the power used for various other embodiments.

FIG. 34A shows a bidirectional flow system 3400 for lysing, capturing, and eluting a biological material according to one illustrated embodiment. As described in more detail herein, the bidirectional flow system 3400 may be operated to lyse a biological specimen, to capture a biological material on a particulate material therein, and to elute the biological material therefrom. The system 3400 in FIG. 34A is particularly suited to lysing biological specimens and controlling direction and rate of flow, chemical compositions and physical characteristics of fluids within a lysing chamber to induce capture of biological materials by and elution of such materials from a particulate lysing material therein. Efficient use of system 3400 for lysis, capture and elution surprisingly may simply require control of flow direction, pH and salt concentration of fluids within the system. Under certain conditions, controlling temperature of certain of the fluids may also be advantageous.

In certain embodiments of the design of apparatus or systems herein, the design may include multiple modules, as further discussed below. Each module may be useful for carrying out particular aspects of the methods employing such apparatus or systems. Modules may be independently functional, but in a system may be joined, for example by snapping together or via Luer-Lock connectors.

In certain embodiments, the design of an integrated modular system for lysis of specimens and capture and elution of biological material of interest therefrom is such that multiple functions are carried out by the system. A system of such a design is particularly suitable for lysis, capture and elution of a biological material by control of fluid flow direction and chemical composition of the fluids within the system during different functions of the system or phases of operation. Functions of a system, such as that shown in FIG. 34A, exemplified by the specimen being cells and the biological material being DNA, may include the following: sample introduction; fluid movement; cell disruption and DNA capture; DNA elution; optionally heating and cooling; and optionally testing the isolated DNA. At least flow direction and chemical composition are controlled during each function.

In FIG. 34A, the bidirectional flow system 3400 for lysing, capturing and eluting a biological material includes a sample and elution module 3434, a lysing module 3410, a syringe 3413, and optionally a heater 3416. The sample and elution module 3434 includes a sample reservoir 3402 and an elution buffer reservoir 3420. The lysing module 3410 includes a lysing chamber 3412 and a micromotor 3430 coupled to an impeller 3431. During operation of the system 3400, the lysing chamber 3412 contains fluid and particulate lysing material. The particulate lysing material may be densely packed within the chamber. The syringe 3413 includes a barrel 3414 and a plunger 3415. The syringe 3413 may be operated manually or driven automatically, for example by positioning the syringe 3413 within a syringe pump (not shown in FIG. 34A). Syringe pumps are commercially available, for example from New Era Pump Systems, Inc. (Wantagh, N.Y., USA) The heater 3416 may be positioned to heat fluid within the barrel 3414 of the syringe 3413.

The sample reservoir 3402 of the sample and elution module 3434 is fluidly communicatively coupled via conduit 3404, valve 3406 and conduit 3408 to the lysing chamber 3412 of the lysing module 3410. In certain embodiments, the sample reservoir 3402 contains a biological specimen suspended or dissolved in a fluid having a chemical composition suitable to induce capture of a biological material by a particulate material in the lysing chamber 3412 upon release of the biological material from the biological specimen by lysis.

The elution buffer reservoir 3420 of the sample and elution module 3434 is fluidly communicatively coupled via conduit 3418, valve 3406 and conduit 3408 to the lysing chamber 3412 of the lysing module 3410. In certain embodiments, the elution buffer reservoir 3420 contains a fluid having a chemical composition suitable to induce release of biological material from particulate material on which it has been captured in the lysing chamber 3412.

The micromotor 3430 is electrically communicatively coupled to controller 3432. The controller may control the speed, duration and/or timing of operation of the micromotor, and thus the impeller 3431 within the lysing chamber 3412.

The lysing module 3410 is fluidly communicatively coupled to the barrel 3414 of the syringe 3413. The plunger 3415 of the syringe 3413 is positioned within the barrel 3414 of the syringe 3413. The plunger 3415 of syringe 3413 may be manually or controllably slidably operable to draw fluid into the barrel 3414 by moving the plunger 3415 in a direction so as to increase the volume within the barrel 3414. Alternatively, the plunger 3415 of the syringe 3413 may be manually or controllably slidably operable to force fluid out from the barrel 3414 by moving the plunger 3415 in a direction so as to decrease the volume within the barrel 3414. The barrel 3414 of the syringe 3413 is optionally in thermal contact with the heater 3416. The heater 3416 may, for example, include a band of an electrically resistive material, for instance a foil band. The heater 3416 may provide heat to the barrel 3414 of the syringe 3413 by closing a switch 3426 to supply voltage from a source 3428 to the heater 3416. The level of heat supplied to the barrel 3414 of the syringe 3413 may be controlled, for example via a potentiometer or some other controller (not shown in FIG. 34A).

The sample and elution module 3434 further includes an outlet tube 3422, fluidly communicatively coupled to the lysing chamber 3412 via conduit 3408 and valve 3406. The outlet tube 3422 is provided as a conduit to dispense eluted biological material into receptacle 3424 for further use, such as for testing or analysis. The plunger 3415 of the syringe 3413 may be operated manually or via a controller (not shown in FIG. 34A), for example controlling the operation of a pump, to draw fluid toward the barrel 3414 of the syringe 3413 at a first rate, to push fluid away from the barrel 3414 of the syringe 3413 at a second rate, and/or to stop flow for a period of time. The first rate and the second rate may be the same or different.

In a first phase of operation of system 3400, the plunger 3415 of the syringe 3413 may be operated to draw biological specimen from the sample reservoir 3402 via the valve 3406 into and/or through the lysing chamber 3412 into the barrel 3414 of the syringe 3413. In one embodiment thereof, the impeller 3431 may be operated while sample is drawn through the lysing chamber. In another embodiment, the impeller 3431 and/or the flow may be stopped intermittently. Further, the rate of flow or the rate at which the impeller 3431 is operated may be varied. Control of one or more of these variables may allow optimization of lysis of the biological specimen and/or collection of the biological material from the biological specimen.

A chemical composition of a fluid containing a biological specimen in the sample reservoir 3402 is selected to induce or permit capture of biological material from the biological specimen upon lysis of the biological specimen in the lysing chamber 3412. For example, in certain embodiments for isolation of nucleic acids, particularly DNA, from biological specimens, fluids in which the biological specimens may be suspended or dissolved within the sample reservoir 3402 in preparation for lysis and binding of the nucleic acid by particulate material in the lysing chamber 3412 may have high salt concentrations and/or low pH.

In embodiments of specimen-containing fluids with high salt concentrations, salt concentrations of such fluids in the sample reservoir 3402, suitable to induce binding of nucleic acid, particularly DNA, to the particulate material in the lysing chamber 3412, may vary from about 200 µM to about 500 µM. In other such embodiments, salt concentration of specimen-containing fluids suitable to induce binding of a nucleic acid, particularly DNA, may range up to about 1000 µM. In yet other such embodiments, salt concentration suitable to induce binding of nucleic acids, particularly DNA, may range up to about 2000 µM or greater.

In embodiments of specimen-containing fluids with low pH, pH of such fluids in the sample reservoir 3402, suitable to induce binding of nucleic acid, particularly DNA, to the particulate material in the lysing chamber 3412 may vary from about pH 3.5 to about pH 5. In other such embodiments, pH of the specimen-containing fluids to induce binding of a nucleic acid, particularly DNA, may vary from about pH 3.75 to about pH 4.25. In yet other such embodiments, pH of specimen-containing fluids to induce binding of nucleic acids, particularly DNA, may be about pH 4.

For example, the beads can be coated with antibodies specific to markers for pathogens, such as the enterotoxin B protein from *Staphylococcus aureus*. Similarly the beads can be coated with antibodies that bind markers for cancers, such as the p53 protein.

Also for example, in a "sandwich" approach, the beads can be pre-coated with a more universal receptor such as streptavidin therefore able to capture reagents that are conferred with the corresponding ligand such as biotin. Biotinylated antibodies are both readily available and easy to make. This approach allows one version of bead, such as streptavidin coated beads to serve as a generic product that can then be used to capture any specific protein by linking with the corresponding biotinylated antibody. The binding of the biotinylated antibody can be captured on the bead either as a manufacturing process prior to sample processing or by the user prior to processing a sample, or can be performed as part of the sample processing, combining beads, antibody and sample at the same time.

As a further example, an alternative "sandwich" approach to achieving a "universal" bead to capture specific protein is to pre-coat the bead with an antibody specific to antibodies of another species, such as mouse anti-goat IgG, then use goat antibody specific to the protein of interest.

In a second phase of operation of system 3400, the plunger 3415 of the syringe 3413 may be operated to push fluid out of the barrel 3414 of the syringe 3413 back through the lysing chamber to return specimen to the sample reservoir 3402 after capture or binding of the biological material therefrom. Nonspecific capture of DNA on the beads may occur during both the forward and the reverse passage of the sample through the lysing chamber. For sequence specific capture, the fluid in the barrel 3414 of the syringe 3413 may be heated and cooled before reversing the direction of flow, as further discussed below. The fluid in the sample reservoir at the end of the capture process is waste material or material that contains analytes of a different chemistry other than what is captured by the beads. So for example DNA may be captured on the beads and proteins that have not been exposed to denaturant can be returned to the sample chamber to then be analyzed for a specific protein. A quantity of air may be initially drawn into the barrel 3414 of the syringe 3413 at the beginning of the first phase of operation and used to force all of the waste fluid from the lysing chamber and the conduits into the sample/waste reservoir at the end of the first phase of operation.

In certain embodiments, the system may include particulate material having antibodies attached thereto to capture analyte protein or polypeptide markers while other particulate material remains dedicated to capturing nucleic acids. Further, labeled antibodies may be introduced during lysis and capture, for example, to label the protein or polypeptide. After capture, the labeled antibody may be eluted, for example with Urea. In a certain embodiment, for example, if a portion of the beads are designed for DNA capture and another portion for protein or polypeptide capture, capture of both may occur at the same time. In such an embodiment, the DNA may be elute with low salt and the protein or polypeptide with urea.

Beads that are design for captured of proteins can be manufactured separately from beads that are designed for capture of nucleic acid. After the separate manufacturing processes are complete then the two bead types can be combined in useful proportions into one cartridge that is then able to process proteins and nucleic acids. The beads that are designed for protein capture can be conferred with protein specific antibodies, or with protein specific aptamers, or with a universal receptor such as streptavidin, or with a binding agent that binds proteins that have been "engineered" for specific capture. This can include using Nickel coated bead used to capture proteins with histidine tails.

Beads that are design for capture of nucleic acid can be generic, binding essentially all nucleic acids such as the silica or zirconia beads. Alternatively these beads can be conferred with specific nucleic acids (capture probes) that bind specific analytes by hybridization. Specific nucleic acid capture can also be facilitated by the sandwich approach by conferring the beads with a "universal" capture probe, and then providing a linker probe that has two domains, one domain complimentary to the analyte and the other domain complimentary to the "universal" capture probe.

Many combinations of beads for nucleic acids, specific or generic and be combined with beads for proteins, specific or generic with a single cartridge.

In a third phase of operation of system 3400, elution buffer may be drawn into the barrel 3414 of the syringe 3413 from the elution buffer reservoir 3420 via valve 3406 through lysing chamber 3412. As above, the flow may be continuous or intermittent and the rate and/or volume may be varied to optimize elution of biological material from the particulate lysing material. Further, the barrel 3414 of the syringe 3413 may be heated at this stage as well, for example to heat the elution fluid to optimize elution of captured biological material from the particulate material in the lysing chamber.

In certain embodiments of systems and methods for isolation of nucleic acids, particularly DNA, buffers for elution of the nucleic acids from the particulate material in the lysing chamber may have a lower salt concentration and/or a higher pH than the salt concentration and pH of the fluid in which the biological specimen containing the nucleic acids was suspended or dissolved to induce binding of the nucleic acids, particularly DNA, to the particulate material, as described above.

In embodiments of sample elution buffers with lower salt concentrations, the salt concentrations of the elution buffer placed in and drawn from the elution buffer reservoir 3420 may be less than about 200 µM. In other such embodiments, the salt concentrations of the elution buffers may be less than about 200 µM. In yet other such embodiments, the salt concentrations of the elution buffers may be less than about 10 µm. In particular such embodiments, the elution buffers may contain no salt.

In certain embodiments of sample elution buffers with higher pH, the pH of the elution buffers may be greater than about pH 5. In other such embodiments, the pH of the elution buffers may be greater than about pH 6. In yet other such embodiments, the pH of the elution buffer may be greater than about pH 7. In further such embodiments, the pH of the elution buffer may be greater than about pH 8.

In a fourth phase of operation, the eluted material may be pushed from the barrel 3414 of the syringe 3413 and the lysing chamber 3412 via conduit 3408, valve 3406 and outlet tube 3422 into receptacle 3424 for further manipulation or use, including analysis or testing. Air may again be expelled from the barrel 3414 of the syringe 3413 to force all of the fluid containing the biological material from the system and into the receptacle. Instead of collecting the eluate in a receptacle, the outlet tube may alternatively be connected directly to a testing apparatus in which the eluted material may be analyzed immediately upon elution. Outlet tubes may have narrow capillary sized channels to allow careful metering of the dispensed fluid, if necessary. The outlet may also include fluid sensing systems to monitor fluid flow and to provide feedback to the control system to control operation of the syringe 3413.

Use of a syringe 3413 to provide flow within the described lysis, capture and elution system provides an efficient contamination free approach, since the syringe 3413 can be readily and inexpensively replaced after each use of the system. While syringe pumps have been disclosed for use in the systems and methods disclosed herein, other types of pumps may be used, for example peristaltic pumps or other types of metering pumps. A particular advantage to use of syringe pumps or peristaltic pumps is that the syringe or tubing for the peristaltic pump is disposable and may be discarded along with the lysis chamber after each use. This provides a simple configuration for efficiently processing samples without concern for cross-contamination from one sample to the next. Although elimination of wash steps is a distinct advantage of the systems and methods disclosed herein, one or more wash steps could be included, if desired in particular embodiments, with wash fluid being provided via either the sample reservoir or the elution buffer reservoir.

Analysis or testing of biological materials obtained by systems and methods described herein may include, for example, subjecting DNA to amplification by PCR. In certain such procedures, the heater 3416 may be advantageously used. For example, in using the system 3434 to provide DNA for testing involving enzymatic amplification such as by PCR, the heater 3416 may supply heat to denature the DNA to form single strands in the barrel 3414 of the syringe 3413 prior to dispensing into the receptacle 3424. The heat-denatured DNA may then be cooled while still in the barrel 3414 of the syringe 3413 to prevent re-association of the strands. Such heat-denatured DNA may be particularly useful in enzymatic amplification reactions such as by PCR.

FIG. 34B shows positions of valve 3406 during certain phases of operation of system 3400 in FIG. 34A according to one illustrated embodiment.

Valve position 3406a in FIG. 34B may be employed for two phases of operation. One phase corresponds to withdrawing biological specimen from sample reservoir 3402, via conduit 3404, valve 3406 and conduit 3408 into lysing chamber 3412 and barrel 3414 of syringe 3413. The other phase of operation using valve position 3406a corresponds to pushing specimen remaining after lysis and collection from barrel 3414 of syringe 3413 and lysing chamber 3412 back into sample reservoir 3402 via conduit 3408, valve 3406 and conduit 3404.

Valve position 3406b in FIG. 34B may be employed for a further phase of operation. This phase, an elution phase, corresponds to withdrawing elution buffer from elution reservoir 3420 via conduit 3418, valve 3406 and conduit 3408 into lysing chamber 3412 and barrel 3414 of syringe 3413.

Valve position 3406c in FIG. 34B may be employed for yet another phase of operation. This phase, a dispensing phase, corresponds to pushing eluted biological material from barrel 3414 of syringe 3413 and lysing chamber 3412 into receptacle 3424 via conduit 3408, valve 3406 and outlet tube 3422.

Cellular samples for use in the systems disclosed herein, such as in FIG. 34A, may be obtained from a source such as a human or animal by use of swabs. Swabs may also be used to collect samples for testing from various surfaces that may hold cellular samples of interest. The cellular material collected on the swabs may then be suspended in fluid. Appropriate buffer, salts and mild detergent may be present in the fluid in order to drive the capture of DNA by the beads in the lysing chamber during lysis of the cells. The fluid sample containing the cells is placed, for example, in the sample reservoir in the sample and elution module of the system shown in FIG. 34A.

For example, binding of nucleic acid can be facilitated by cations provided by either sufficiently low pH, as low as 3.0 or sufficiently high enough concentration of salt such as NaCl, from 200 mM to 5 M, or Lithium Chloride, or ammonium Sulfate, or ammonium acetate. Chaotropic salts can be used up to 6 M.

High salt concentrations facilitate both non-specific binding of DNA to silica surfaces and sequence specific capture (hybridization) of DNA.

Detergents in the binding buffer may be used to reduce non-specific binding, such as Sodium Dodecyl Sulfate (SDS). If the detergent is compatible with nucleic amplification reactions such as PCR, then the need to wash away the detergent before elution of DNA can be avoided. These detergents are typically non-ionic and can include Tween, Triton, and Nonidet. If the salt that is used to facilitate binding the DNA is organic it may also serve to reduce non-specific binding, such as acetate as the anion or guanidinium as the cation.

Solutions that facilitate release and elution of DNA are low in ionic strength such as water, are typically buffered by concentration of buffer such as Tris at 10 mM to 30 mM. If the binding buffer has a low pH, such as pH 3 to 5 then it can help to neutralize it with a raised pH in the elution buffer, to include a range of pH 8 to 10. This will serve to facilitate release as well as compatibility with subsequent reactions of nucleic acid amplification.

Nucleic acids, in particular DNA, may be bound nonspecifically to the particulate lysing materials, as noted elsewhere herein. Alternatively, certain aspects of the materials and methods described herein may be adapted for sequence specific capture of nucleic acids. Sequence specific capture methods may be advantageous when nonspecific capture results in the capture of biological materials in addition to those of interest. For example, soil or stool samples may contain anionic polysaccharides that may be nonspecifically captured in addition to nucleic acids when using the systems and methods disclosed herein. In addition, stool samples may contain a variety of PCR inhibitors that may be non-specifically bound and may then co-purify with nucleic acids, e.g., DNA. An alternative to using particulate materials that nonspecifically bind DNA and such other materials is to incorporate sequence specific capture probes on the particulate lysing materials. These probes would be selected on the basis of specificity for binding certain sequences in the nucleic acid(s) of interest. Such use of sequence specific capture would not only eliminate binding of non-nucleic acid materials, but would also eliminate binding of host nucleic acids from host cells gathered on the swabs. Sequence specific capture methods may thus increase sensitivity. The particulate materials or beads may be functionalized by a variety of methods for use in sequence specific capture.

For example, beads may be conferred with capture probes that bind the polymerase gene of HIV. The target specific sequence may range in length that facilitate sufficient affinity and specificity for the analyte, such as but not limited to 10 to 60 nucleotides long. The capture probes can further be designed with degeneracies, to facilitate capturing all or most variations of the analyte.

When using sequence specific capture, certain aspects of the methods for lysis, capture and elution, as described above, may vary. For example, in order to expose sequences in the DNA for specific binding by the probe, the double-stranded genomic DNA must be denatured to yield single-stranded DNA. This can be done by heat denaturation. Thus, when the specimen is passed through the lysing chamber and into the syringe, the syringe may then be heated to denature the DNA that has not already bound to the beads in the lysing chamber. The heating denatures the DNA to single-stranded DNA, which may then be cooled to inhibit re-annealing. In this manner the sequences of the heat denatured single-stranded DNA are exposed to allow specific binding to probe-containing beads during passage of the heated/cooled specimen back through the lysing chamber.

In certain embodiments, a system for lysing biological specimens and capturing and eluting biological material may be a lysing module having a lysing chamber containing particulate lysing material, e.g., beads, a micromotor-driven impeller and two syringes—a first syringe and a second syringe—each having a barrel fluidly communicatively coupled to the lysing chamber of the lysing module. The barrel of either one or both of the syringes may further have a heater in thermal contact therewith. Such a system may operate similarly to the system described above. For example, biological specimen may be pumped from a barrel of the first syringe into and through the lysing chamber into a barrel of the second syringe. The waste sample may then be pumped from the barrel of the second syringe back through the lysing chamber into the barrel of the first syringe or, if the first syringe has been removed, directly into a waste receptacle. A third syringe having a barrel containing elution buffer may then be substituted in place of the first syringe. The elution buffer may be delivered from the barrel of the third syringe through the lysing chamber into the barrel of the second syringe. The third syringe may then be either removed or replaced by a fourth syringe having a barrel. The elution buffer may then be pumped from the barrel of the second syringe back through and out of the lysing chamber and either into a receptacle or into the barrel of the fourth syringe. The barrel of the second syringe may be heated as described above, that is, during the lysis and capture phase and/or during the elution phase. Each syringe may simply be operated manually or may be operated automatically, for instance via a syringe pump, a motor and linkage, a solenoid, or other actuator.

During use of the systems described herein, the volume of sample passed through the lysing chamber for cell disruption and capture of biological materials, in particular DNA may be many times the volume of the lysing chamber. In certain embodiments, volumes of sample may range from 200 µl to 2000 µl. In certain particular embodiments of the systems and methods disclosed herein, the lysing module may be an OmniLyse™ (OL™) lysing apparatus. In particular embodiments using the OL™ lysing apparatus, processing samples of a volume noted above may take between about 15 and about 120 seconds.

The embodiment of the system and methods disclosed herein shown in FIGS. 34A and 34B and described in detail above exemplifies in a non-limiting manner isolating biological materials from biological specimens lysed using an impeller apparatus within the lysing chamber 3412. However, one of skill in the relevant art will recognize that the system exemplified in FIGS. 34A and 34B and its use could readily be adapted to isolation of biological materials that are released from biological specimens lysed by other means. For example, as described in detail elsewhere herein, such biological specimens may be lysed by oscillation of a lysing chamber. Further, lysing of specimens could be carried out ultrasonically, or could even include some other type of physical or chemical treatment, so far as the method of treatment yields a biological material having a chemical composition that is appropriate for binding of the biological material to particulate material within the lysing chamber and so far as the biological material captured by and eluted from the particulate material is suitable for further use or analysis.

Figure 35A:
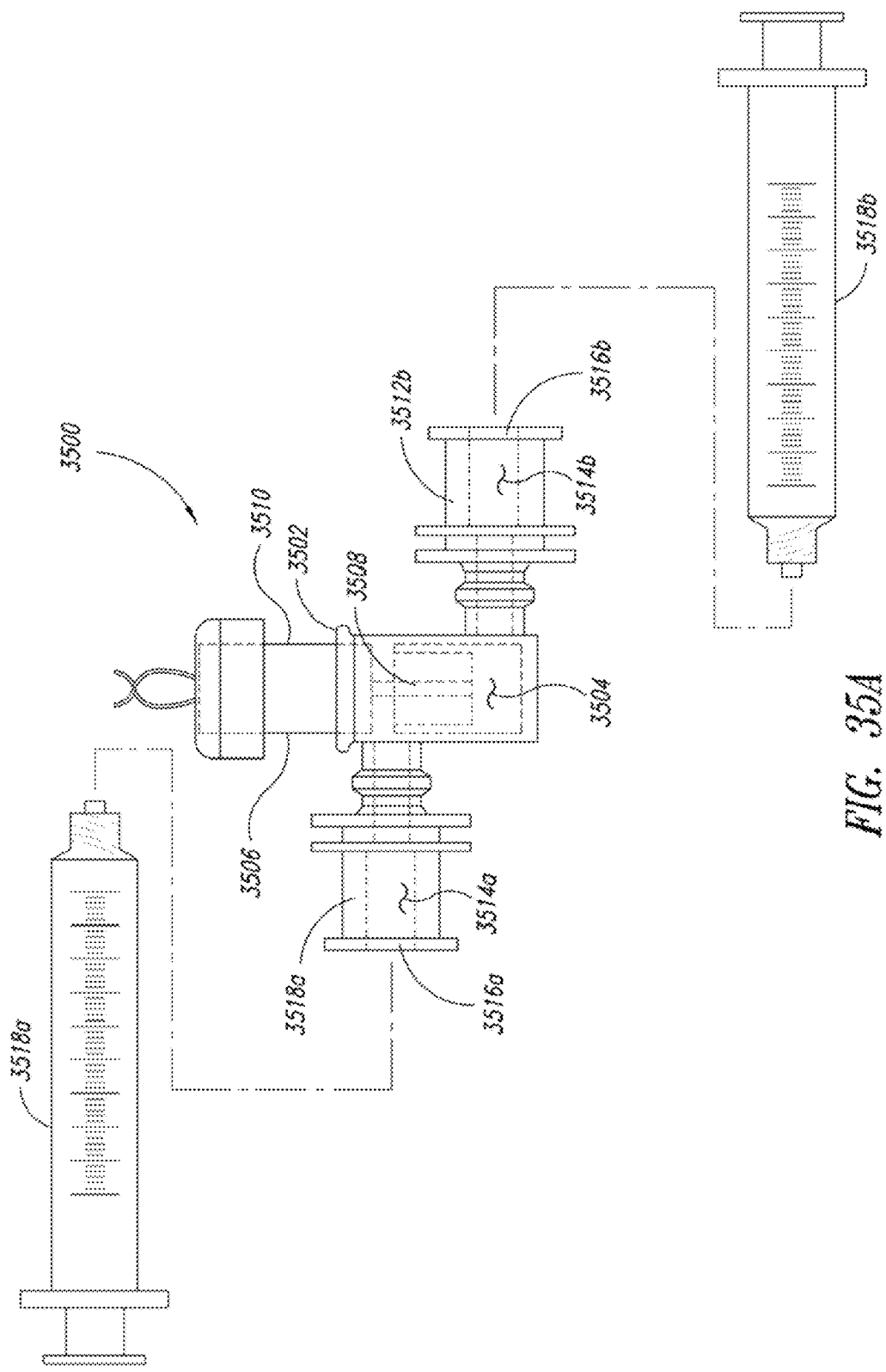
FIG. 35A is a plan view of a lysing apparatus having Luer-Lock couplers, according to one illustrated embodiment, and two syringes coupleable to the lysing apparatus via the couplers.
Figure 35B:
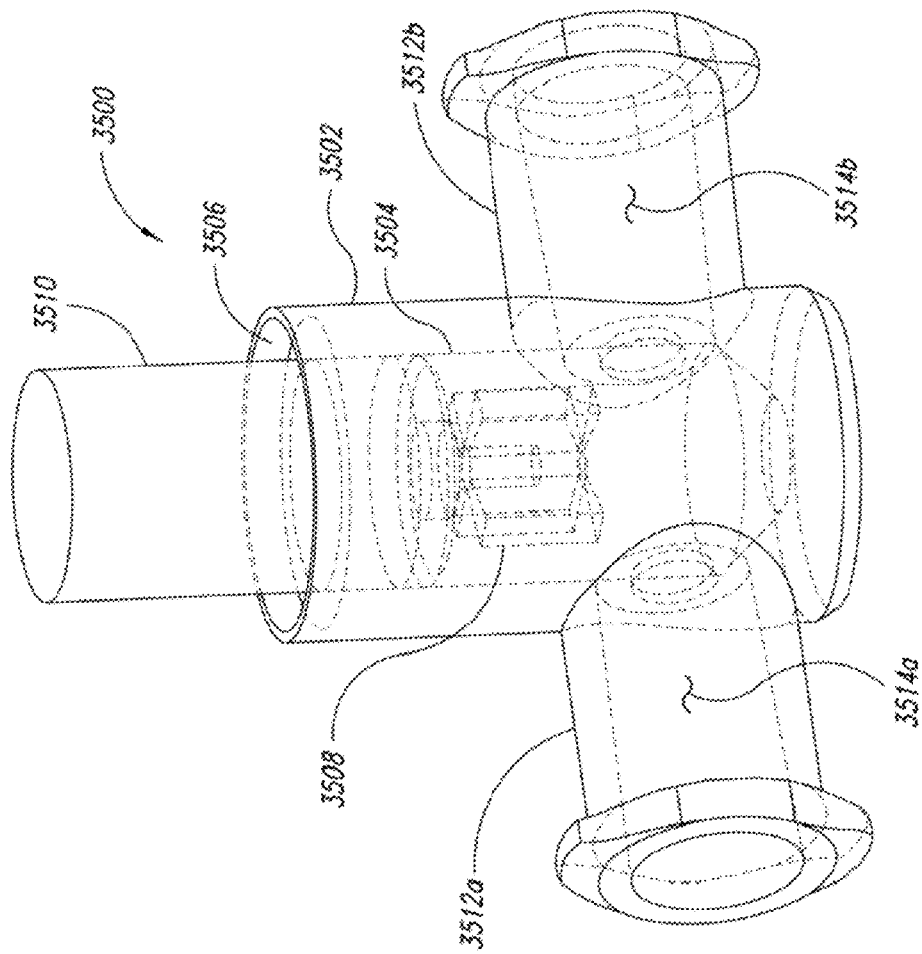
FIG. 35B is an isometric view of the lysing apparatus of FIG. 35A.

FIGS. 35A and 35B show a lysing apparatus 3500, according to another illustrated embodiment.

The lysing apparatus 3500 includes a body 3502 that forms a chamber 3504. The body 3502 may have an opening 3506 sized and dimensioned to receive an impeller 3508 therethrough such that the impeller resides in the chamber 3504. The opening 3506 may optionally receive part or all of a drive motor, for instance a micro electric motor 3510. The electric motor 3510 is coupled to drive the impeller 3508. The electric motor 3510 is selectively operable in response to power supplied thereto. The electric motor 3510 may be secured in the opening 3506 via a press type fitting or interference fit. In particular, an inner wall forming the opening 3506 and/or chamber 3504 may be slightly tapered to sealing engage a side wall of the electric motor 3510 as the electric motor is advanced through the opening 3506 and into the chamber 3504. Alternatively, or additionally, a side wall of the electric motor 3510 may be slightly tapered to sealing engage a side wall of the opening 3506 and/or the chamber 3504 as the electric motor 3510 is advanced through the opening 3506 and into the chamber 3504. Alternatively, the electric motor 3510 and the opening 3506 and/or chamber 3504 may include coupler structures. For instance, the electric motor 3510 and the opening 3506 and/or chamber 3504 may include threads (not shown) which sealing mate together as the electric motor 3510 is advanced through the opening 3506 and into the chamber 3504. Alternatively, a bayonet (not shown) or lug type (not shown) coupler structure may be employed. Other sealing structures may be employed. For example, one or more gaskets, washers or O-rings (not shown) may be employed, with or without a seat or peripheral ring to seat the gasket, washers or O-rings. The seal may be a fluid tight seal and/or a gas tight seal.

The lysing apparatus includes a first port 3512a and a second port 3512b (collectively 3512). The first and second ports 3512 include passages 3514a, 3514b, respectively, (collectively 3514) to provide fluid communication with the chamber from an exterior thereof. The ports 3512 may be used to as input ports to supply material to the chamber 3504 and/or as output ports to remove material from the chamber 3504.

Each port 3512 may have a coupler 3516a, 3516b (collectively 3516) that allows selective coupling to the respective port 3512a, 3512b. For example, each of the ports 3512 may include a respective Luer-Lock® fitting or Luer-Slip® fitting, male or female. The Luer-Lock® or Luer-Taper® fittings allow the coupling of syringes 3518a, 3518b (FIG. 35A, collectively 3518) to the lysing apparatus 3500. For example, a first syringe 3518a may be coupled to the first port 3512a to allow sample or specimen injection, while a second syringe 3518b may be coupled to the second port 3512b to allow removal of a sample or specimen after lysing (i.e., lysed material). Such may allow the passage of a sample or specimen back and forth through the chamber 3504, for instance to enhance performance of the lysing or of DNA capture. Use of syringes 3518 may occur at either port 3512a, 3512b or at both ports 3512. The advantages of using a syringe 3518 as a sample or specimen delivery system include the fact that syringes 3518 are inexpensive, disposable, and employ positive displacement of fluid for a high degree of reliability in rapidly dispensing volumes. The Luer-Lock® design exemplifies a universal attachment that seals reliably and mates with many devices that also have complimentary Luer-Lock® fittings.

As illustrated in FIG. 36, selectively fastenable fittings, such as the Luer-Lock® fittings, may allow multiple lysing apparatus 3500a-3500b (collectively, 3500, only three illustrated) to be connected in succession. Such may advantageously be used to sequentially process a sample or specimen through multiple stages. Additionally, or alternatively, lysing particulate (e.g., beads) in the different sequential lysing apparatus 3500 may each have a respective receptivity for different molecules. For instance, the particulate in successive ones of the sequential lysing apparatus may be conferred with receptors (e.g., binding sites) to capture different respective molecules from the same sample or specimen. Each lysing apparatus 3500 with a different captured molecule, may then be easily separated from one another, and processed individually using different types of elution acts or steps.

Figure 37A:
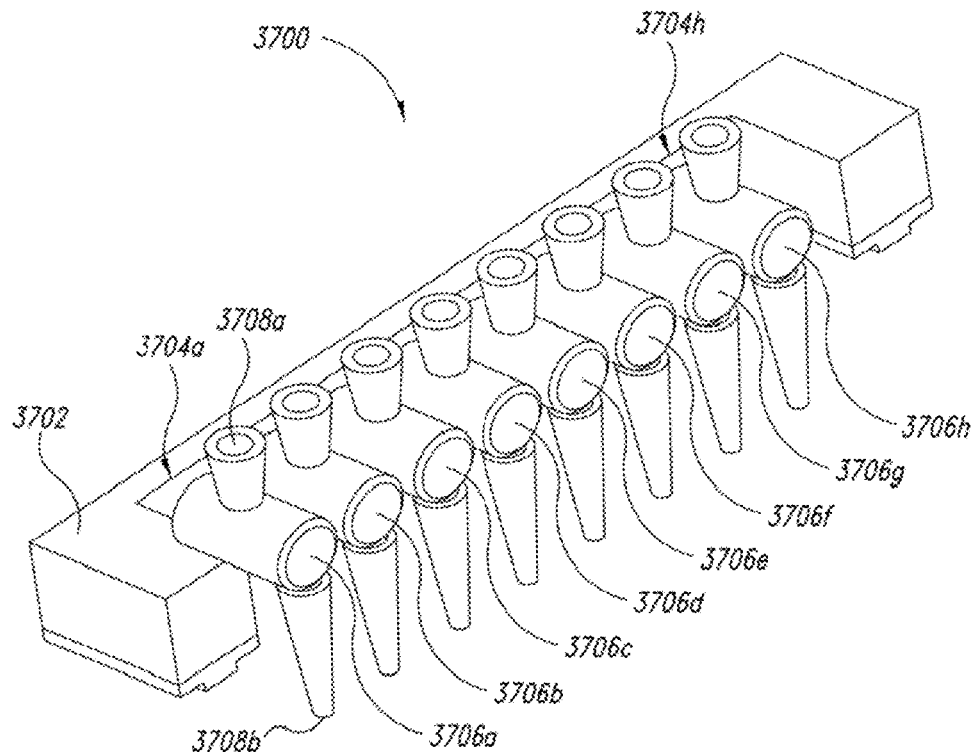
FIG. 37A is an isometric view of a manifold or array of lysing apparatus, according to one illustrated embodiment.
Figure 37B:
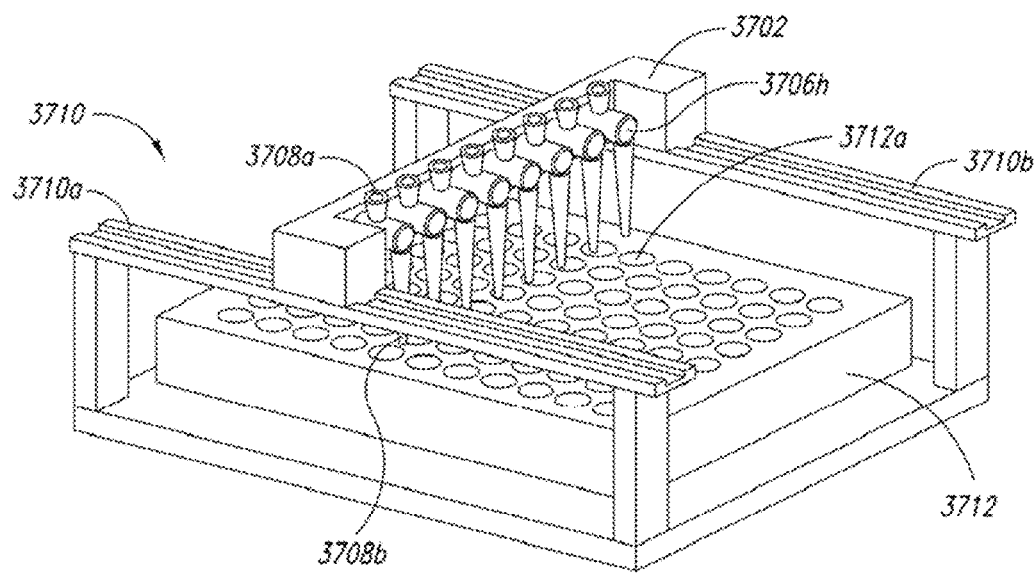
FIG. 37B is an isometric view of the manifold or array of lysing apparatus carried by a frame, according to one illustrated embodiment, the lysing apparatus positioned to deposit lysed material into respective wells of a plate.

FIGS. 37A and 37B show a lysing manifold or array 3700, according to one illustrated embodiment. The lysing manifold or array 3700 includes a block or frame 3702 that has a plurality of positions 3704a, 3704h (collectively 3704, only two called out in FIG. 37A) to hold respective ones of one or more individual lysing apparatus 3706a-3706h (collectively 3706, six illustrated). The individual lysing apparatus 3706 may, for example, take the form of distinct lysing apparatus which employ a chamber that receives an impeller and electric motor, for instance, the individual lysing apparatus 37006 may be identical or similar to the lysing apparatus 3500 (FIG. 35). Each individual lysing apparatus 3706 may include a respective disposable electric motor coupled to drive the impeller. Each individual lysing apparatus 3706 may include a first port 3708a and a second port 3708b (collectively 3708, only two called out in FIG. 37A). The ports 3708 may function as inlet and/or outlets to a chamber (not called out in FIG. 37A or 37B).

As illustrated in FIG. 37B, the lysing manifold or array 3700 may include a support structure 3710 to support one or more blocks or frames 3702 and associated individual lysing apparatus 3706. In particular, the support structure 3710 may include rails 3710a, 3710b to hold the block or frame 3702 and associated individual lysing apparatus 3706 positioned relative to a structure that receives the lysed material, for example a plate such as a micro-titer plate 3712. For instance, the support structure 3710 may hold the block or frame 3702 such that the associated individual lysing apparatus 3706 are positioned above respective ones of a plurality of wells 3712a (only one called out in FIG. 37B) of the micro-titer plate 3712. FIG. 37B shows only a single lysing manifold or array 3700 carrying a single row of individual lysing apparatus 3706, constituting a one-dimensional array of lying apparatus 3706. Alternatively, the support structure 3710 may carry additional lysing manifolds or arrays, each carrying a respective single row of individual lysing apparatus 3706. The individual lysing apparatus 3706 carried by the plurality of lysing manifolds or arrays 3700 can constitute a two-dimension array. As a further alternative, a single lysing manifold or array 3700 may carry individual lysing apparatus 3706 arranged in a two-dimensional array. As an even further alternatively, a motor and drive mechanism may be coupled to move a single lysing manifold or array 3700 carrying the individual lysing apparatus 3706 along the rails 3710a, 3710b of the support structure 3710. Thus, the one-dimensional array of lysing apparatus 3706 may be moved to address a two-dimensional array of positions. Movement may be controlled manually or automatically, for example via one or more computer processors, motors, actuators and or transmissions.

As described immediately above, individual lysing apparatus 3706 can be bundled together into a lysing manifold or array 3700 (e.g., one- or two dimensions) to facilitate multiplex processing. The distance between centers for these individual lysing apparatus 3706 can, for example, be 9 mm or a multiple of 9 mm to match a standard format of a micro-titer plate 3712 (e.g., with 9 mm spacing, 96 well plate or greater). Similarly, the use of electric motors with diameters below 4.5 mm allows the manifold or array of lysing apparatus 3700 to be used for micro-titer plate formats with 4.5 mm spacing (e.g., 384 well plate). Bundling the individual lysing apparatus 3706 in strips or rows of 4, 8, 6 or 12 may facilitate use for automated or semi-automated processing of samples in a micro-titer format. Additionally, if intake ports 3708a of the individual lysing apparatus 3706 are designed to receive sample or specimen from pipette tips, then the individual lysing apparatus 3706 may be addressed by multichannel pipettors for either manual or robotic operation. The block or frame 3702 may be fabricated monolithically from a single block of material that has been molded or cut-extruded with multiple sites for the individual lysing apparatus 3706.

The flow through nature of some embodiments may allow for reuse of the system for processing additional samples or specimens. For example, the flow through nature may facilitate performance of one or more wash acts or steps to sterilize or otherwise sanitize or cleanse the system. Containers may be reused by cleaning and/or sterilizing the container between uses. This may be coordinated with downstream processing of one sample or specimen such that the container may be made ready for another sample or specimen during the downstream processing. One or more acts may be employed to clean and/or sterilize the container, for example using a high pH or low pH solution, bleach, detergent or combinations thereof. Adjusting pH may advantageously reduce the number of wash acts or steps, since the pH can be easily neutralized. An alternative approach may be the use of di-ethyl-pyrocarbonate (DEPC). DEPC compound can destroy proteins and nucleic acid. This treatment may be followed by a single wash and then a flow of hot air. Because DEPC is so volatile, it may be removed by degradation and evaporation during the act of passing heated air over any surfaces treated with the DEPC.

The various embodiments, whether flow through or not, may allow for analyte capture through various mechanisms either within the same chamber in which lysis occurs and/or in other chambers, for instance chambers arranged subsequently with respect to a flow of sample or specimen. As explained herein the flow through systems or apparatus (e.g., oscillating arcuate motion based or rotational impeller based) can be combined with analyte capture by using the same particulate matter (i.e., lysing particulate matter) used to perform lysis to capture analyte molecules within the same chamber. Additionally, or alternatively, lysis can also be combined with an act or step that uses another mechanism for analyte capture that may normally follow the lysis act. This approach still advantageously obviates the use of harsh reagents, as well as eliminating the associated need to perform wash acts or steps prior to any subsequent enzymatic reaction. For example, 1 µm magnetic particles can be combined with the sample or specimen before or after disruption (i.e., lysing). Thus, DNA capture can occur on these magnetic particles after the disruption has been accomplished by larger lysing particulate or beads. This principle may also be applied to other non-chemical approaches to cell lysis, such as sonication, where capture may occur on an additional surface at the same time or following sonication. Such may still allow wash acts or steps to be avoided before any enzymatic reaction.

Flow through configuration and high energy mixing of lysing particulate or beads may provide distinct advantages in binding and elution kinetics. By passing the sample or specimen through a relatively small chamber with a dense suspension of lysing particulate or beads that are actively shaken up or stirred, induces a high rate of "collisions" between analyte DNA and the lysing particulate or beads. This may be similar is some respects to passing a sample or specimen through an affinity filter, providing a stark advantage over the common approach of using micron-sized magnetic beads. Such magnetic beads typically must be dispersed throughout the entire sample or specimen volume.

The interface between a solid phase and a solution phase has a boundary layer in the liquid phase that is relatively static and does not participate in active mixing. The molecules in the solution phase must diffuse through this layer to reach the surface of the solid phase. Diffusion is a slow process compared to turbulent mixing and convection. As the energy of motion of the lysing particulate or beads increases, the extent of active mixing increases, reducing this boundary layer and serving to increase the rate of arrival of DNA toward the bead surface, thus accelerating the binding. Alternatively, when eluting the DNA, the high energy motion of the lysing particulate or beads can also accelerate the dissociation of the DNA from the lysing particulate or beads by serving to escort the DNA away from the lysing particulate or beads and the boundary layer. This can be especially helpful in the common case where the DNA binding system has a large binding capacity to capture a large load DNA, e.g., 5 to 60 μg, but is also useful in capturing very low loads of analyte DNA. The high binding capacity will normally reduce the efficiency of elution for low copy numbers by offering so much surface area to re-bind with and so much boundary layer that can retain some of the DNA. The shear forces generated by the high energy motion generated by the oscillating arcuate motion based embodiments (FIGS. 1A-5) or the rotational impeller based embodiments (FIGS. 16-18) can contribute to dissociating DNA from the surface and to escorting DNA from the reduced boundary layer, enabling the DNA to join the bulk fluid that is dispensed out of the chamber during the elution act or step.

At least some of the embodiments described herein may enable a "sandwich" type of detection scheme using the lysing particulate or beads. This principle can apply to proteins and to nucleic acids, as well as other ligand/receptor combinations. In the case of nucleic acids, a DNA capture scheme such as a branched DNA assay developed at Chiron can be performed on the lysing particulate (e.g., beads) used to lyse cells and bind DNA in either the oscillating arcuate motion based apparatus (i.e., bead beater) or the rotational impeller based apparatus (i.e., bead blender). Analyte nucleic acid can be captured by heterobifunctional extender probes that can crosslink analyte sequence to capture probes that are attached to the lysing particulate or beads. Subsequent layers of branched DNA assay can be added to the captured analytes on the lysing particulate or beads. Each layer of probe can be accompanied with an adjusted speed of lysing particulate or bead mixing to mediate between the acceleration of binding of each layer and the DNA scission that is associated with the high shear forces. Building the branched DNA scheme on these lysing particulate or beads can facilitate rapid binding kinetics for each layer of binding including the capture of analyte. This can also facilitate very efficient concentration of analyte from very large volumes and can facilitate efficient wash acts or steps between binding acts or steps.

After an entire complex of probes of the branched DNA scheme has been built on the lysing particulate or beads, there are at least three ways to proceed to detection. One is to detect within the container or cartridge of the lysing apparatus (e.g., bead blender). In the case of chemiluminescent detection, mixing can occur during the detection act or step. Another approach is to dispense the lysing particulate or beads into a well or tube for detection. A further approach is to release the DNA complex from the lysing particulate or beads and elute the reporter groups into a well or tube for detection. This approach has the potential advantage of providing a better ratio of analyte specific signal to background signal by enabling a release act or step that is in fact analyte specific. For example, one or more layer of probes may be released by cleaving with light at photo-cleavable junctions. Eluting in high pH, or in low salt with heat can denature the DNA and thereby release the reporter group. Nucleases may be used to release the DNA complex at specific sites or nonspecifically. The rapid movement provided by the oscillating rotational motion based apparatus (i.e., bead beater) or the rotational impeller based apparatus (i.e., bead blender) may enhance the efficiency of the release or elution act or step.

As will be recognized by those of ordinary skill in the art based on the teachings herein, the use of lysing particulate or beads to lyse cells and to extract DNA can be performed using any surface chemistry that has a nonspecific affinity for DNA. This can include using silica or silica like beads and employing high salt or low pH to induce DNA to bind to beads followed by application of a low salt solution to elute the DNA according to the Boom method. The can also include using negatively charged beads that when accompanied by a solution of divalent cations such as Mg++, will form a salt bridge between the beads and DNA. This approach also uses low salt and EDTA to elute the DNA. Such is described at Hawkins, et al, Nucleic Acids Res. 1995, 23:22. This may also include capturing and releasing DNA with anion exchange resins on silica lysing particulate or beads. A resin such as diethylaminoethanol that contains a tertiary amine can bind DNA in low pH and can then elute DNA in the presence of a medium to high salt concentration.

FIGS. 38A and 38B show a lysis apparatus in the form of a stopcock valve 3800, according to yet another illustrated embodiment. The stopcock valve 3800 includes an outer body portion 3802 that forms a receptacle or outer chamber 3804. The stopcock valve 3800 includes an inner body portion 3806 that forms a receptacle or inner chamber 3808. The stopcock valve 3800 also includes an impeller 3810 received in the inner chamber 3808 for rotation therein. The stopcock valve 3800 further includes an electric motor 3812 coupled to drive the impeller. The stopcock valve 3800 may additionally include a handle 3818 or other engageable structure to allow a torque to be applied to the inner body portion 3806 to allow such to be easily rotated or pivoted with respect to the outer body portion 3802.

The inner body portion 3806 is rotatable (double headed arrow 3807) in the inner chamber 3808 about a longitudinal axis 3809 to open and close a plurality of ports 3820a-3820c (collectively 3820), thereby providing or shutting off fluid communication with the inner chamber 3808. Such may be employed to allow the passage of different fluids through the inner chamber 3808 at different times during the operation of the stopcock valve lysis apparatus 3800 and/or for defining different flow paths through the stopcock valve lysis apparatus 3800. The structure may ensure that one or more ports in the wall of the inner chamber 3808 fluidly communicate with a port, channel or passage through the outer body portion 3802. Thus, a port 3820 may be aligned with a channel to a pump, while at least one other port 3820 in the fluidly communicates with a channel containing a fluid intended to pass through the inner chamber 3808. This design enables the stopcock lysis apparatus 3800 to integrate with other chambers that serve other functions or which hold other fluids, such as a mix of the sample and binding buffer, elution buffer, pump, a waste reservoir, and/or chamber for amplification and detection.

Figure 39B:
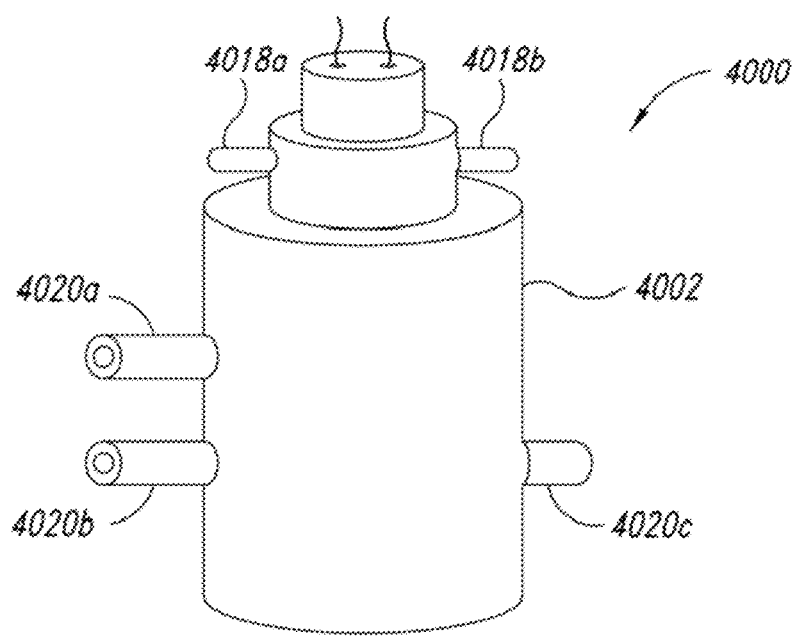
FIG. 39B is an isometric view of a stopcock style lysing device of FIG. 39A, showing an inner vessel received in an outer vessel, and an drive device including a motor and impeller received in the inner vessel.

FIGS. 39A-39C show a lysis apparatus 3900, similar to that of FIGS. 38A and 38B. In particular, FIG. 39A is an exploded view of the lysis apparatus 3900, FIG. 39B is assembled view, and FIG. 39C shows a portion of the lysis apparatus 3900 rotated 180 degrees from an orientation illustrated in FIG. 39A.

The lysis apparatus 3900 may include an outer vessel 3902 that forms an outer chamber 3904, an inner vessel 3906 that forms an inner chamber 3908, an impeller 3910 and an electric motor 3912 coupled to drive the impeller 3910. The outer chamber 3904 is sized to receive the inner vessel 3906 therein. For example, the outer chamber 3904 may have an inner peripheral or inner diameter $D_1$ that closely receives an outer periphery or outer diameter $D_2$ of the inner vessel 3906. Such may be sufficiently closely received as to form a fluid tight or a gas tight seal therebetween. Additionally, or alternatively, one or more gaskets, washers or O-rings may be employed. Additionally, or alternatively, a coupler structure (e.g., threads) may be employed. The outer chamber 3904 is open at one end 3914a, to receive the inner vessel 3906. The outer chamber 3904 may be closed at the opposite end 3914b. The inner chamber 3908 is open at one end 3916a, to receive the impeller 3910 and, optionally electric motor 3912. The inner chamber 3908 may be open at the opposite end 3916b (as illustrated in FIGS. 39A and 39C), for example where the outer chamber 3904 is closed at the opposite end 3914b. Alternatively, the inner chamber 3908 may be closed at the opposite end 3916b (as illustrated in FIGS. 40A and 40B).

The inner chamber 3908 is sized to receive the impeller 3910, and optionally part or all of the electric motor 3912 therein. For example, the inner chamber 3908 may have an inner peripheral or inner diameter $D_3$ that closely receives an outer periphery or outer diameter $D_4$ of the electric motor 3912. Such may be sufficiently closely received as to form a fluid tight or a gas tight seal therebetween. Additionally, or alternatively, one or more gaskets, washers or O-rings may be employed. Additionally, or alternatively, a coupler structure (e.g., threads) may be employed. The inner vessel 3902 may include one or more protrusions or other engageable structure 3918a, 3918b (collectively 3918) extending outwardly therefrom. Such allows the inner vessel 3906 to be easily rotated within the outer vessel 3902.

As best illustrated in FIG. 39A, the outer vessel 3902 has a number of ports 3920a-3920c (collectively 3920) to provide fluid communications or a fluid path between the outer chamber 3904 and an exterior of the outer vessel 3902. Three ports 3920a-3920c are shown in the illustrated embodiment, although fewer or greater number of ports may be employed. Likewise, the inner vessel 3906 has a number of ports 3922a-3922c (collectively 3922) to provide fluid communications or a fluid path between the inner chamber 3908 and an exterior of the inner vessel 3906. Three ports 3922a-3922c are shown in the illustrated embodiment, although fewer or greater number of ports may be employed. The ports 3920, 3922 arranged such that selected ports on the inner vessel 3906 align with selected ports on the outer vessel 3902 in a first orientation or configuration (FIG. 39A), while selected ports on the inner vessel 3906 align with selected ports on the outer vessel 3902 in a second orientation or configuration (FIG. 39C), different from the first orientation or configuration. The fluid path can be modified by simply orienting the inner vessel 3906 with respect to the outer vessel 3902. For example, in the illustrated embodiment, a first fluid path between ports 3920a, 3920b of the outer vessel 3902 is established when the inner vessel 3906 is in a first orientation (FIG. 39A) with respect to the outer vessel 3902. Rotating the inner vessel 3906 with respect to the outer vessel 3902, for instance 180 degrees about a longitudinal axis (orientation illustrated in FIG. 39C), establishes a second fluid path between ports 3920a, 3920c of the outer vessel 3902. Notably, the inner wall or periphery that forms the outer chamber 3904 selectively seals one of the ports 3922a, 3922c of the inner vessel 3906 depending on the orientation of the inner vessel 3906 with respect to the outer vessel 3902. Other embodiments may employ additional ports. Ports may be oriented at angles other than 180 degrees from one another. Thus, for example, the inner vessel 3906 may have ports oriented at 90 degrees, 60 degrees or 45 degrees from each other. Such may provide a greater number of selectively selectable fluid paths. While the outer and inner vessels 3902, 3906, respectively, are illustrated having an equal number of ports 3920, 3922, respectively, in some embodiments the number of ports of the outer and inner vessels 3902, 3906 may not be equal to one another.

Figure 40B:
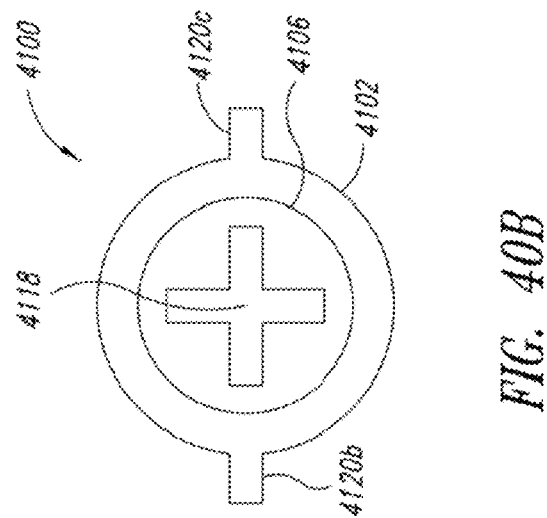
FIG. 40B is an bottom plan view of a stopcock style lysing device of FIG. 40A.
Figure 40A:
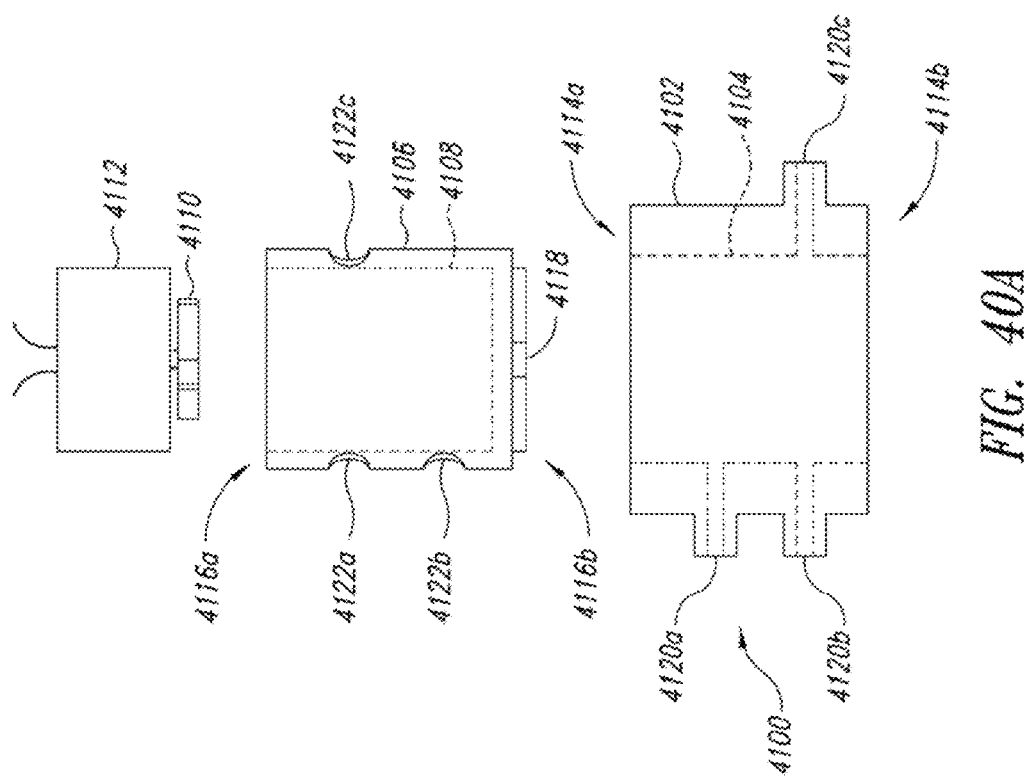
FIG. 40A is an exploded side elevational view of a stopcock style lysing device, according to another illustrated embodiment, showing an inner vessel with a closed bottom portion.

FIGS. 40A and 40B show a show a lysis apparatus 4000, similar to that of FIGS. 38A and 38B. In particular, FIG. 40A is an exploded view of the lysis apparatus 4000 and FIG. 40B shows a bottom of the lysis apparatus 4000.

The lysis apparatus 4000 may include an outer vessel 4002 that forms an outer chamber 4004, an inner vessel 4006 that forms an inner chamber 4008, an impeller 4010 and an electric motor 4012 coupled to drive the impeller 4010. The outer chamber 4004 is sized to receive the inner vessel 4006 therein. For example, the outer chamber 4004 may have an inner peripheral or inner diameter that closely receives an outer periphery or outer diameter of the inner vessel 4006. Such may be sufficiently closely received as to form a fluid tight or a gas tight seal therebetween. Additionally, or alternatively, one or more gaskets, washers or O-rings may be employed. Additionally, or alternatively, a coupler structure (e.g., threads) may be employed. The outer chamber 4004 may be open at both ends 4014a, 4014b, to receive the inner vessel 4006. The inner chamber 4008 is open at one end 4016a to receive the impeller 4010 and, optionally electric motor 4012. The inner chamber 4008 is closed at the opposite end 4016b which thus closes the opposite end 4014b of the outer chamber 4004. The inner vessel 4006 has one or more protrusions or other engageable structure 4018 extending from the opposite end 4016b thereof. Such allows the inner vessel 4006 to be easily rotated within the outer vessel 4002.

The inner chamber 4008 is sized to receive the impeller 4010, and optionally part or all of the electric motor 4012 therein. For example, the inner chamber 4008 may have an inner peripheral or inner diameter that closely receives an outer periphery or outer diameter of the electric motor 4012. Such may be sufficiently closely received as to form a fluid tight or a gas tight seal therebetween. Additionally, or alternatively, one or more gaskets, washers or O-rings may be employed. Additionally, or alternatively, a coupler structure (e.g., threads) may be employed.

As best illustrated in FIG. 40A, the outer vessel 4002 has a number of ports 4020a-4020c (collectively 4020) to provide fluid communications or a fluid path between the outer chamber 4004 and an exterior of the outer vessel 4002. Three ports 4020a-4020c are shown in the illustrated embodiment, although fewer or greater number of ports may be employed. Likewise, the inner vessel 4006 has a number of ports 4022a-4022c (collectively 4022) to provide fluid communications or a fluid path between the inner chamber 4008 and an exterior of the inner vessel 4006. Three ports 4022a-4022c are shown in the illustrated embodiment, although fewer or greater number of ports may be employed. The ports 4020, 4022 arranged such that selected ports on the inner vessel 4006 align with selected ports on the outer vessel 4002 in a first orientation or configuration (FIG. 40A), while selected ports on the inner vessel 4006 align with selected ports on the outer vessel 4002 in a second orientation or configuration, different from the first orientation or configuration. The fluid path can be modified by simply orienting the inner vessel 4006 with respect to the outer vessel 4002. For example, in the illustrated embodiment, a first fluid path between ports 4020a, 4020b of the outer vessel 4002 is established when the inner vessel 4006 is in a first orientation (FIG. 40A) with respect to the outer vessel 4002. Rotating the inner vessel 4006 with respect to the outer vessel 4002, for instance 180 degrees about a longitudinal axis, establishes a second fluid path between ports 4020a, 4020c of the outer vessel 4002. Notably, the inner wall or periphery that forms the outer chamber 4004 selectively seals one of the ports 4022a, 4022c of the inner vessel 4006 depending on the orientation of the inner vessel 4006 with respect to the outer vessel 4002. Other embodiments may employ additional ports. Ports may be oriented at angles other than 180 degrees from one another. Thus, for example, the inner vessel 4006 may have ports oriented at 90 degrees, 60 degrees or 45 degrees from each other. Such may provide a greater number of selectively selectable fluid paths. While the outer and inner vessels 4002, 4006, respectively, are illustrated having an equal number of ports 4020, 4022, respectively, in some embodiments the number of ports of the outer and inner vessels 4002, 4006 may not be equal to one another.

While the embodiments of FIGS. 38A-38B, 39A-39C, 40A-40B may all be manually operated (e.g., manually rotated to select a desired flow path or port), some embodiments may be automatically operated, for example drive by an electric motor, solenoid or other electrical or electromechanical actuator.

Figure 41:
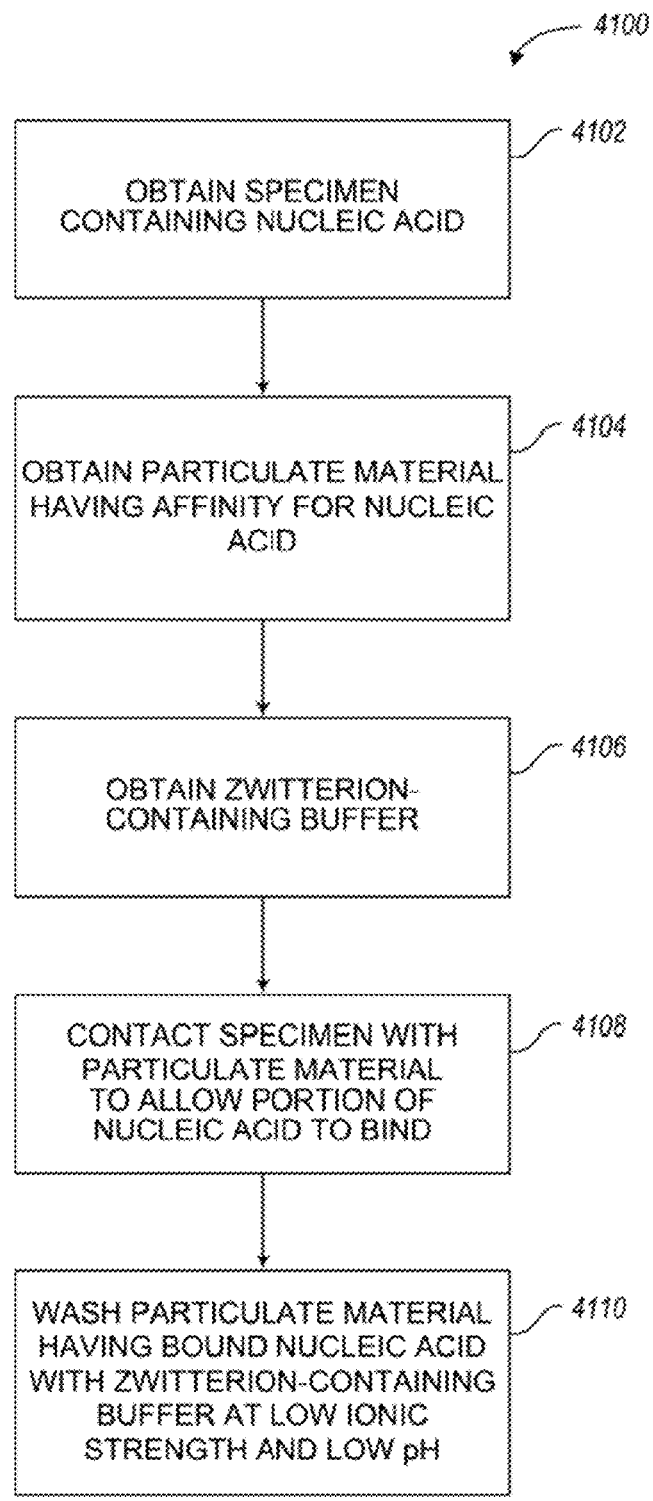
FIG. 41 is a flow diagram of aspects of a method of processing a nucleic acid-containing specimen including washing particle-bound nucleic acid, according to one embodiment.

FIG. 41 shows a method 4100 of isolating nucleic acid from a specimen according to one illustrated embodiment. Method 4100 may be useful in aspects of methods of lysing, extracting, capturing and isolating biological materials described elsewhere herein. Alternatively, method 4100 may be useful in combination with a variety of other approaches to the isolation of biological materials, particularly nucleic acids such as DNA, known and practiced in the art.

At 4102, a specimen containing nucleic acid is obtained. The specimen may include any of a variety of preparations containing nucleic acid for further processing. Such a specimen may range from relatively crude preparations of lysed cells to relatively clean solutions of partially purified nucleic acid.

At 4104, a particulate material having an affinity for nucleic acid is obtained. The particulate material may have the form of a bead. Such particulate materials may include any of a variety of such materials known in the art and available for binding nucleic acids, including but not necessarily limited to particles made from ceramic, glass, zirconia, silica, or sand, as well as particles having a metal core coated by a material that facilitates binding of nucleic acid.

At 4106, a low ionic strength zwitterion-containing buffer is obtained. A zwitterion is a polar chemical compound that at a particular pH, termed its isoelectric point (pI), has a positive and a negative charge on different atoms and thus a net charge of zero. The acidic and basic functional groups of a zwitterion have dissociation constants, the logarithms of which are termed, respectively, pKa and pKb (or $pKa_1$ and $pKa_2$). Within a range around these dissociation constants, zwitterions serve as effective buffering agents. For example, several amino acids are useful as buffering agent in a range between about pH 2 and pH 4. At the upper end of that range as the pH approaches the isoelectric point the net charge on the molecule decreases. Thus, for example, at pH 4 an amino acid such as glycine may serve as a buffer while contributing relatively little to ionic strength of the solution. Many other amino acids, aminosulfonic acids and aminocarboxylic acids may have similar utility as buffers while contributing relatively little to ionic strength within a range near their pKa's.

At 4108, the specimen is contacted with the particulate material to allow at least a portion of the nucleic acid to bind to the particulate material. Composition of the specimen may help to induce binding of the specimen to a particulate material. In methods commonly known in the art, nucleic acid-containing compositions at very high ionic strength and pH near neutrality, such as conditions used during chemical lysis of cells, promote binding of nucleic acids to surfaces such as various types of silica, zirconia or ceramic surfaces. For example, commonly used compositions that promote binding of nucleic acids to such surfaces may include salts in a range of concentrations between about 2M and about 6M, chaotropic chemical lysing agents such as guanidine hydrochloride or guanidine thiocyanate in a range as high as between 6M and 10M, typically in a pH range between about 6 and about 8. Carrying out such operations requires further manipulation of the particle-bound nucleic acids to remove such materials in order to provide nucleic acids that are suitable for subsequent reaction and/or analysis, for example, amplification by PCR. Removing the salts and/or chaotropes requires, at minimum, extensive washing, typically also at a pH between about 6 and about 8, often including alcohol as well. During wash, as the ionic strength decreases at pH 6-8, the nucleic acids begin to release from the surface of the particulate, leading to decreased yields. Further, use of alcohol as a wash medium requires drying of the washed particles to remove the alcohol. It has been surprisingly discovered that by suitable selection of a buffering agent and a pH, particle-bound nucleic acids can be washed under conditions such that the nucleic acids remain bound to the particles. The nucleic acids can then be selectively eluted once the wash is complete.

At 4110, the particulate material having bound nucleic acid is washed with a zwitterion-containing buffer at a low pH and a low ionic strength. For example, at pH 4 and low ionic strength nucleic acid remains bound to the silica, zirconia or ceramic particles. Suitable buffer ions for use under such conditions to provide buffering at pH 4 while contributing only low ionic strength to the solution include, as noted above, various amino acids, aminosulfonic acids and aminocarboxylic acids. For example, low ionic strength glycine buffer at pH 4 is particularly suitable as a wash buffer for particle-bound nucleic acid. In certain embodiments, such buffer may be advantageously used to wash particle-bound nucleic acids following use of harsh chemical lysing. Under such conditions the harsh agents are removed while the nucleic acids remain bound. Following washing with such zwitterionic buffers at low ionic strength and low pH, the nucleic acid may be readily released from the particles simply by increasing the pH to around neutrality, thus yielding a nucleic acid solution particularly suitable for subsequent analysis, e.g., by PCR.

In certain embodiments, a zwitterion-containing wash buffer as described above may be used as a binding buffer because it not only prevents release but also induces binding of nucleic acids to particles under the conditions described.

Zwitterionic substances suitable for use in a wash buffer or a binding buffer as described may advantageously have pKa, i.e., $pKa_1$, values between about 2 and about 4.

In one embodiment, formulations suitable for carrying out the methods described herein, including formulations for washing particle bound nucleic acids, may include formulations having a low ionic strength zwitterion-containing buffer having a pH between about 3.5 and about 5 and including zwitterionic substances with a pKa between about 2 and about 4 and/or a pKb between about 9 and about 11.

In certain embodiments, a kit may be suitable for use in methods for isolating a nucleic acid. In certain embodiments, a kit may include a particulate material that has affinity for nucleic acid and a low ionic strength zwitterionic buffer having a pH less than about 6. In certain embodiments, the kit may include instructions for using the kit contents to isolate a nucleic acid. In certain embodiments, the low ionic strength zwitterion-containing buffer may have a pH between about 3 and about 6. In certain embodiments, the zwitterionic buffer in the kit may include an amino acid, an aminosulfonic acid, or an aminocarboxylic acid.

Figure 42:
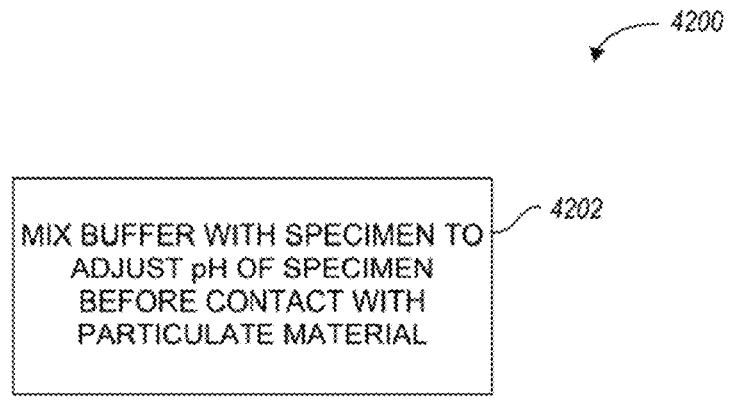
FIG. 42 is a flow diagram of an aspect of a method of preparing a nucleic acid-containing specimen for processing by a method such as that of FIG. 41, according to one embodiment.

FIG. 42 shows a method 4200 for carrying out a particular aspect of method 4100 directed to isolating a nucleic acid in one illustrated embodiment.

At 4202, a specimen is mixed with buffer to adjust the pH of the specimen before contacting the specimen with a particulate material. In a certain embodiment, the pH of the specimen may be adjusted to below 5 to induce binding of nucleic acid from the specimen to the particulate material.

Figure 43:
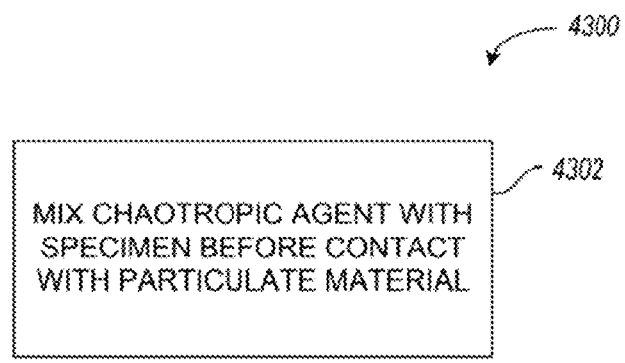
FIG. 43 is a flow diagram of an aspect of a method of preparing a nucleic acid-containing specimen for processing by a method such as that of FIG. 41, according to another embodiment.

FIG. 43 shows a method 4300 for carrying out a particular aspect of method 4100 directed to isolating a nucleic acid in one illustrated embodiment.

At 4302, a specimen is mixed with a chaotropic agent before contact with the particulate material. In a certain embodiment, the chaotropic agent may be used at a concentration sufficient to chemically lyse a biological material in the specimen. For example, the chaotropic agent may lyse a cell wall. In a certain embodiment, the chaotropic agent may induce binding of nucleic acid to the particulate material. In method 4100, washing particles having bound nucleic acid with low ionic strength, low pH zwitterionic buffer allows efficient removal of the chaotropic agents without dissociating the nucleic acid from the particulate material.

Figure 44:
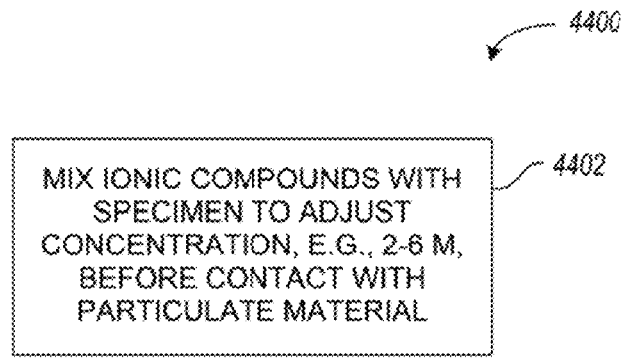
FIG. 44 is a flow diagram of an aspect of a method of preparing a nucleic acid-containing specimen for processing by a method such as that of FIG. 41, according to yet another embodiment.

FIG. 44 shows a method 4400 for carrying out a particular aspect of method 4100 directed to isolating a nucleic acid in one illustrated embodiment.

At 4402, a specimen is mixed with ionic compounds to adjust the concentration of ionic compounds in the specimen. In certain embodiments, ionic compounds may be added to adjust the concentration to between 2M and 6M. High concentrations of ionic compounds may be used to induce binding of nucleic acid to particulate material. In method 4100, washing particles having bound nucleic acid with low ionic strength, low pH zwitterionic buffer allows efficient removal of the high concentrations of ionic compounds that may be used initially to induce binding of the nucleic acid to the particulate material.

Figure 45:
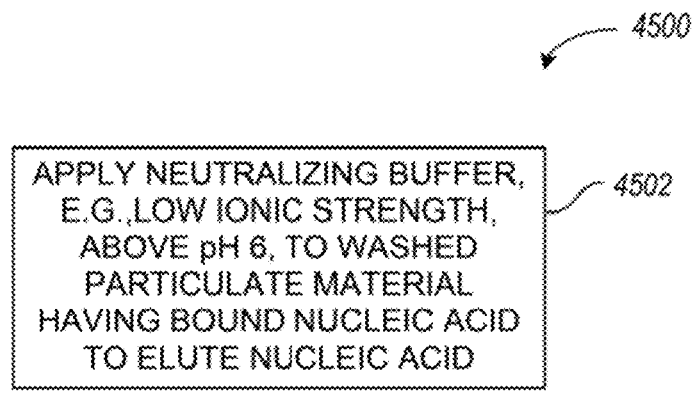
FIG. 45 is a flow diagram of an aspect of a method of processing a nucleic acid-containing specimen by a method such as that of FIG. 41 including eluting particle-bound nucleic acid, according to one embodiment.

FIG. 45 shows a method 4500 for further processing the particulate material having bound nucleic acid after washing with the zwitterion-containing buffer in one illustrated embodiment.

At 4502, a low ionic strength buffer having a pH above 6 is applied to the washed nucleic acid-containing particulate material. Applying the buffer increases the pH at the surface of the particulate material, thus neutralizing residual wash buffer and eluting the bound nucleic acid while maintaining a low ionic strength.

Figure 46:
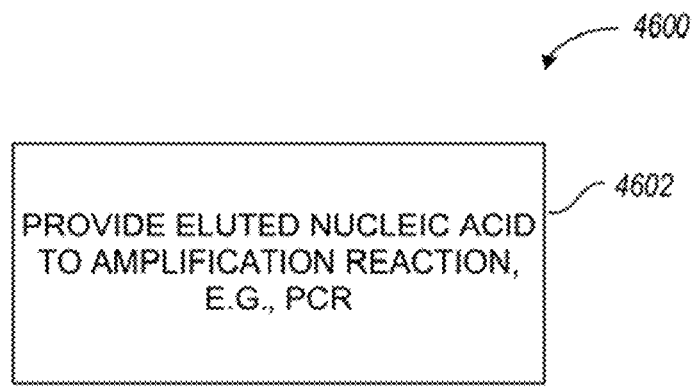
FIG. 46 is a flow diagram of an aspect of a method of processing a nucleic acid-containing specimen by a method such as that of FIG. 41 including providing eluted nucleic acid for amplification, according to one embodiment.

FIG. 46 shows a method 4600 for further processing nucleic acid eluted from the particular by method 4500 in one illustrated embodiment.

At 4602, the eluted nucleic acid is provided for further processing in an amplification reaction, e.g., by PCR. Nucleic acid in a low ionic strength buffer at a pH near neutrality as obtained from methods 4100 and 4500 is particularly suitable for further processing and analysis.

Figure 47:
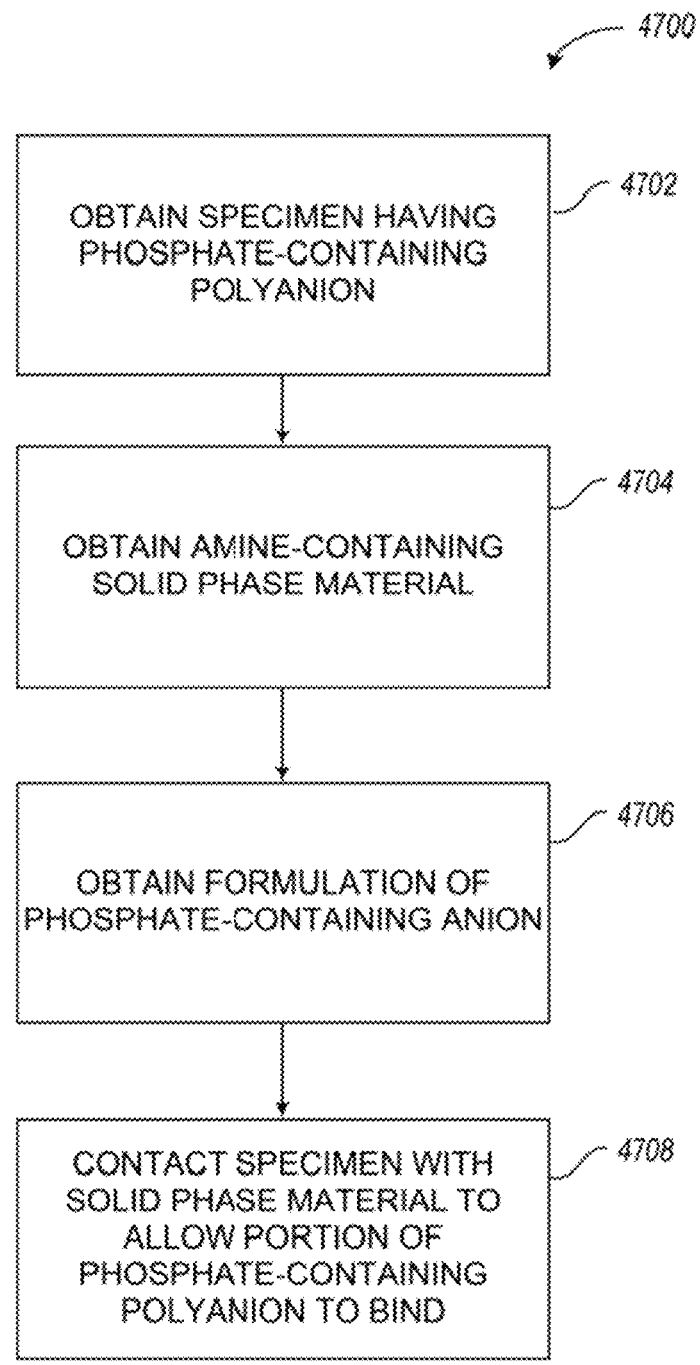
FIG. 47 is a flow diagram of aspects of a method of processing a phosphate-containing polyanion using an amine-containing solid phase material, according to one embodiment.

FIG. 47 shows a method 4700 for isolating phosphate-containing polyanions using an amine-containing solid phase material in one illustrated embodiment. Phosphate-containing polyanions include nucleic acids such as DNA.

At 4702, a specimen having phosphate-containing polyanions is obtained. At a pH of around about 7, the phosphate-containing polyanions have a negative charge. Such polymeric molecules may be obtained from cells that are either mechanically or chemically lysed. Cells that are mechanically lysed to obtain phosphate-containing polyanions may be lysed by methods described elsewhere herein.

At 4704, an amine-containing or aminated solid phase material is obtained. At a pH of around about 7, the amine groups on the amine-containing solid phase material are positively charged. Thus, the positively charged amine-containing solid phase material will bind the negatively charged phosphate-containing polyanions. However, the positively charged amine-containing solid phase material may also bind other negatively charged molecules that may be present in the specimen. Thus eluting phosphate-containing polyanions from the amine-containing solid phase material may elute not only the polyanions of interest but also other negative charge species. Accordingly, such would not necessarily be a reliable approach to isolating phosphate-containing polyanions, e.g., nucleic acids such as DNA. An alternative approach takes advantage of the phosphate-containing moieties in the polyanion and the possible involvement of such moieties in the binding of the polyanion to the amine-containing solid phase material.

At 4706, a formulation of phosphate-containing anions is obtained. The formulation may include one or more of a variety of phosphate-containing anions. For example, such anions may include organic or inorganic phosphates. Phosphate-containing anions may be considered and selected on the basis of possible chemical and/or structural similarity to the phosphate moieties on the phosphate-containing polyanions.

At 4708, the specimen containing the phosphate-containing polyanion is contacted with the amine-containing solid phase material to allow the phosphate-containing polyanion to bind to the amine-containing solid phase material.

Figure 48:
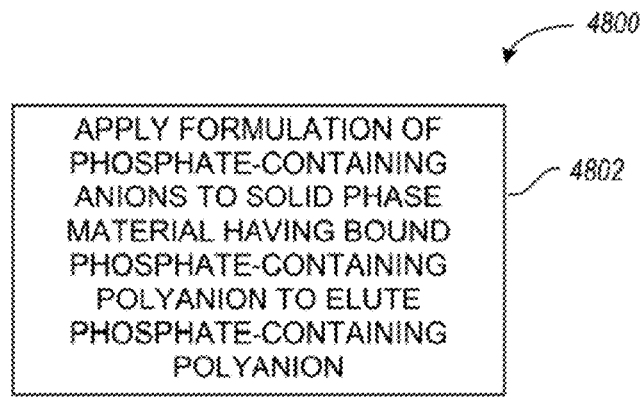
FIG. 48 is a flow diagram of an aspect of a method of processing a phosphate-containing polyanion specimen by a method such as that of FIG. 47 including eluting particle-bound phosphate-containing polyanion, according to one embodiment.

FIG. 48 shows a method 4800 for eluting the phosphate-containing polyanion from the amine-containing solid phase material in one illustrated embodiment.

A positively charged surface such as an amine-modified solid phase material, e.g., silica, may bind a polyanion such as a phosphate-containing polyanion. In particular, such a positively charged surface may bind nucleic acid. Typically releasing a phosphate-containing polyanion bound to such a positively charged surface would require ion exchange. However, elution of phosphate-containing polyanions may be accomplished more efficient by selecting and using appropriate anions.

At 4802, the formulation of phosphate-containing anions is applied to the amine-containing solid phase material to which the phosphate-containing polyanion is bound. Applying the phosphate-containing anion elutes the phosphate-containing polyanion. The phosphate-containing anionic formulation used to elute the phosphate-containing polyanion may include any phosphate anion having a structure suitable to compete with the phosphate moieties on the polyanion for binding to the amine-containing solid phase.

In a certain embodiments, the phosphate-containing polyanion is a nucleic acid, including DNA and RNA. While phosphate-containing anions in general may elute phosphate-containing polyanions from the amine-containing solid phase materials, use of nucleoside triphosphates may improve efficiency of release of nucleic acids by as much as ten-fold. Elution by nucleoside triphosphates may leave other polyanions lacking phosphate bound to the amine-containing solid phase material. This approach may be particularly useful when isolating nucleic acids from natural materials that have a high load of anionic proteins, anionic polysaccharides, or other polyanions. Nucleoside triphosphates suitable for elution of nucleic acids from the aminated surfaces may particularly include at least deoxyadenosine triphosphate, deoxyguanosine triphosphate, deoxycytidine triphosphate, and deoxythymidine triphosphate, adenosine triphosphate, guanosine triphosphate, cytidine triphosphate, and uridine triphosphate.

In certain embodiments, a kit may be suitable for use in methods for isolating. In certain embodiments, a kit may include an amine-containing solid phase material that has affinity for phosphate-containing polyanions such as nucleic acids. In certain embodiments, the kit may include instructions for using the kit contents to isolate phosphate-containing polyanions.

Figure 49:
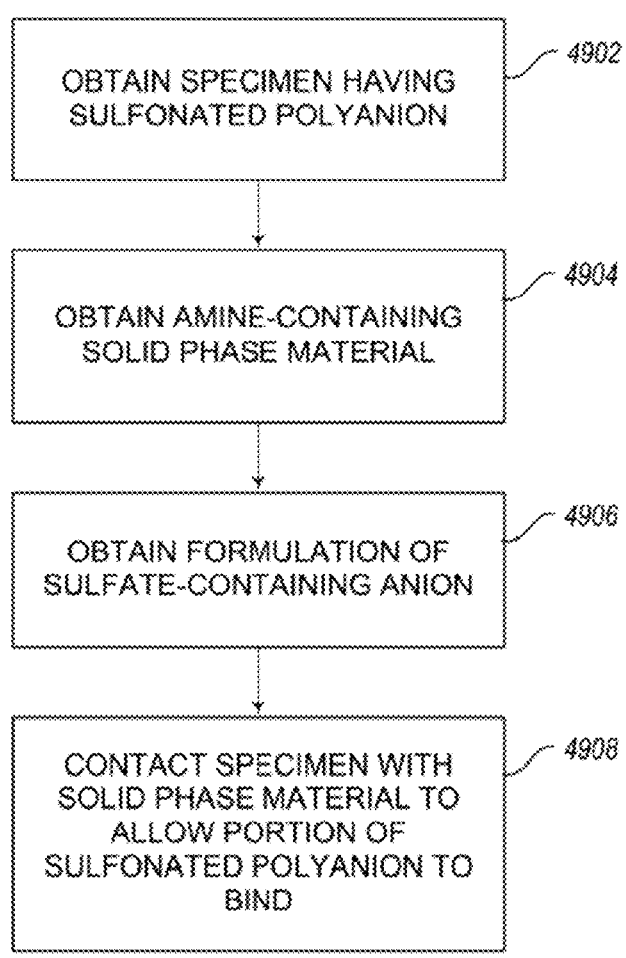
FIG. 49 is a flow diagram of aspects of a method of processing a sulfonate-containing polyanion using an amine-containing solid phase material, according to one embodiment.

FIG. 49 shows a method 4900 for isolating sulfonate-containing polyanions using an amine-containing solid phase material in one illustrated embodiment.

As discussed above, amine-containing solid phase materials may be used to isolate phosphate-containing polyanions such as nucleic acids. Natural materials may contain sulfonated polyanions in addition to the phosphate-containing polyanions. The negatively charged sulfonated polyanions will also bind to the positively charged amine-containing solid phase. In certain embodiments, it may be advantageous to remove bound sulfonated polyanions before isolating the phosphate-containing polyanions.

At 4902, a specimen having sulfonate-containing polyanions is obtained. In certain embodiments, this specimen may likely also have phosphate-containing polyanions. At a pH of around about 7, the sulfonate-containing polyanions have a negative charge. If present, phosphate-containing polyanions will also have a negative charge.

At 4904, an amine-containing or aminated solid phase material is obtained. At a pH of around about 7, the amine groups on the amine-containing solid phase material are positively charged. Thus, the positively charged amine-containing solid phase material will bind the negatively charged species in the specimen, including sulfonate-containing polyanions, as well as any phosphate-containing polyanions present in the specimen.

At 4906, a formulation of sulfate-containing anions is obtained. The formulation may include one or more of a variety of sulfate-containing anions. For example, such anions may include organic or inorganic sulfates.

At 4908, the specimen containing the sulfonate-containing polyanion is contacted with the amine-containing solid phase material to allow the sulfonate-containing polyanion to bind to the amine-containing solid phase material.

Figure 50:
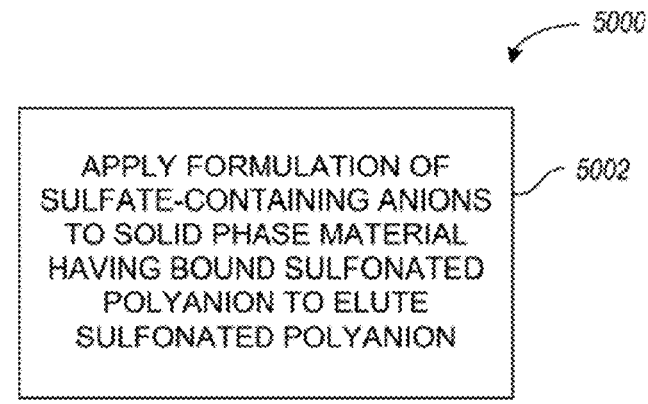
FIG. 50 is a flow diagram of an aspect of a method of processing a sulfonate-containing polyanion specimen by a method such as that of FIG. 49 including eluting particle-bound sulfonate-containing polyanion, according to one embodiment.

FIG. 50 shows a method 5000 for eluting the sulfonate-containing polyanion from the amine-containing solid phase material in one illustrated embodiment.

At 5002, the formulation of sulfate-containing anions is applied to the amine-containing solid phase material to which the sulfonate-containing polyanion is bound. Applying the sulfate-containing anion elutes the sulfonate-containing polyanion. The sulfate-containing anionic formulation used to elute the sulfonate-containing polyanion may include any sulfate anion having a structure suitable to compete with the sulfonate moieties on the polyanion for binding to the amine-containing solid phase.

Upon removal of the sulfonate-containing polyanion, phosphate-containing anions bound to the amine-containing solid phase may be advantageously eluted with a lower possibility of contamination of the isolated phosphate-containing polyanions by sulfate-containing polyanions.

Figure 51:
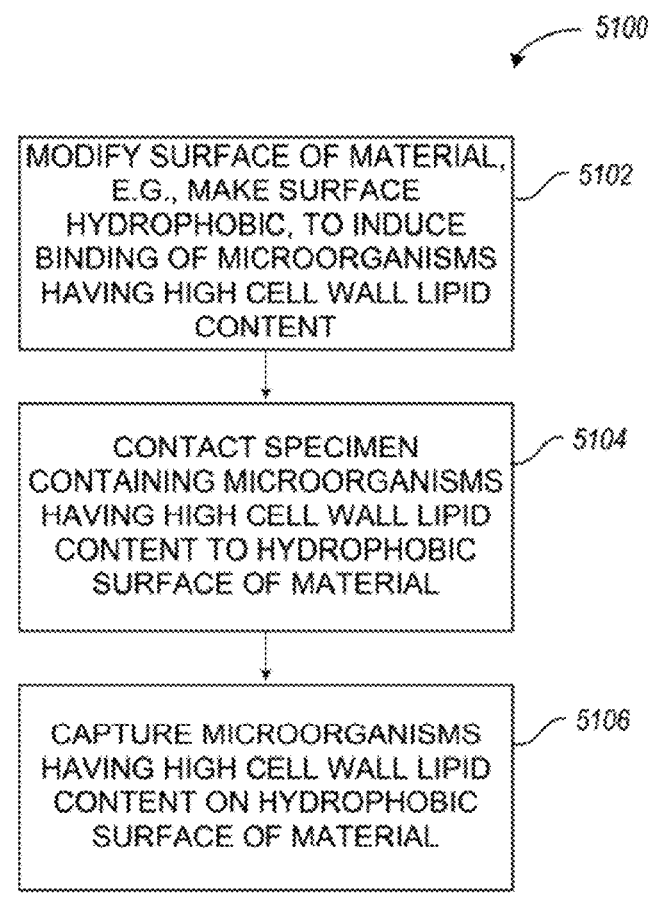
FIG. 51 is a flow diagram of a method of capturing a microorganism having a high content of cell wall lipid by a hydrophobic surface of a material, according to one embodiment.

FIG. 51 shows method 5100 for capturing microorganisms having high cell wall lipid content on a material having a hydrophobic surface according to one illustrated embodiment. Method 5100 may be useful in aspects of methods of lysing, extracting, capturing and isolating biological materials described elsewhere herein. Alternatively, method 5100 may be useful in combination with other approaches to the isolation of materials known and practiced in the art.

The outer surface of cell walls of microorganisms with high cell wall lipid content may include both hydrophobic and charge characteristics. For example, mycobacterial cell walls have both high lipid content and a net negative charge. Thus, *mycobacteria* are attracted to hydrophobic surfaces as well as to surfaces that have a positive charge. The interest in capturing microorganisms with high cell wall lipid content, particularly *mycobacteria*, is to isolate and further process DNA from these microorganisms once captured. However, various approaches to capturing such microorganisms present certain challenges. Solutions to such challenges are discussed below.

At 5102, a surface of a solid phase material is modified to make the surface hydrophobic in order to induce binding of a microorganism having a high cell wall lipid content to the surface. In this embodiment, the surface has no net charge.

At 5104, a specimen containing microorganisms having high cell wall lipid content contacts the hydrophobic surface of the solid phase material.

At 5106, the hydrophobic surface of the material captures microorganisms having high cell wall lipid content. In one embodiment, silica particles modified to have a hydrophobic surface with no charge were shown to bind *Mycobacteria bovis* cells from a suspension at high efficiency.

Figures 52, 53:
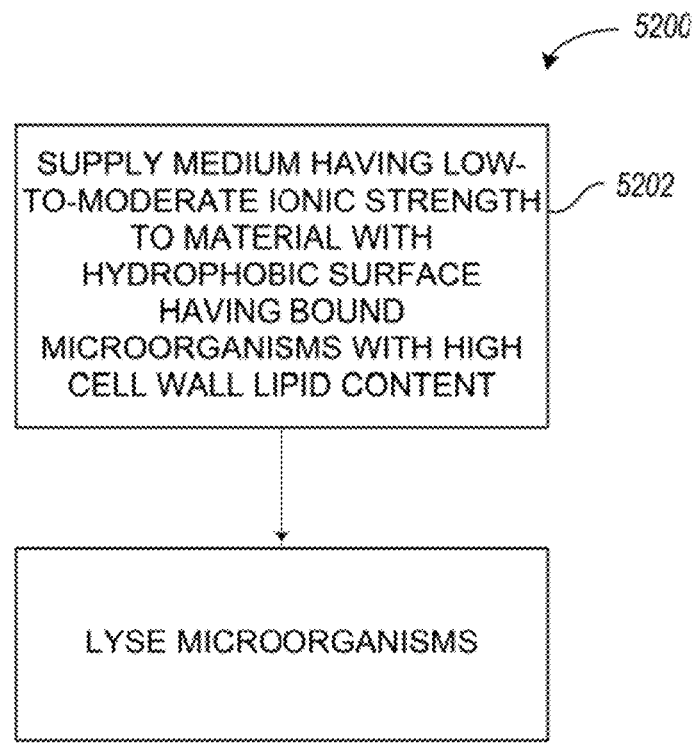
FIG. 52 is a flow diagram of a method of lysing a microorganism having a high cell wall lipid content captured by a hydrophobic surface of a material, according to one embodiment.
FIG. 53 is a flow diagram of a method of amplifying nucleic acid from a lysate of a microorganism having high cell wall lipid content capture by a hydrophobic surface of a material, according to one embodiment.

FIG. 52 shows a method 5200 of lysing in a suitable medium microorganisms captured on a hydrophobic surface in one illustrated embodiment.

At 5202, a medium having low-to-moderate ionic strength is supplied to a solid phase material having a hydrophobic surface to which is bound microorganisms with high cell wall lipid content.

At 5204, the bound microorganisms with high cell wall lipid content are lysed. At low-to-moderate ionic strength, DNA released from the cell is not bound to the hydrophobic surface of the solid phase material. The DNA is thus in a medium suitable for subsequent processing and analysis.

FIG. 53 shows a method 5300 of amplifying DNA in a lysate from a microorganism with high cell wall lipid content, e.g., by PCR, in one illustrated embodiment.

At 5302, DNA in a lysate from microorganisms having high cell wall lipid content is amplified, e.g., by PCR. The lysate is from microorganisms captured on a hydrophobic solid phase and lysed.

Figure 54:
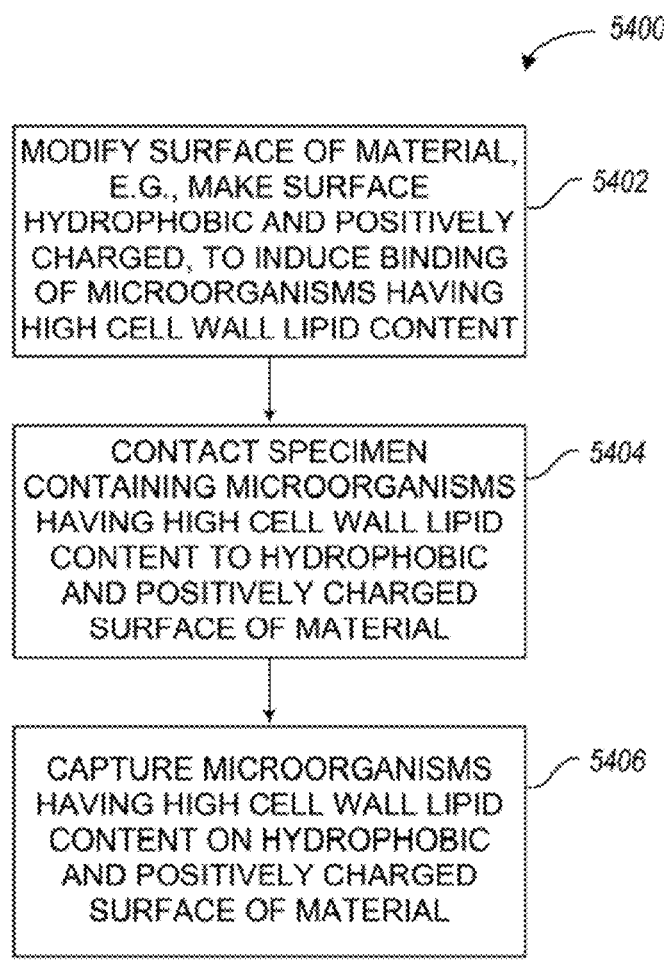
FIG. 54 is a flow diagram of a method of capturing a microorganism having a high content of cell wall lipid by a hydrophobic and positively charged surface of a material, according to one embodiment.
Figure 55:
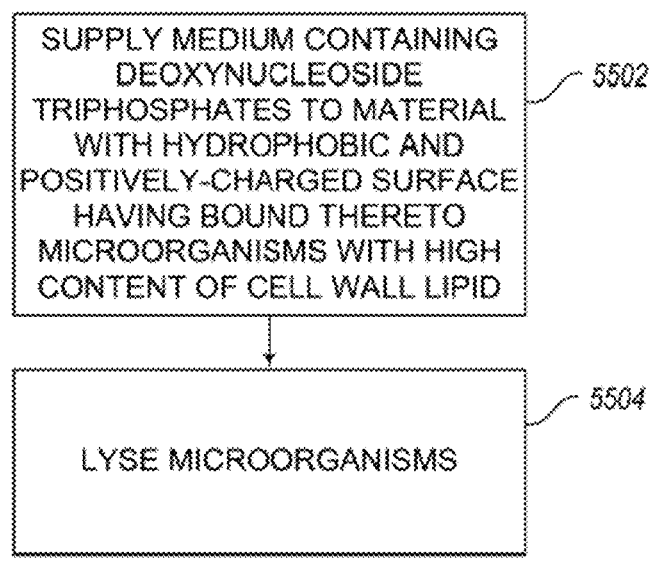
FIG. 55 is a flow diagram of a method of lysing a microorganism having a high cell wall lipid content captured by a hydrophobic and positively charged surface of a material, according to one embodiment.
Figure 56:
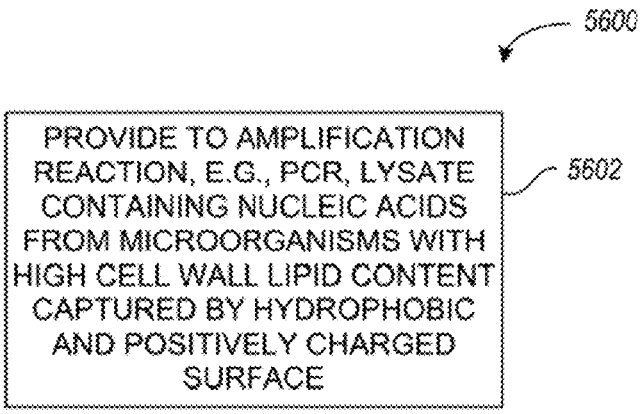
FIG. 56 is a flow diagram of a method of amplifying nucleic acid from a lysate of a microorganism having high cell wall lipid content capture by a hydrophobic and positively charged surface of a material, according to one embodiment.
Figure 57:
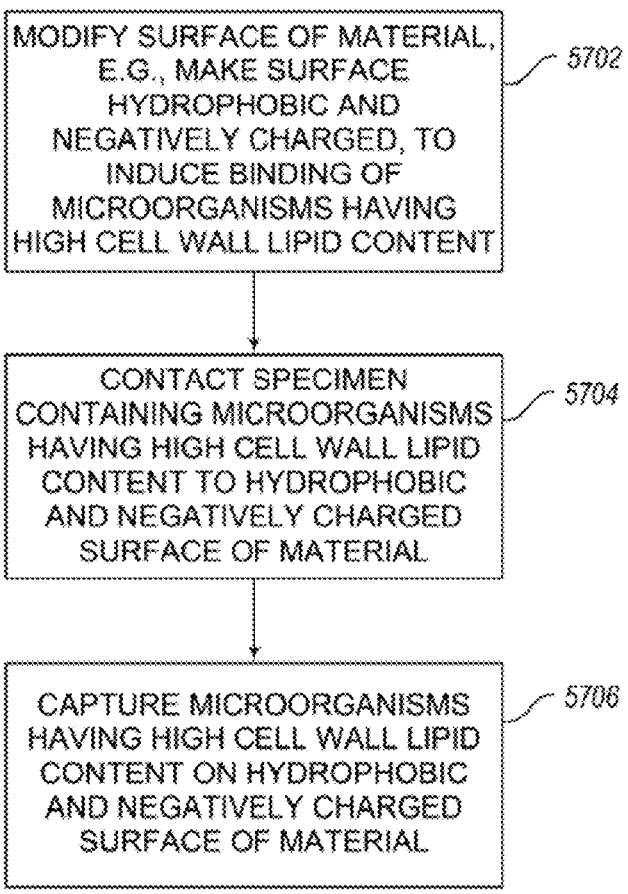
FIG. 57 is a flow diagram of a method of capturing a microorganism having a high content of cell wall lipid by a hydrophobic and negatively charged surface of a material, according to one embodiment.
Figure 58:
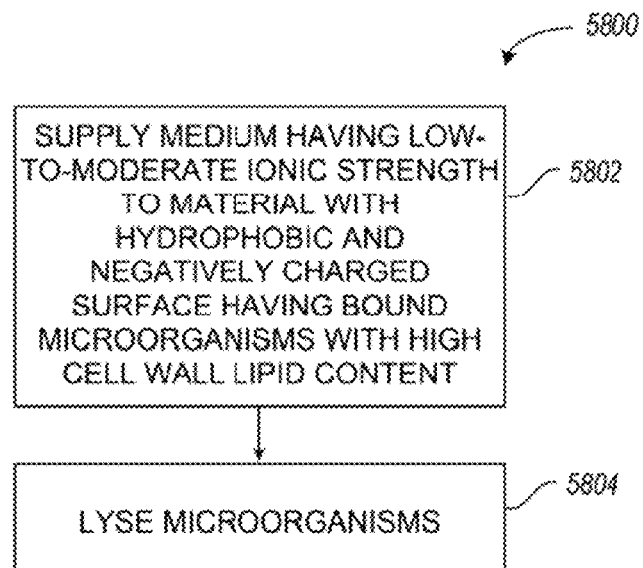
FIG. 58 is a flow diagram of a method of lysing a microorganism having a high cell wall lipid content captured by a hydrophobic and negatively charged surface of a material, according to one embodiment
Figure 59:
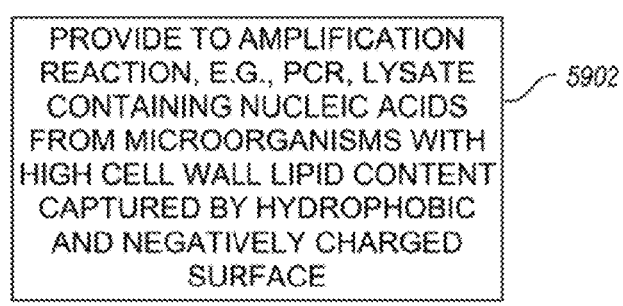
FIG. 59 is a flow diagram of a method of amplifying nucleic acid from a lysate of a microorganism having high cell wall lipid content capture by a hydrophobic and negatively charged surface of a material, according to one embodiment.
Figure 60:
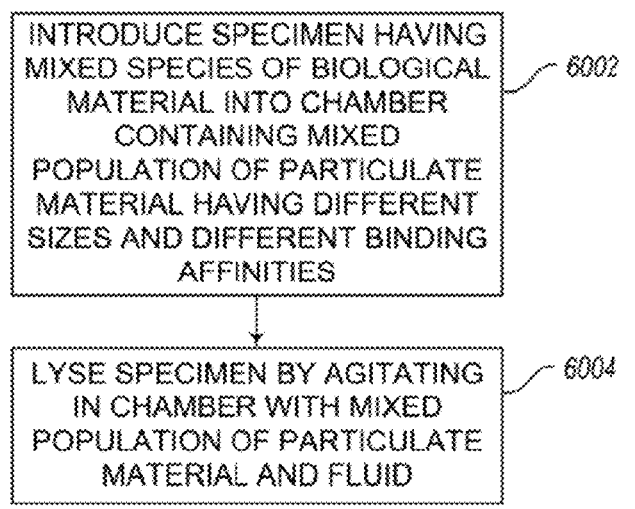
FIG. 60 is a flow diagram of a method of processing a biological material with a mixed population of particulate materials of different sizes, according to one embodiment.
Figure 61:
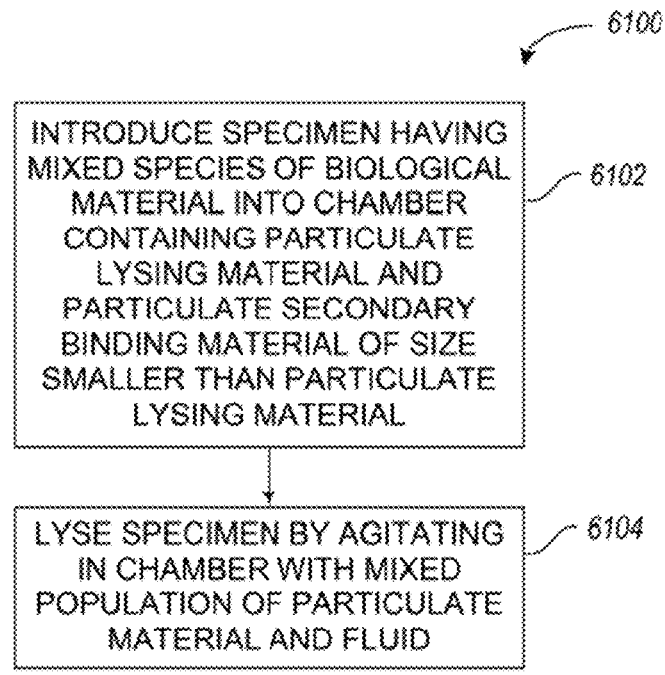
FIG. 61 is a flow diagram of a method of processing a biological material with a mixed population of particulate materials of different sizes, according to another embodiment.

FIG. 54 shows method 5400 for capturing microorganisms having high cell wall lipid content on a solid phase material having a hydrophobic and positively charged surface according to one illustrated embodiment. Method 5400 may be useful in aspects of methods of lysing, extracting, capturing and isolating biological materials described elsewhere herein. Alternatively, method 5400 may be useful in combination with other approaches to the isolation of materials known and practiced in the art.

At 5402, a surface of a solid phase material is modified to make the surface hydrophobic and positively charged in order to induce binding of a microorganism having a high cell wall lipid content to the surface. Surface modifications include reaction with polydiallyldimethylammonium chloride and other surface modifications to confer hydrophobicity and positive charge on the surface of the solid phase material. In another embodiment, the surface of the solid phase may be modified with an alkylamine compound. For example, silica bead surfaces may be modified with 3-aminopropyl silane. Such beads can effectively capture both *Mycobacteria bovis* and *Clostridium* cells from a sample.

At 5404, a specimen containing microorganisms having high cell wall lipid content contacts the hydrophobic and positively charged surface of the solid phase material.

At 5406, the hydrophobic surface of the material captures microorganisms having high cell wall lipid content.

FIG. 69 shows several preferred embodiments of solid phase beads modified with different molecules which may be used to bind to cells of different types.

FIG. 55 shows a method 5500 of lysing in a suitable medium microorganisms captured on a hydrophobic surface in one illustrated embodiment.

At 5502, a medium having deoxynucleoside triphosphates is supplied to a solid phase material having a hydrophobic and positively charged surface to which is bound microorganisms with high cell wall lipid content.

At 5504, the bound microorganisms with high cell wall lipid content are lysed. Deoxynucleoside triphosphate in the lysing medium competitively inhibits DNA binding to the surface of the solid phase material. Deoxynucleoside triphosphates in the lysate do not interfere with subsequent amplification reactions. The DNA is thus in a medium suitable for subsequent processing and analysis.

FIG. 56 shows a method 5600 of amplifying DNA in a lysate from a microorganism with high cell wall lipid content, e.g., by PCR, in one illustrated embodiment.

At 5602, DNA in a lysate from microorganisms having high cell wall lipid content is amplified, e.g., by PCR. The lysate is from microorganisms captured on a hydrophobic and positively charged solid phase and lysed.

FIG. 57 shows method 5700 for capturing microorganisms having high cell wall lipid content on a solid phase material having a hydrophobic and negatively charged surface according to one illustrated embodiment. Method 5400 may be useful in aspects of methods of lysing, extracting, capturing and isolating biological materials described elsewhere herein. Alternatively, method 5700 may be useful in combination with other approaches to the isolation of materials known and practiced in the art.

At 5702, a surface of a solid phase material is modified to make the surface hydrophobic and negatively charged in order to induce binding of a microorganism having a high cell wall lipid content to the surface under appropriate conditions.

At 5704, a specimen containing microorganisms having high cell wall lipid content contacts the hydrophobic and negatively charged surface of the solid phase material.

At 5706, the hydrophobic and negatively charged surface of the material captures microorganisms having high cell wall lipid content. The specimen is in a medium having high salt concentration and/or low pH. Under these conditions binding of the hydrophobic and negatively charged surface of the microorganism to the hydrophobic and negatively charged surface of the solid phase material is aided by bridging of the negatively charged groups via cations in solution as a result of the high salt concentration and/or the low pH.

FIG. 58 shows a method 5800 of lysing in a low ionic strength medium microorganisms captured on a hydrophobic and negatively charged surface of the solid phase material in one illustrated embodiment.

At 5802, a medium having low ionic strength is supplied to a solid phase material having a hydrophobic and negatively charged surface to which is bound microorganisms with high cell wall lipid content.

At 5804, the bound microorganisms with high cell wall lipid content are lysed. The low ionic strength during lysis inhibits binding of nucleic acid to the surface of the solid phase material and provides a medium suitable for subsequent amplification reactions, e.g., PCR.

FIG. 59 shows a method 5900 of amplifying DNA in a lysate from a microorganism with high cell wall lipid content, e.g., by PCR, in one illustrated embodiment.

At 5902, DNA in a lysate from microorganisms having high cell wall lipid content is amplified, e.g., by PCR. The lysate is from microorganisms captured on a hydrophobic and negatively charged solid phase and lysed.

In methods 5100 to 5900 the surfaces of the solid phase material includes surfaces of particulates, beads, membranes, flow channels and tubes, any of which may act to capture cells with high lipid cell wall content for subsequent lysis and release of nucleic acids.

*Mycobacterium tuberculosis* has cell walls that are over 60% lipid. Mycolic acids form a lipid shell around the cell. The cell walls include three main types of mycolic acids: alpha-, methoxy-, and keto-. Alpha mycolic acids comprise at least 70% of the mycolic acids present in the organism. The lipid chemistry of *M. tuberculosis* cell walls provides the basis for binding of the species to surfaces that are coated with diallyldimethylammonium chloride. Similar binding can be seen on silica beads that have been modified by reaction with various silanes to confer hydrophobicity or a combination of hydrophobicity and positive charge to the surface of the beads. The siloxol component of the silanes facilitates polymerization of monomers and coupling to a silica surface or other mineral oxide surfaces. There are many alkane and vinyl silanes that can confer hydrophobicity to the silica surface and there are many organic amino silanes that may be combined to achieve an optimum ratio of the two characteristics of hydrophobicity and charge that maximize affinity of *Mycobacteria*. In certain embodiments, surfaces that are at least primarily hydrophobic may be advantageous for the processing of nucleic acids, as such will limit the potential for the surfaces to bind nucleic acids once they have been released from cells.

FIG. 60 shows a method 6000 of obtaining a biological material of interest from a specimen in one illustrated embodiment.

At 6002, a specimen having a mixture of different species of biological materials is introduced into a chamber containing mixed population of particulate material having different sizes and different binding affinities for the different species of biological materials in the specimen.

At 6004, the specimen is lysed by agitating the specimen in the chamber with the mixed population of particulate material and a fluid.

FIG. 61 shows a method 6100 of obtaining a biological material of interest from a specimen in one illustrated embodiment.

At 6102, a specimen having a mixture of different species of biological materials is introduced into a chamber containing particulate lysing material having an affinity for the biological material of interest and particulate secondary binding material having affinity for one or more secondary biological materials other than the material of interest. The particulate secondary binding material is of a size smaller than the particulate lysing material. The particulate lysing material and the particulate secondary binding material may each include a plurality of beads. The particulate lysing material may include at least one of a plurality of ceramic beads, a plurality of glass beads, a plurality of zirconia beads, a plurality of silica beads, a plurality of sand, or a plurality of beads with a metal core coated by a material that facilitates binding of the biological material of interest. The particulate secondary binding material may include at least one of a plurality of ceramic beads, a plurality of glass beads, a plurality of zirconia beads, a plurality of silica beads, a plurality of sand, or a plurality of beads with a metal core coated by a material that facilitates binding of the biological material of interest. The biological material of interest may be a nucleic acid. Secondary biological materials may include materials that interfere with binding the biological material of interest by the particulate secondary binding material or materials that interfere with subsequent reactions with or analysis of the biological material of interest. The particulate secondary binding material may be include paramagnetic particle. Paramagnetic beads may be sequestered, thus providing a means for interfering reagents to be sequestered from the lysate during lysis of specimens or providing a means for subsequent extraction and analysis of a secondary analyte. The secondary binding material may include protein A, protein G, protein L, anti-albumin antibody, concanavalin A or titanium dioxide.

At 6104, the specimen is lysed by agitating the specimen in the chamber with the particulate lysing material, the particulate secondary binding material, and a fluid.

Figure 62:
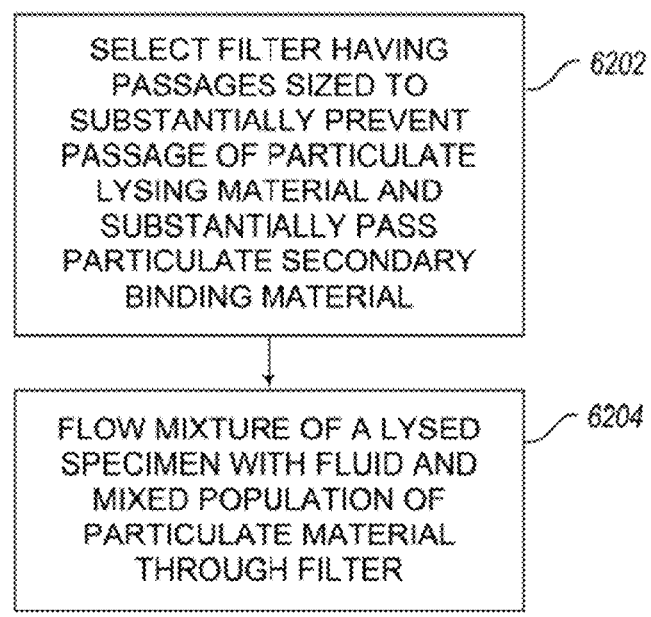
FIG. 62 is a flow diagram of a method of processing a biological material with a mixed population of particulate materials of different sizes using a filter to separate particles by size, according to one embodiment.

FIG. 62 shows a method 6200 of obtaining a biological material of interest that includes further aspect of method 6100, in one illustrated embodiment.

At 6202, a filter is selected having passages of a size to substantially pass the particulate secondary binding material and to substantially prevent passage of the particulate lysing material.

At 6204, a mixture of lysed specimen combined with the mixed population of particulate matter and fluid is flowed through the filter.

In one embodiment, the particulate lysing material binds the biological material of interest and the particulate secondary binding material binds secondary biological material(s) that are not of interest or that may interfere with binding or subsequent reactions of the biological material of interest. By binding secondary biological material(s) to the particulate secondary binding material and then passing it through a filter that retains the particulate lysing material, the secondary binding material(s) may be physically removed from the biological material of interest and discarded. Alternatively, the secondary biological material(s) may be retained for some other use. The smaller size of the particulate secondary binding materials not only allows their separation from the larger particulate lysing material but also gives them greater surface area and thus greater binding capacity per unit mass. Although the particulate secondary binder materials are small relative to the particulate lysing materials, they are large enough and have sufficient inertia to prevent their binding to the particulate lysing material during agitation and lysis of the specimen. Low binding beads (OPS Diagnostics, Lebanon, N.J.) are commercially available silica or zirconia beads that have been overcoated. Such beads are hydrophobic and have a low binding affinity for DNA. Such beads have been tested for their ability to bind biological materials, such as lipids or proteins, which may interfere with binding of nucleic acids to zirconia beads. In certain embodiments, particulate lysing materials may be beads having a diameter of 50-250 µm. These beads may be retained by a filter or mesh. Using particulate secondary binding beads smaller than the pore size of the filter or mesh allows them to be discarded with the lysate.

Figure 63:
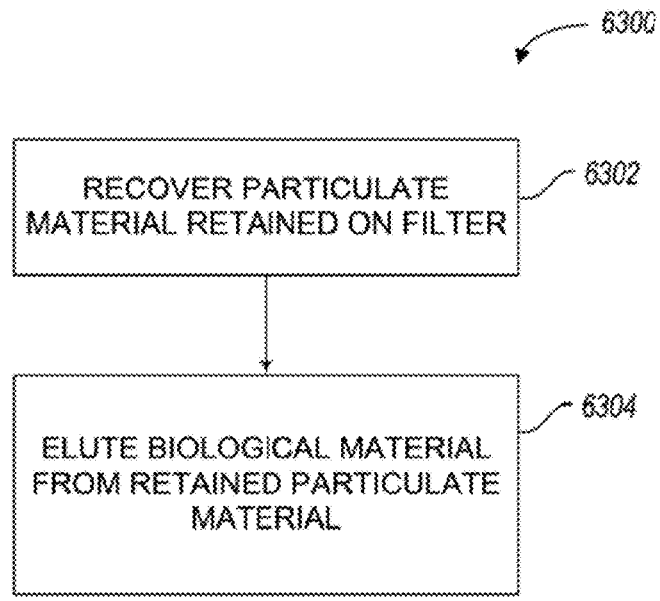
FIG. 63 is a flow diagram of a method of processing a biological material with a mixed population of particulate materials of different sizes using a filter to separate particles by size, according to another embodiment.

FIG. 63 shows a method 6300 that includes a further aspect of methods 6000 to 6200 in one illustrated embodiment.

In 6302, a particulate material retained on the filter is recovered.

In 6304, biological material is eluted from the particular material retained on the filter.

Figure 64:
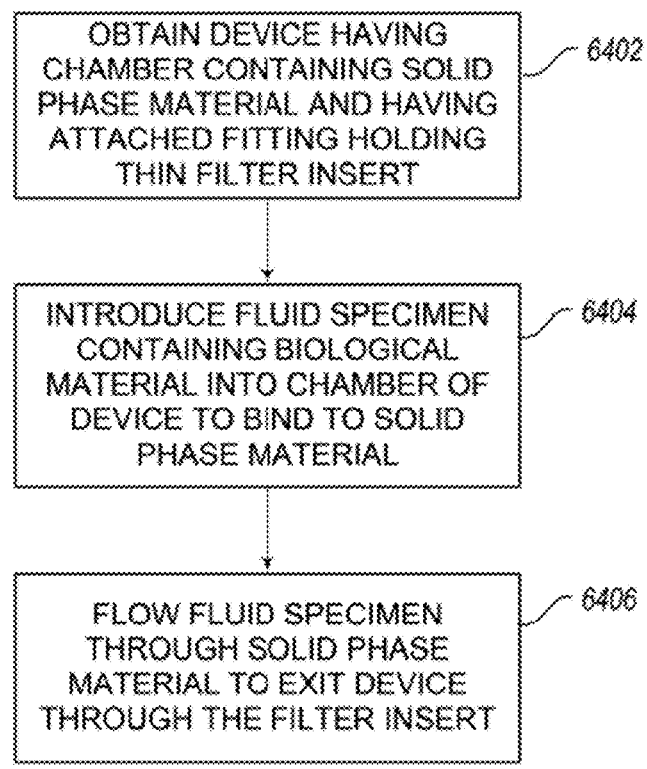
FIG. 64 is a flow diagram of aspects of a method of processing a biological material on a solid phase at high flow and low pressure, according to one embodiment.

FIG. 64 shows a method 6400 for rapidly processing and capturing a biological material in one illustrated embodiment.

At 6402, a device having a chamber containing a solid phase material and an attached fitting holding a thin filter insert is obtained. The pore or mesh size of the filter and the thickness are suitable to allow rapid flow at low pressure. Elements to retain particulate materials in such device typically limit flow through the device. In one embodiment, the device has a filter or mesh having a thickness of 0.002"-0.003". Devices with thicker such elements often provide slow and typically require pressure. Such retention elements may often include frits, such as glass fits, or dense filters.

Rapid flow and low pressure are advantageous in that procedures can be completed in less time, pumps and fluidic systems are not required to produce high pressure, and fluidic components which cannot withstand high pressure may be used. By rapid flow or substantially uninhibited flow or uninhibited flow is meant a flow rate of greater than about 0.1 ml/min and, more preferably, greater than about 1 ml/min. By low pressure or low operating pressure is meant a pressure less than about 200 psi and, more preferably less than about 100 psi. Such pressures to induce flow can readily be applied with a syringe, pipettor, peristaltic pump, or syringe pump.

At 6404, a fluid specimen containing a biological material is introduced into the chamber of the device to bind to the solid phase material.

At 6406, the fluid specimen flows through the solid phase material, exiting the device through the filter insert. The device with the filter insert allows rapid flow.

Figure 65:
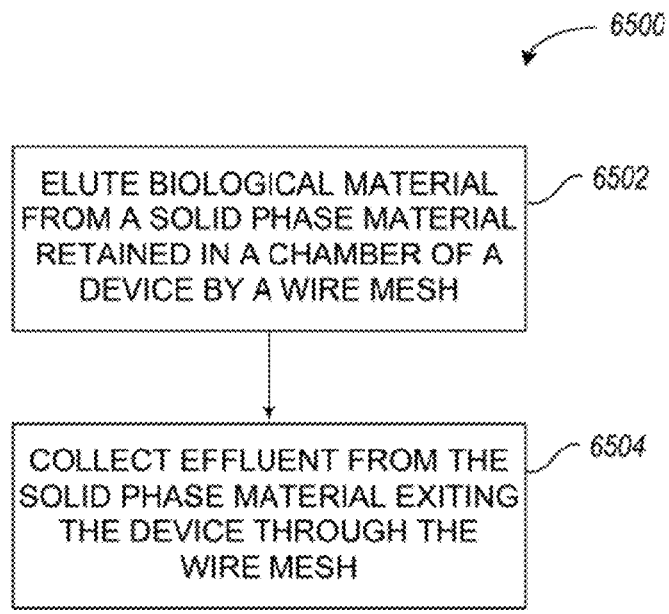
FIG. 65 is a flow diagram of further aspects of a method of processing a biological material on a solid phase at high flow and low pressure as in FIG. 56, according to another embodiment.

FIG. 65 shows a method 6500 of recovering biological material in one illustrated embodiment.

At 6502, biological material is eluted from a solid phase material retained in a chamber of a device by a thin filter or wire mesh. Elution may be carried out at low pressure while allow rapid flow.

At 6504, the effluent is collected from the solid phase material exiting the device through the thin filter or wire mesh.

In one embodiment, proteins or peptides may be captured by solid phase material contained in a chamber of a device that allows high flow rate and low pressure in comparison to other devices known in the art. In certain embodiments, the solid phase material may be in the form of a particulate or bead. In certain embodiments, such a device may have a thin filter or mesh material.

In certain embodiments, the chamber of such a device may contain solid particulates having physical characteristics such that they do not pack as densely as certain materials known in the art, such as agarose beads or silica gel. In certain such embodiments, fluids may flow around the particulates relatively unimpeded yet may have sufficient opportunity to interact with the surfaces of the particulates to allow proteins or other biomolecules or biological materials to interact with binding ligands on the surfaces of the particulates. The particulates may comprise materials which may be surface-modified with capture ligands to bind proteins or other biomolecules or biological materials. In certain embodiments, particulates may include metal oxides, ceramics, or other such relatively non-compressible materials. In certain such embodiments, particulates may include silicon dioxide, zirconia dioxide, or titanium dioxide. In other embodiments, particulates may include silica gel, sepharose, or agarose. Such particulate materials may pack more densely than metal oxides, ceramics, and the like. Such relatively compressible particulate materials may impede flow of fluid through such a device. The particulate material may also comprise mixtures of more than one material such as a mixture of silicon dioxide and zirconia dioxide. In certain embodiments, particulates may have a spherical or an approximately spherical shape. In other embodiments, particles may have an irregular or random shape, such as that of crushed silica or glass shards.

The particulates may be of any size. Size is generally selected to provide a bed of particles that allows a sufficiently high flow rate at low pressure. Generally, larger particulates tend to allow flow at low pressure that is greater than that allowed by smaller particulates. On the other hand, smaller particulates have larger surface area and thus higher binding capacity and more rapid binding kinetics than larger particulates. Particle size is thus chosen to optimize operational characteristics, that is, to achieve high flow rate at low pressure and to provide sufficient binding capacity and kinetics to allow adequate protein or biomolecule capture. The device includes a filter or mesh material to trap the particulates in the chamber. The filter or mesh material has pores or openings selected to preclude passage of the particulate material and also to allow rapid flow at low pressure. Prior art devices typically include frits, e.g., glass frits, to retain solid particulates in chambers. Such devices tend to have slow flow rates, and the pores in the frits also tend to clog during use. In certain embodiments of the device disclosed herein, the filter or mesh is selected to have a pore size and shape such that the particulate material does not readily clog the filter or mesh. For example, spherical particles may more easily clog round pores than square pores in the filter or mesh material.

The filter or mesh utilized in the device disclosed herein may be of any solid material, including but not necessarily limited to plastic (e.g., nylon, polyester, polyethylene, and Teflon), metal, or ceramic. In certain embodiments, the filter or mesh material may be stainless steel. Filter or mesh materials may be solid materials having holes or pores or may be woven from strands of the material. In a woven filter or mesh, the weave pattern may have any of a variety of patterns known in the art. Different weave patterns may be chosen, for example, to achieve different pore size and geometry to achieve adequate retention of the particulate material in the chamber while allowing high flow rate at low pressures.

In certain embodiments, the particulate material may comprise gold. Solid gold particles or particles of a different material but coated with gold may be used. Gold particles can readily be surface-modified with a variety of ligands of different chemical structures, for example, by binding the ligands using thiol monolayer technology as is well known in the art.

Many particulate materials are known to bind nucleic acids without surface chemical modification. Silica materials are widely used in the art for such purposes. Particulate materials for use in the devices disclosed herein may have surfaces that are modified to bind particular biological materials. Such surface modifications may be carried out by a variety of methods well known in the art. Such modifications may achieve immobilization of binding ligands on the surfaces of the particles. Such binding ligands may be chosen to selectively bind particular biological materials. Without limitation, the following ligand binding pairs may be incorporated on the surface of the particulates to capture proteins and/or other biological molecules or materials.

| Surface-bound ligand | Binding Partner |
|---|---|
| Nickel chelates | His-tagged protein or peptide |
| Glutathione | GST-tagged protein or peptide |
| Biotin | Streptavidin (SA) and SA-labeled protein and peptide |
| Avidin, streptavidin and analogs | Biotin-labeled protein and peptide |
| Streptavidin-binding peptide | Streptavidin (SA) and SA-labeled protein and peptide |
| Calmodulin-binding protein | Calmodulin |
| Antibodies | Antigens: Small molecules, peptides, proteins, nucleic acids, polysaccharides |
| Antigens | Antibodies |
| Protein G | Immunoglobulins |
| Protein A | Immunoglobulins |
| Protein L | Immunoglobulins |
| Cibachron Blue | Albumin |
| Sulfate | Albumin |
| Intercalators (e.g., ethidium bromide) | Double-stranded DNA, RNA/DNA heteroduplexes |
| Sybr Green I | Double-stranded DNA |
| Sybr Green II | Single-stranded DNA & RNA |
| Maltose | Maltose binding protein |
| 9-mer peptide (DYKDDDDK (SEQ ID NO: 1)) | FLAG |
| 10-mer peptide (EQKLISEEDL (SEQ ID NO: 2)) | MYC |
| Concanavalin A | Glycoproteins and carbohydrates |
| Benzylguanine | SNAP-tag (20 kDa mutant of the human DNA repair protein $O^6$-alkylguanine-DNA alkyltransferase (hAGT) |
| Enzyme inhibitor | Enzyme |

Additional binding pairs are well known in the art. Affinity tags for protein purification are reviewed in Lichty, et al. (Lichty, J. J., et al., Protein Expr. Purif., 41(1):98-105, 2005), the entirety of which is incorporated herein by reference.

In certain embodiments the surface-bound ligand and the binding partner become bound covalently. For example, when the surface-bound ligand is an enzyme suicide inhibitor, a covalent bond is often formed when the enzyme binds the inhibitor. Similarly, when the SNAP-tag binds to benzylguanine, the SNAP-tag enzyme becomes covalently coupled. In such cases, a linker can optionally be used to tether the surface-bound ligand to the surface which contains a cleavable group. In this case, the captured protein of peptide can be eluted by cleaving the cleavable group. Examples of cleavable groups include disulfides, which can be cleaved, for example, by dithiothreitol and ester bonds which can be cleaved by acids (low pH). Cleavable groups can also be photolabile. For example, substituted 3-nitro-2-naphthalenemethanol groups can be incorporated into the linker and readily cleaved to allow elution using 380 nm wavelength electromagnetic radiation (light).

In another embodiment the surface bound ligand may be attached to the surface of beads by a linker comprising oligonucleotides. One oligonucleotide having a specific sequence may be attached to the surface of the bead and a second oligonucleotide which is at least partially complementary to the first oligonucleotide may be attached to the ligand. Under the proper conditions of temperature, pH, and solution chemistry the two oligonucleotides may bind to one another and effectively link the ligand to the surface. In this embodiment, following binding of the protein, nucleic acid, or peptide to the bead surfaces, the bound molecules can be eluted by subjecting the beads to conditions such as low ionic strength or high temperature, which cause the two oligonucleotides to dehybridize or melt.

In certain embodiments particulate material may be modified to provide at its surface a positive charge (e.g., by surface modification with amine-containing moieties). In certain such embodiments, particulate materials may be used to bind to negatively charged proteins or other biomolecules or biological materials. In other embodiments, the surface may be modified to have negatively charged groups (e.g., carboxylic acids, sulfates, or phosphates). In certain such embodiments, particulate materials may be used to bind to positively charged proteins or other biomolecules or biological materials.

In certain embodiments, particulate material may be modified to contain pores in its surface. In certain such embodiments, particulate material may be used to segregate small and large molecules (size with respect to the pore size). Thus, for example, such pore-containing particulates in a chamber may be used to retain small-sized biomolecules and allow large-sized biomolecules to pass through the chamber.

Figure 68:
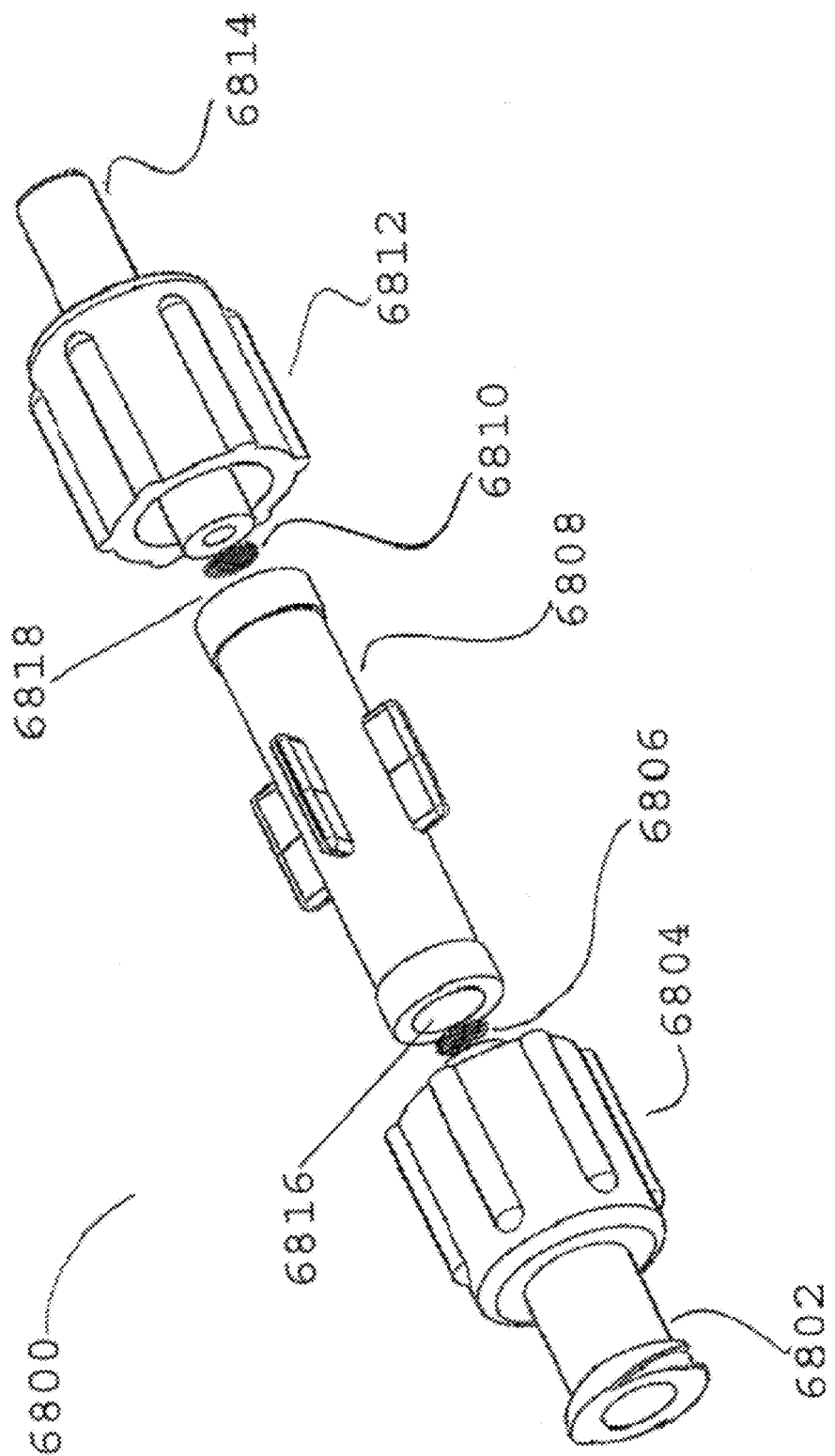
FIG. 68 is an exploded isometric view of a device for capturing a biological material from a fluid specimen according to one illustrated embodiment.
Figure 69:
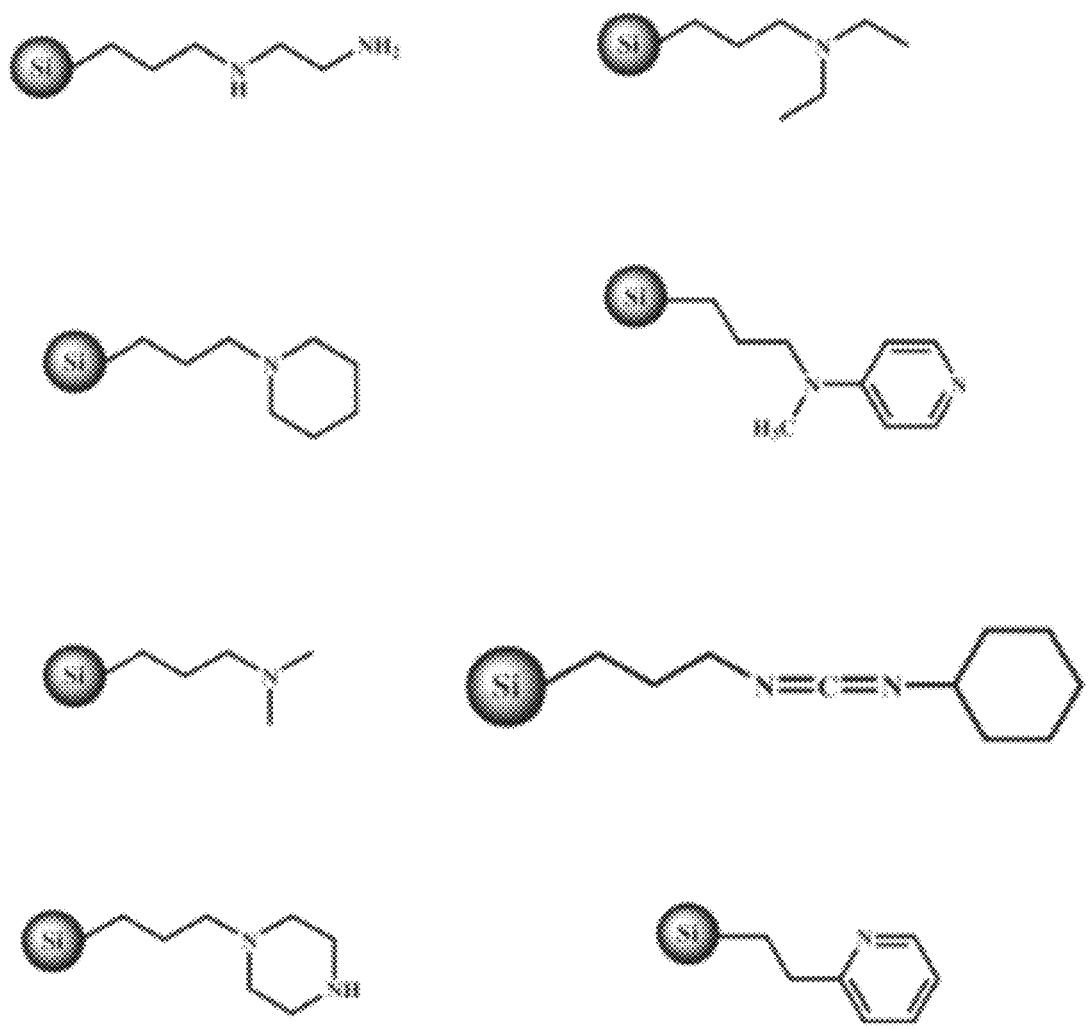
FIG. 69 is a chart showing several silica beads modified with different chemical moieties which can be employed in many different embodiments.

FIG. 68 shows a device 6800 for capturing a protein or other biomolecule or biological material from a fluid specimen at a high flow rate and a low operating pressure according to one illustrated embodiment.

In this one illustrated embodiment, the particulate material is contained in a chamber or cartridge 6808 having an entrance port 6816 and an exit port 6818. A filter or mesh material 6810 is positioned at the exit port 6818 and optionally a filter or mesh material 6806 is positioned at the entrance port 6816 to retain the particulate material in the chamber 6808. The chamber 6808 may be in the form of a cylinder or any other shape which facilitates high flow rate and low pressure flow of fluids through the chamber and achieves approximately homogeneous flow around the particulates. Device 6800 further includes inlet cap 6804 with inlet fitting 6802 and outlet cap 6812 with outlet fitting 6814. Inlet cap 6804 is inserted into entrance port 6816 of chamber 6808. Outlet cap 6812 is inserted into outlet port 6818 of chamber 6808.

In certain embodiments, the chamber of the device 6800 for capturing a protein or other biomolecule or biological material may be the same chamber containing a micromotor and an impeller used for lysing cells and tissues as described elsewhere herein. In such embodiments, the particulates used for lysing and the particulates used for capture of proteins and/or other biomolecules on biological materials may be the same. Alternatively, different particles may be employed to achieve lysis and capture.

In certain embodiments, the chamber for capture of the protein or other biomolecules or biological materials may be separate from the device used for cell lysis. In certain such embodiments, the capture cartridge may be placed downstream from the lysis cartridge. In certain other such embodiments, the capture cartridge may optionally be placed upstream from the lysis device.

In certain embodiment, binding cartridges may be placed both upstream and downstream from the lysis cartridge. In certain such embodiments, the configuration may be advantageously used, for example, for removal of interfering substances by the upstream binding cartridge and capture of proteins or other biomolecules or biological materials by the downstream cartridge.

In certain embodiments, cartridges or chambers of the device described herein may be fluidly connected to one another by tubing. In such embodiments, flow may thus occur from one cartridge to another. In certain such embodiments, fluid may pass in one direction only. In other such embodiments, fluid may flow successively in opposite directions such that the fluid may pass through the cartridge(s) multiple times.

In one embodiment the chamber for capture of nucleic acids is separate from and downstream of the chamber for lysis. In this example the fluid sample is flushed through the lysis chamber and through the capture chamber multiple times. It was demonstrated that DNA and/or RNA from the lysed cells is effectively captured upon its first pass through the capture chamber and does not pass through the lysis chamber on subsequent flushing steps. It was shown that this procedure effectively limits any shearing of the DNA or RNA into smaller fragments.

In an alternative embodiment the sample is flushed multiple times through the lysis chamber to effectively shear the DNA or RNA into smaller fragments. It was shown that the degree to which the DNA or RNA is thus sheared can be affected and controlled, for example by the number of flushes through the chamber, the flow rate through the chamber, the speed of the motor, and the size of the lysing beads.

In the embodiments disclosed herein for capturing his-tagged proteins or peptides, the particulate material is modified with a chelator bound to nickel. Examples of chelating groups include, without limitation, iminodiacetic acid (IDA), nitriloacetic acid (NTA), and tris(carboxymethyl)-ethylenediamine (TED).

In certain embodiments, following capture of the protein or other biomolecule or biological material, the particulate material may optionally be washed to remove unwanted chemicals and/or cellular debris. In certain such embodiments, following the optional wash, the captured protein or other biomolecule or biological material may be eluted from the particulate material by flowing an elution buffer through the chamber. The elution buffer may comprise chemicals which disrupt the binding of the biomolecule or other biological material to the surface-bound ligand. In certain embodiments, elution buffers may advantageously have a pH less than 6.0. In certain embodiments, the buffer may include imidazole for eluting his-tagged protein or peptide from nickel chelate ligand. In other embodiments, the buffer may include urea and have a low pH for eluting antibodies from antigen ligands and for eluting immunoglobulin from protein G, protein L, or protein A ligands. Buffer solutions for eluting proteins and other biomolecules or biological materials are well known in the art.

In further embodiments, when nickel chelators are employed to capture his-tagged proteins or peptides, the elution buffer may include ethylenediaminetetraacetic acid (EDTA). In certain such embodiments, the EDTA may have a higher affinity for nickel than does the capture ligand and may thus effectively compete for nickel atoms and release the his-tagged protein or peptide from the particulate material.

Figure 66:
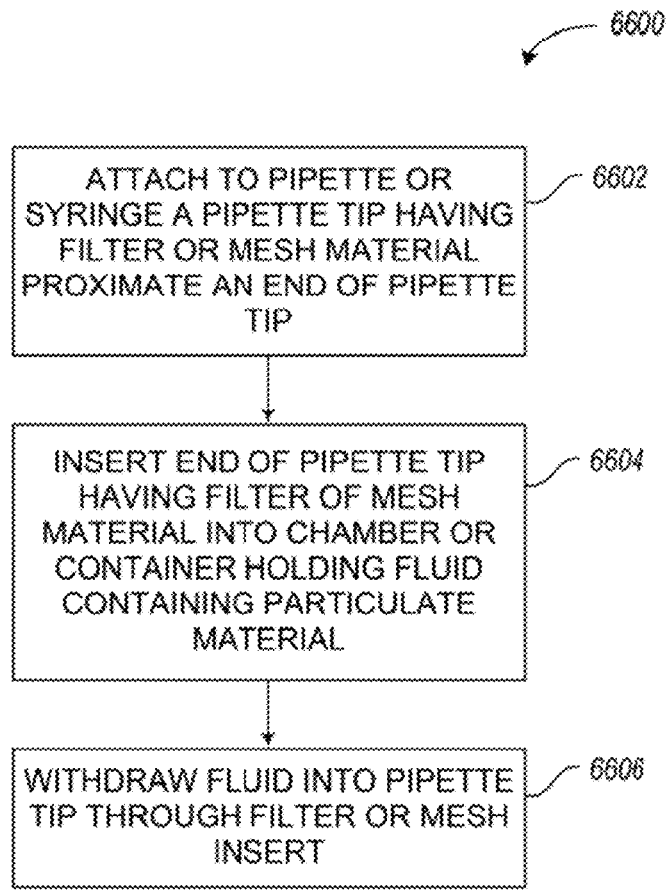
FIG. 66 is a flow diagram of aspects of a method of processing a fluid containing a particulate material, according to one embodiment.

FIG. 66 shows a method 6600 for withdrawing samples for particulate-containing specimens in one illustrated embodiment.

At 6602, a pipette tip having a filter or mesh material proximate an end of the pipette tip is attached to a pipette or syringe. The filter or mesh material may be inserted in the pipette tip or it may be inserted in a fitting that attaches to the pipette tip, as shown in FIGS. 67A and 67B.

At 6604, the end of the pipette tip having the filter or mesh material is inserted into a chamber or container holding a particulate-containing specimen.

At 6606, fluid is drawn from the chamber or container into the pipette tip through the filter or mesh insert. This device may be used to remove particulates from a specimen while withdrawing the specimen from a container or well. This device can be used, for example, to process samples that have been lysed in a non-flow through mode. After completion of the lysis, the soluble materials can be withdrawn into the pipette tip while the particulates may be caught by the filter or mesh.

Figure 67A:
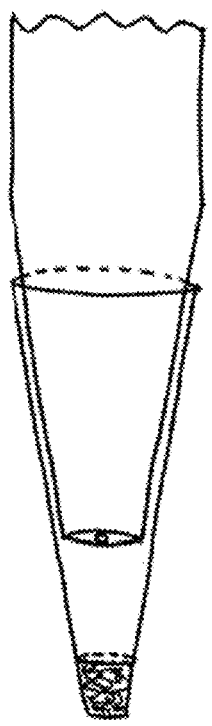
FIG. 67A is a pipette tip device for processing a fluid containing a particulate material, according to one illustrated embodiment.
Figure 67B:
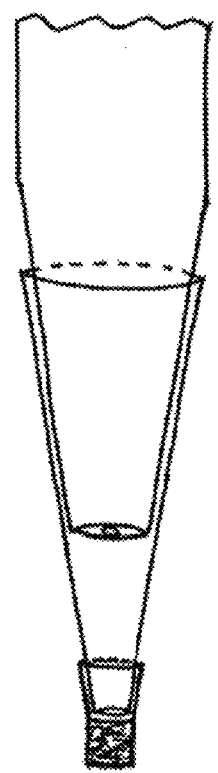
FIG. 67B is a pipette tip device for processing a fluid containing a particulate material, according to another illustrated embodiment.

FIG. 67A shows one illustrated embodiment of a pipette tip for use in method 6600 in one illustrated embodiment. The filter or mesh material is included within the pipette tip.

FIG. 67B shows another illustrated embodiment of a pipette tip for use in method 6600 in one illustrated embodiment. The filter or mesh material is included within a separate hold that may be affixed to a standard pipette tip before use.

The various embodiments described above can be combined to provide further embodiments. U.S. provisional patent application Ser. No. 61/020,072 filed Jan. 9, 2008; International Patent Application Serial No. PCT/US2009/030622 filed Jan. 9, 2009 and published as WO2009/089466; U.S. provisional patent application Ser. No. 61/117,012 filed Nov. 21, 2008; U.S. provisional patent application Ser. No. 61/220,984 filed Jun. 26, 2009; U.S. nonprovisional patent application Ser. No. 12/732,070 filed Mar. 25, 2010; U.S. provisional patent application Ser. No. 61/317,604 filed Mar. 25, 2010; U.S. nonprovisional patent application Ser. No. 12/823,081 filed Jun. 24, 2010; U.S. provisional patent application Ser. No. 61/427,045 filed Dec. 23, 2010; and U.S. provisional patent application Ser. No. 61/444,607 filed Feb. 18, 2011 are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The lysis and DNA extraction systems can be integrated with other components and functions. This is especially true of pumps and valves that further enable integration of waste reservoirs, wash reservoirs and functions, chambers for sample or specimen introduction, elution buffer chambers and functions, chambers and functions for amplification and detection. All of these structures and functions can be integrated into a disposable container or cartridge that includes the bead beating function for either lysis or analyte extraction or both. Integrating these structures and functions into a disposable unit has practical advantages for point-of-care and point-of-use diagnostic applications. Integrating these structures functions into a disposable unit has practical advantages for point-of-care and point-of-use diagnostic applications.

What is claimed is:

1. A flow-through device for capturing a biological material from a fluid specimen and lysing the fluid specimen, the device comprising:
   a first chamber containing:
   a portion of the fluid specimen;
   a solid phase material retained in the first chamber, the solid phase material having an affinity for the biological material in the fluid specimen;
   wherein the first chamber comprises:
   an inlet opening allowing flow of the fluid specimen into the first chamber;
   a first fitting attached to the inlet opening of the first chamber, the first fitting having a first thin filter insert that retains the solid phase material while allowing rapid flow of the fluid specimen at low pressure;
   an outlet opening allowing flow of the fluid specimen out of the first chamber; and
   a second fitting attached to the outlet opening of the first chamber, the second fitting having a second thin filter insert that retains the solid phase material while allowing rapid flow of the fluid specimen at low pressure; and a second chamber fluidly coupled to the first chamber, the second chamber containing:
a portion of the fluid specimen;
wherein the second chamber comprises:
an impeller which in use imparts rotational motion to the fluid specimen to mechanically lyse the fluid specimen.

2. The device of claim 1 wherein the second chamber is connected to the inlet opening of the first chamber.

3. The device of claim 1 wherein the second chamber is connected to the outlet opening of the first chamber.

4. The device of claim 1 wherein the solid phase material has an affinity for at least one selected from the group consisting of a nucleic acid, a protein, a polypeptide, a His-tagged protein, a His-tagged polypeptide, a GST-tagged protein, a GST-tagged polypeptide, streptavidin, biotin, calmodulin, an antigen, an antibody, an immunoglobulin, albumin, DNA, RNA, double stranded DNA, an RNA/DNA heteroduplex, maltose binding protein, FLAG-tagged protein, FLAG-tagged polypeptide, MYC-tagged protein, MYC-tagged polypeptide MYC, a glycoprotein, a SNAP-tag, an enzyme, a lipid-containing biological material, a glycosylated protein, a phosphorylated protein, and a microorganism having a high cell wall lipid content.

5. The device of claim 1 wherein the solid phase material has an affinity for more than one biological material.

6. The device of claim 1 wherein the solid phase material is a particulate or a bead.

7. The device of claim 6 wherein the particulate or bead has a diameter or lateral dimension of at least 10 µm.

8. The device of claim 1 wherein the solid phase material comprises at least one of a plurality of ceramic beads, a plurality of glass beads, a plurality of zirconia beads, a plurality of gold beads, a plurality of gold-coated beads, a plurality of silica beads, a plurality of sand, a plurality of beads with a metal core coated by a material that facilitates binding of the biological material, a plurality of mineral oxide beads coated with silane compounds to impart hydrophobicity and/or positive charge, and a plurality of paramagnetic beads.

9. The device of claim 1 wherein the first and second thin filter inserts have a pore size between about 10 µm and about 200 µm.

10. The device of claim 1 wherein the first and second thin filter inserts are wire mesh inserts.

11. The device of claim 1 wherein the first and second thin filter inserts are plastic mesh inserts.

12. A method of capturing a biological material from a fluid specimen and lysing the fluid specimen, the method comprising:
introducing the fluid specimen containing the biological material into a flow-through device comprising a first chamber, the first chamber containing a solid phase material retained in the first chamber, the solid phase material having an affinity for the biological material; the first chamber having an inlet opening and an outlet opening, the inlet opening and the outlet opening allowing flow of the fluid specimen into and out of the first chamber, the first chamber further having a first fitting attached to the inlet opening of the first chamber, the first fitting having a first thin filter insert that retains the solid phase material while allowing rapid flow of the fluid specimen at low pressure, the first chamber further having a second fitting attached to the outlet opening of the first chamber, the second fitting having a second thin filter insert that retains the solid phase material while allowing rapid flow of the fluid specimen at low pressure; flowing the fluid specimen containing the biological material through the solid phase material, the fluid specimen exiting the first chamber via the outlet opening; and lysing the fluid specimen in a second chamber fluidly connected to the first chamber, the second chamber comprising: an impeller which in use imparts rotational motion to the fluid specimen to mechanically lyse the fluid specimen.

13. The method of claim 12 wherein lysing the fluid specimen comprises agitating the specimen in the second chamber with a medium that includes a particulate material to mechanically lyse the specimen.

14. The method of claim 12 wherein introducing the fluid specimen into the first chamber of a device includes introducing the specimen into the first chamber containing a solid phase material having an affinity for at least one selected from the group consisting of a nucleic acid, a protein, a polypeptide, a His-tagged protein, a His-tagged polypeptide, a GST-tagged protein, a GST-tagged polypeptide, streptavidin, biotin, calmodulin, an antigen, an antibody, an immunoglobulin, albumin, DNA, RNA, double stranded DNA, an RNA/DNA heteroduplex, maltose binding protein, FLAG-tagged protein, FLAG-tagged polypeptide, MYC-tagged protein, MYC-tagged polypeptide MYC, a glycoprotein, a SNAP-tag, an enzyme, a lipid-containing biological material, a glycosylated protein, a phosphorylated protein, and a microorganism having a high cell wall lipid content.

15. The method of claim 12 wherein introducing the fluid specimen into the first chamber of a device includes introducing the specimen into the first chamber containing a solid phase material having an affinity for more than one biological material.

16. The method of claim 12 wherein introducing the fluid specimen into the first chamber of a device includes introducing the specimen into the first chamber containing a solid phase material comprising a particulate or a bead.

17. The method of claim 16 wherein introducing the fluid specimen into the first chamber of the device includes introducing the specimen into the first chamber containing a solid phase material comprising a particulate or bead having a diameter or lateral dimension of at least 10 µm.

18. The method of claim 12 wherein the first and second thin filter inserts have a pore size between about 10 µm and about 200 µm.

19. The method of claim 12 wherein introducing the fluid specimen into the first chamber includes introducing the specimen into the first chamber, and the first and second thin filter inserts comprise wire mesh inserts.

20. The method of claim 12 wherein introducing the fluid specimen into the first chamber includes introducing the specimen into the first chamber, and the first and second thin filter inserts comprise stainless steel mesh inserts.

21. The method of claim 12 wherein introducing the fluid specimen into the first chamber includes introducing the specimen into the first chamber, and the first and second thin filter inserts comprise plastic mesh inserts.

22. The method of claim 12, further comprising:
eluting the biological material captured on the solid phase material by flowing an elution medium through the solid phase material; and collecting an effluent containing the biological material, the effluent exiting the device.

* * * * *